US009708285B2

(12) United States Patent
Kato et al.

(10) Patent No.: US 9,708,285 B2
(45) Date of Patent: Jul. 18, 2017

(54) DIOXOLANE DERIVATIVE, LIQUID CRYSTAL COMPOSITION, LIQUID CRYSTAL ELEMENT, AND LIQUID CRYSTAL DISPLAY DEVICE

(71) Applicant: Semiconductor Energy Laboratory Co., LTD., Atsugi-shi, Kanagawa-ken (JP)

(72) Inventors: Momoko Kato, Fukushima (JP); Yasuhiro Niikura, Kanagawa (JP); Tetsuji Ishitani, Kanagawa (JP); Yuko Kawata, Kanagawa (JP)

(73) Assignee: Semiconductor Energy Laboratory Co., Ltd., Kanagawa-ken (JP)

( * ) Notice: Subject to any disclaimer, the term of this patent is extended or adjusted under 35 U.S.C. 154(b) by 0 days.

(21) Appl. No.: 15/063,894

(22) Filed: Mar. 8, 2016

(65) Prior Publication Data

US 2016/0185746 A1 Jun. 30, 2016

Related U.S. Application Data

(62) Division of application No. 14/447,178, filed on Jul. 30, 2014, now abandoned.

(30) Foreign Application Priority Data

| Jul. 31, 2013 | (JP) | 2013-159187 |
| Jul. 31, 2013 | (JP) | 2013-159194 |
| Jul. 31, 2013 | (JP) | 2013-159197 |

(51) Int. Cl.

| C07D 317/18 | (2006.01) |
| C07D 317/20 | (2006.01) |
| C09K 19/58 | (2006.01) |
| C07D 317/30 | (2006.01) |
| C09K 19/34 | (2006.01) |
| C07D 317/22 | (2006.01) |
| C07D 317/24 | (2006.01) |

(52) U.S. Cl.
CPC ......... *C07D 317/20* (2013.01); *C07D 317/18* (2013.01); *C07D 317/22* (2013.01); *C07D 317/24* (2013.01); *C07D 317/30* (2013.01); *C09K 19/3405* (2013.01); *C09K 19/588* (2013.01)

(58) Field of Classification Search
CPC .. C07D 317/14; C07D 317/18; C07D 317/20; C09K 19/586; C09K 19/588
See application file for complete search history.

(56) References Cited

U.S. PATENT DOCUMENTS 4,968,820 A * 11/1990 Scherowsky ........ C07D 307/20
544/295

| 7,342,632 B2 | 3/2008 | Miyachi et al. |
| 7,576,829 B2 | 8/2009 | Kikuchi et al. |
| 7,648,647 B2 | 1/2010 | Kikuchi et al. |
| 7,794,621 B2 | 9/2010 | Schott et al. |
| 8,395,740 B2 | 3/2013 | Kubota et al. |
| 8,642,141 B2 | 2/2014 | Tamura et al. |
| 8,758,870 B2 | 6/2014 | Niikura et al. |
| 2003/0189189 A1 | 10/2003 | Kirsch et al. |
| 2010/0184999 A1 | 7/2010 | Rawal et al. |
| 2011/0069245 A1 | 3/2011 | Haseba et al. |
| 2012/0132855 A1 | 5/2012 | Ishitani et al. |
| 2013/0155368 A1 | 6/2013 | Niikura et al. |
| 2014/0117285 A1 | 5/2014 | Tamura et al. |

FOREIGN PATENT DOCUMENTS

| DE | 102008051260 | 4/2010 |
| JP | 2006-348226 A | 12/2006 |
| JP | 2008-303381 A | 12/2008 |
| JP | 2009-057459 A | 3/2009 |
| WO | WO 98/00428 | 1/1998 |
| WO | WO 2005/090520 | 9/2005 |

OTHER PUBLICATIONS

CAPLUS 1992: 236027.*
Kikuchi.H et al., "Polymer-Stabilized Liquid Crystal Blue Phases", Nature Materials, Sep. 2, 2002, vol. 1, pp. 64-68.
Bauer.M et al., "Evaluation of chiral dopants for LCD applications", J. Soc. Inf. Display (Journal of the Society for Information Display), 2006, vol. 14, No. 9, pp. 805-812.
Goh.M et al., "Powerful helicity inducers: axially chiral binaphthyl derivatives", Liquid Crystals, Aug. 1, 2008, vol. 35, No. 8, pp. 953-965.
Kuball.H et al., "174. TADDOLs with Unprecedented Helical Twisting Power in Liquid Crystals", Helvetica Chimica Acta, 1997, vol. 80, No. 8, pp. 2507-2514.

(Continued)

*Primary Examiner* — Shean C Wu
(74) *Attorney, Agent, or Firm* — Nixon Peabody. LLP; Jeffrey L. Costellia

(57) ABSTRACT

A dioxolane derivative represented by formula (G1) is provided. The explanation of the substituents is given in the specification. The use of the dioxolane derivative enables the production of a liquid crystal composition and a liquid crystal display device including the liquid crystal composition.

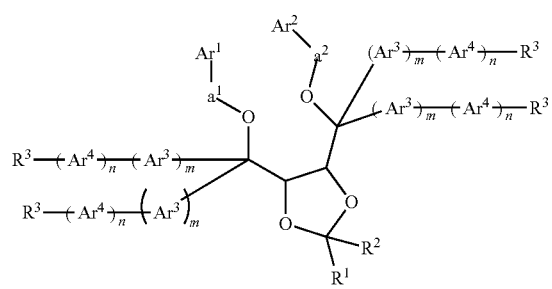

12 Claims, 17 Drawing Sheets

(56) References Cited

OTHER PUBLICATIONS

Awasaguchi.K et al., "Synthesis of Spiro C-Arylglycoriboside via Pd(II)-Catalyzed Spirocyclization", SYNLETT, 2010, No. 16, pp. 2392-2396.

* cited by examiner

DIOXOLANE DERIVATIVE, LIQUID CRYSTAL COMPOSITION, LIQUID CRYSTAL ELEMENT, AND LIQUID CRYSTAL DISPLAY DEVICE

BACKGROUND OF THE INVENTION

1. Field of the Invention

One embodiment of the present invention relates to a semiconductor device, a display device, a driving method thereof, or a manufacturing method thereof. In particular, one embodiment of the present invention relates to a novel dioxolane derivative, a liquid crystal composition that includes the dioxolane derivative, a liquid crystal element and a liquid crystal display device that include the liquid crystal composition, and manufacturing methods thereof.

2. Description of the Related Art

In recent years, liquid crystal has been used for a variety of devices; in particular, a liquid crystal display device (liquid crystal display) having features of thinness and lightness has been used for displays in a wide range of fields.

For higher resolution of moving images and less motion blur, shorter response time of liquid crystal has been required, and development thereof has been advanced (for example, see Patent Document 1).

As a display mode of liquid crystal capable of quick response, a display mode using a liquid crystal exhibiting a blue phase can be given. The mode using a liquid crystal exhibiting a blue phase achieves quick response, does not require an alignment film, and provides a wide viewing angle, and thus has been developed more actively for practical use (for example, see Patent Document 2).

REFERENCE

Patent Document

[Patent Document 1] Japanese Published Patent Application No. 2008-303381
[Patent Document 2] PCT International Publication No. 2005-090520

SUMMARY OF THE INVENTION

An object of one embodiment of the present invention is to provide a novel dioxolane derivative that can be used for various liquid crystal display devices. Another object is to provide a liquid crystal composition using the dioxolane derivative. Another object is to provide a liquid crystal element and a liquid crystal display device each including the liquid crystal composition.

Note that the descriptions of these objects do not disturb the existence of other objects. In one embodiment of the present invention, there is no need to achieve all the objects. Other objects will be apparent from and can be derived from the description of the specification, the drawings, the claims, and the like.

An embodiment of the invention disclosed herein is a novel dioxolane derivative represented by General Formula (G1). The dioxolane derivative can function as a chiral material in a liquid crystal composition.

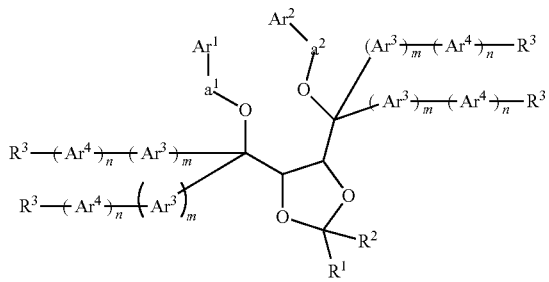

(G1)

In General Formula (G1), $Ar^1$ and $Ar^2$ independently represent hydrogen, a substituted or unsubstituted aryl group having 6 to 12 carbon atoms, a substituted or unsubstituted cycloalkyl group having 3 to 12 carbon atoms, or a substituted or unsubstituted cycloalkenyl group having 4 to 12 carbon atoms; $Ar^3$ and $Ar^4$ independently represent a substituted or unsubstituted arylene group having 6 to 12 carbon atoms, a substituted or unsubstituted cycloalkylene group having 3 to 12 carbon atoms, or a substituted or unsubstituted cycloalkenylene group having 4 to 12 carbon atoms; m represents any of 1 to 3, and n represents any of 0 to 3; $a^1$ and $a^2$ independently represent a substituted or unsubstituted alkylene group having 1 to 4 carbon atoms or a single bond; $R^1$ and $R^2$ independently represent hydrogen, a substituted or unsubstituted alkyl group having 1 to 6 carbon atoms, a substituted or unsubstituted alkoxy group having 1 to 6 carbon atoms, or a substituted or unsubstituted aryl group having 6 to 12 carbon atoms; and $R^3$ represents hydrogen, a substituted or unsubstituted alkyl group having 1 to 6 carbon atoms, or a substituted or unsubstituted alkoxy group having 1 to 6 carbon atoms.

In General Formulae (G1), examples of the substituents on the aryl group having 6 to 12 carbon atoms, the cycloalkyl group having 3 to 12 carbon atoms, the cycloalkenyl group having 4 to 12 carbon atoms, the arylene group having 6 to 12 carbon atoms, the cycloalkylene group having 3 to 12 carbon atoms, the cycloalkenylene group having 4 to 12 carbon atoms, the alkylene group having 1 to 4 carbon atoms, the alkyl group having 1 to 6 carbon atoms, and the alkoxy group having 1 to 6 carbon atoms are fluorine (F), chlorine (Cl), bromine (Br), iodine (I), a cyano group (CN), a trifluoromethylsulfonyl group ($SO_2CF_3$), a trifluoromethyl group ($CF_3$), a nitro group ($NO_2$), an isothiocyanate group (NCS), and a pentafluorosulfanyl group ($SF_5$).

Another embodiment of the present invention is a dioxolane derivative represented by the following Structural Formula (100).

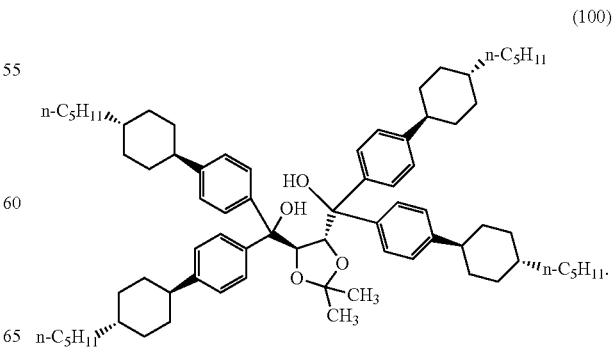

(100)

Another embodiment of the present invention is a dioxolane derivative represented by the following Structural Formula (101).

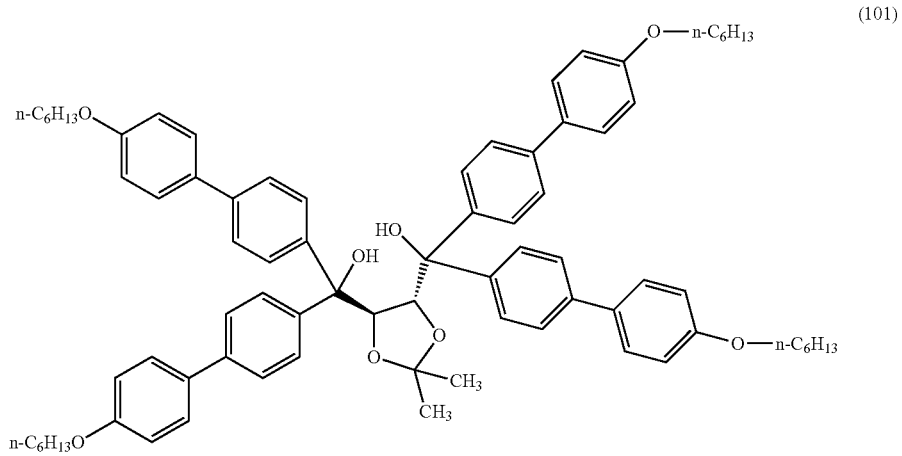

(101)

Another embodiment of the present invention is a dioxolane derivative represented by the following Structural Formula (102).

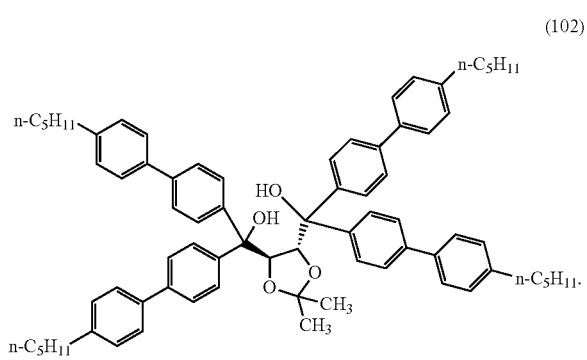

(102)

Another embodiment of the invention disclosed herein is a novel dioxolane derivative represented by General Formula (G2).

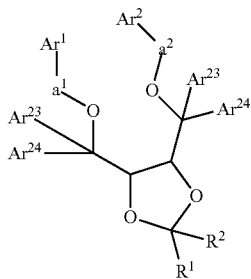

(G2)

In General Formula (G2), $Ar^1$ and $Ar^2$ independently represent hydrogen, a substituted or unsubstituted aryl group having 6 to 12 carbon atoms, a substituted or unsubstituted cycloalkyl group having 3 to 12 carbon atoms, or a substituted or unsubstituted cycloalkenyl group having 4 to 12 carbon atoms; $Ar^{23}$ and $Ar^{24}$ independently represent a substituted or unsubstituted pyrenyl group or a substituted or unsubstituted naphthyl group; $a^1$ and $a^2$ independently represent a substituted or unsubstituted alkylene group having 1 to 4 carbon atoms or a single bond; and $R^1$ and $R^2$ independently represent hydrogen, a substituted or unsubstituted alkyl group having 1 to 6 carbon atoms, a substituted or unsubstituted alkoxy group having 1 to 6 carbon atoms, or a substituted or unsubstituted aryl group having 6 to 12 carbon atoms.

In General Formula (G2), examples of the substituents on the aryl group having 6 to 12 carbon atoms, the cycloalkyl group having 3 to 12 carbon atoms, the cycloalkenyl group having 4 to 12 carbon atoms, the pyrenyl group, the naphthyl group, the alkylene group having 1 to 4 carbon atoms, the alkyl group having 1 to 6 carbon atoms, and the alkoxy group having 1 to 6 carbon atoms are fluorine (F), chlorine (Cl), bromine (Br), iodine (I), a cyano group (CN), a trifluoromethylsulfonyl group ($SO_2CF_3$), a trifluoromethyl group ($CF_3$), a nitro group ($NO_2$), an isothiocyanate group (NCS), and a pentafluorosulfanyl group ($SF_5$).

Another embodiment of the present invention is a dioxolane derivative represented by General Formula (G3).

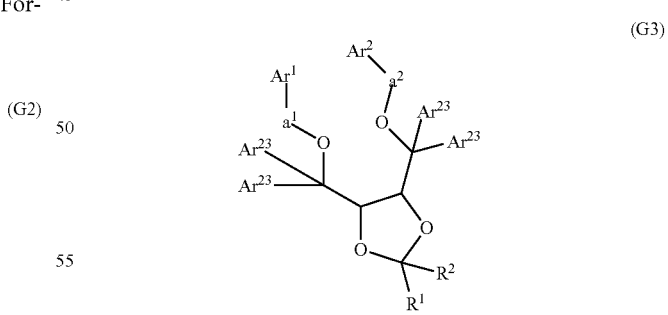

(G3)

In General Formula (G3), $Ar^1$ and $Ar^2$ independently represent hydrogen, a substituted or unsubstituted aryl group having 6 to 12 carbon atoms, a substituted or unsubstituted cycloalkyl group having 3 to 12 carbon atoms, or a substituted or unsubstituted cycloalkenyl group having 4 to 12 carbon atoms; $Ar^{23}$ represents a substituted or unsubstituted pyrenyl group or a substituted or unsubstituted naphthyl group; $a^1$ and $a^2$ independently represent a substituted or unsubstituted alkylene group having 1 to 4 carbon atoms or a single bond; and $R^1$ and $R^2$ independently represent hydrogen, a substituted or unsubstituted alkyl group having 1 to 6 carbon atoms, a substituted or unsubstituted alkoxy group having 1 to 6 carbon atoms, or a substituted or unsubstituted aryl group having 6 to 12 carbon atoms.

Furthermore, in General Formula (G3), examples of the substituents on the aryl group having 6 to 12 carbon atoms, the cycloalkyl group having 3 to 12 carbon atoms, the cycloalkenyl group having 4 to 12 carbon atoms, the pyrenyl group, the naphthyl group, the alkylene group having 1 to 4 carbon atoms, the alkyl group having 1 to 6 carbon atoms, and the alkoxy group having 1 to 6 carbon atoms are fluorine (F), chlorine (Cl), bromine (Br), iodine (I), a cyano group (CN), a trifluoromethylsulfonyl group ($SO_2CF_3$), a trifluoromethyl group ($CF_3$), a nitro group ($NO_2$), an isothiocyanate group (NCS), and a pentafluorosulfanyl group ($SF_5$).

Another embodiment of the present invention is a dioxolane derivative represented by Structural Formula (200).

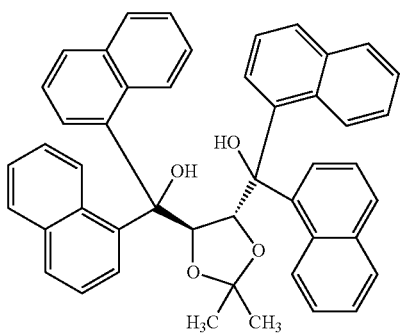

(200)

Another embodiment of the present invention is a dioxolane derivative represented by Structural Formula (201).

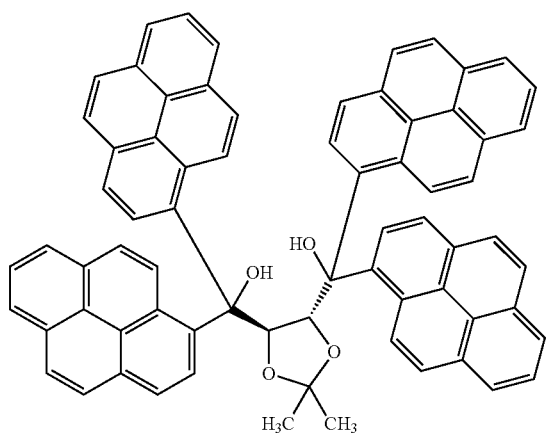

(201)

Another embodiment of the invention disclosed herein is a novel dioxolane derivative represented by General Formula (G4). The dioxolane derivative can function as a chiral material in a liquid crystal composition.

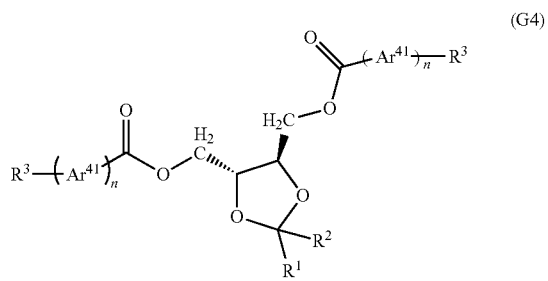

(G4)

In General Formula (G4), $Ar^{41}$ represents a substituted or unsubstituted arylene group having 6 to 12 carbon atoms, a substituted or unsubstituted cycloalkylene group having 3 to 12 carbon atoms, or a substituted or unsubstituted cycloalkenylene group having 4 to 12 carbon atoms; n represents any of 0 to 3; $R^1$ and $R^2$ independently represent hydrogen, a substituted or unsubstituted alkyl group having 1 to 6 carbon atoms, a substituted or unsubstituted alkoxy group having 1 to 6 carbon atoms, or a substituted or unsubstituted aryl group having 6 to 12 carbon atoms; $R^3$ represents hydrogen, a substituted or unsubstituted alkyl group having 1 to 6 carbon atoms, or a substituted or unsubstituted alkoxy group having 1 to 6 carbon atoms (when n is 0, $R^3$ does not include hydrogen).

In General Formula (G4), examples of the substituents on the arylene group having 6 to 12 carbon atoms, the cycloalkylene group having 3 to 12 carbon atoms, the cycloalkenylene group having 4 to 12 carbon atoms, the alkyl group having 1 to 6 carbon atoms, the alkoxy group having 1 to 6 carbon atoms, and the aryl group having 6 to 12 carbon atoms are fluorine (F), chlorine (Cl), bromine (Br), iodine (I), a cyano group (CN), a trifluoromethylsulfonyl group ($SO_2CF_3$), a trifluoromethyl group ($CF_3$), a nitro group ($NO_2$), an isothiocyanate group (NCS), and a pentafluorosulfanyl group ($SF_5$).

Another embodiment of the present invention is a dioxolane derivative represented by the following Structural Formula (300).

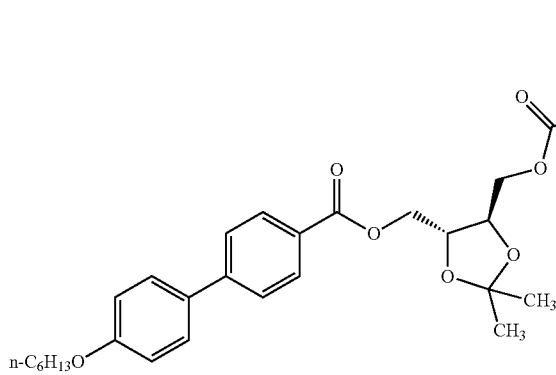

(300)

Another embodiment of the present invention is a liquid crystal composition including at least a nematic liquid crystal and any of the above dioxolane derivatives.

Another embodiment of the present invention is a liquid crystal composition exhibiting a blue phase and including at least a nematic liquid crystal and any of the above dioxolane derivatives. Note that a blue phase is exhibited in a liquid crystal composition having strong twisting power and has a double twist structure. The liquid crystal composition that can exhibit a blue phase shows a cholesteric phase, a cholesteric blue phase, an isotropic phase, or the like depending on conditions.

Indicators of the strength of twisting power include the helical pitch, the selective reflection wavelength, HTP (helical twisting power), and the diffraction wavelength.

When the twisting power of the liquid crystal composition that exhibits a blue phase is strong, the transmittance of the liquid crystal composition in the absence of an applied voltage (at an applied voltage of 0 V) can be reduced by addition of a small amount of chiral material. In addition, the liquid crystal can be easily operated by application of voltage, whereby high transmittance can be achieved. Thus, a liquid crystal display device including the liquid crystal composition can exhibit high contrast.

The liquid crystal composition of one embodiment of the present invention includes at least the dioxolane derivative represented by General Formula (G1), (G2), (G3), or (G4) and a nematic liquid crystal. The dioxolane derivative represented by General Formula (G1), (G2), (G3), or (G4) has chiral centers; therefore, when included in a liquid crystal composition, the dioxolane derivative can serve as a chiral material that induces twist of the liquid crystal composition to cause helical orientation.

In addition, since the dioxolane derivative represented by General Formula (G1), (G2), (G3), or (G4) is a chiral material with strong twisting power, the proportion thereof in a liquid crystal composition can be lower than or equal to 15 wt %, lower than or equal to 10 wt %, or lower than or equal to 8 wt %. In general, when a large amount of chiral material is added in order to improve the twisting power of the liquid crystal composition, driving voltage for driving a liquid crystal element including the liquid crystal composition tends to increase. However, in the liquid crystal composition of one embodiment of the present invention, the amount of chiral material can be reduced, so that an increase in the driving voltage of the liquid crystal element can be suppressed. Thus, a reduction in power consumption of the liquid crystal display device can be achieved.

One embodiment of the present invention includes a liquid crystal element, and a liquid crystal display device, an electronic appliance each including the above liquid crystal composition.

With one embodiment of the present invention, a novel dioxolane derivative that can be used for various liquid crystal display devices can be provided. A novel liquid crystal composition using the dioxolane derivative can be provided. Another object is to provide a liquid crystal element and a liquid crystal display device each including the liquid crystal composition can be provided.

BRIEF DESCRIPTION OF THE DRAWINGS

In the accompanying drawings:

FIGS. 4A1, 4A2, and 4B illustrate liquid crystal display modules;

DETAILED DESCRIPTION OF THE INVENTION

Figure 1A:
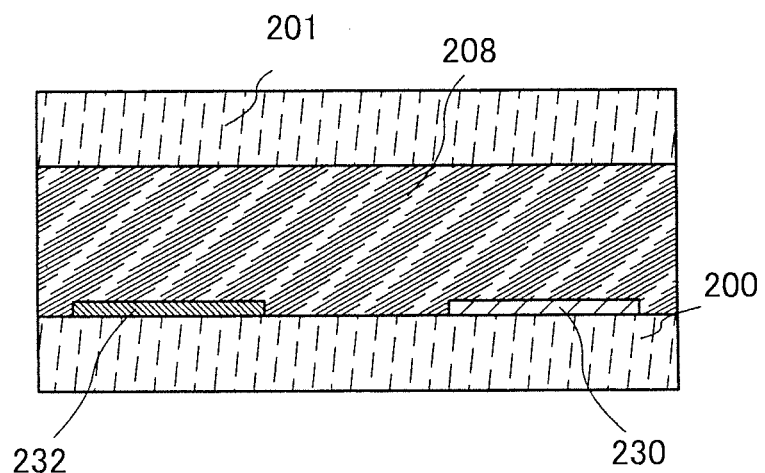
FIGS. 1A and 1B are conceptual diagrams each illustrating a liquid crystal element.

Embodiments of the invention disclosed in this specification will be described below with reference to the accompanying drawings. Note that the invention disclosed in this specification is not limited to the following description, and it is easily understood by those skilled in the art that modes and details of the invention can be modified in various ways. Therefore, the invention disclosed in this specification is not construed as being limited to the description of the following embodiments or examples.

(Embodiment 1)

In this embodiment, a novel dioxolane derivative of one embodiment of the present invention will be described.

One embodiment of the present invention is a dioxolane derivative represented by General Formula (G1).

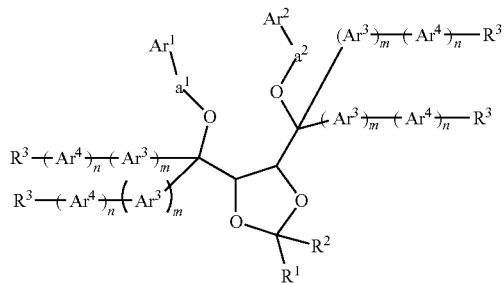

(G1)

In General Formula (G1), $Ar^1$ and $Ar^2$ independently represent hydrogen, a substituted or unsubstituted aryl group having 6 to 12 carbon atoms, a substituted or unsubstituted cycloalkyl group having 3 to 12 carbon atoms, or a substituted or unsubstituted cycloalkenyl group having 4 to 12 carbon atoms; $Ar^3$ and $Ar^4$ independently represent a substituted or unsubstituted arylene group having 6 to 12 carbon atoms, a substituted or unsubstituted cycloalkylene group having 3 to 12 carbon atoms, or a substituted or unsubstituted cycloalkenylene group having 4 to 12 carbon atoms; m represents any of 1 to 3, and n represents any of 0 to 3; $a^1$ and $a$ independently represent a substituted or unsubstituted alkylene group having 1 to 4 carbon atoms or a single bond; $R^1$ and $R^2$ independently represent hydrogen, a substituted or unsubstituted alkyl group having 1 to 6 carbon atoms, a substituted or unsubstituted alkoxy group having 1 to 6 carbon atoms, or a substituted or unsubstituted aryl group having 6 to 12 carbon atoms; and $R^3$ represents hydrogen, a substituted or unsubstituted alkyl group having 1 to 6 carbon atoms, or a substituted or unsubstituted alkoxy group having 1 to 6 carbon atoms.

In General Formulae (G1), examples of the substituents on the aryl group having 6 to 12 carbon atoms, the cycloalkyl group having 3 to 12 carbon atoms, the cycloalkenyl group having 4 to 12 carbon atoms, the arylene group having 6 to 12 carbon atoms, the cycloalkylene group having 3 to 12 carbon atoms, the cycloalkenylene group having 4 to 12 carbon atoms, the alkylene group having 1 to 4 carbon atoms, the alkyl group having 1 to 6 carbon atoms, and the alkoxy group having 1 to 6 carbon atoms are fluorine (F), chlorine (Cl), bromine (Br), iodine (I), a cyano group (CN), a trifluoromethylsulfonyl group ($SO_2CF_3$), a trifluoromethyl group ($CF_3$), a nitro group ($NO_2$), an isothiocyanate group (NCS), and a pentafluorosulfanyl group ($SF_5$).

Specific examples of the dioxolane derivative represented by General Formula (G1) include the dioxolane derivatives represented by Structural Formulae (100) to (109). However, the present invention is not limited to these examples.

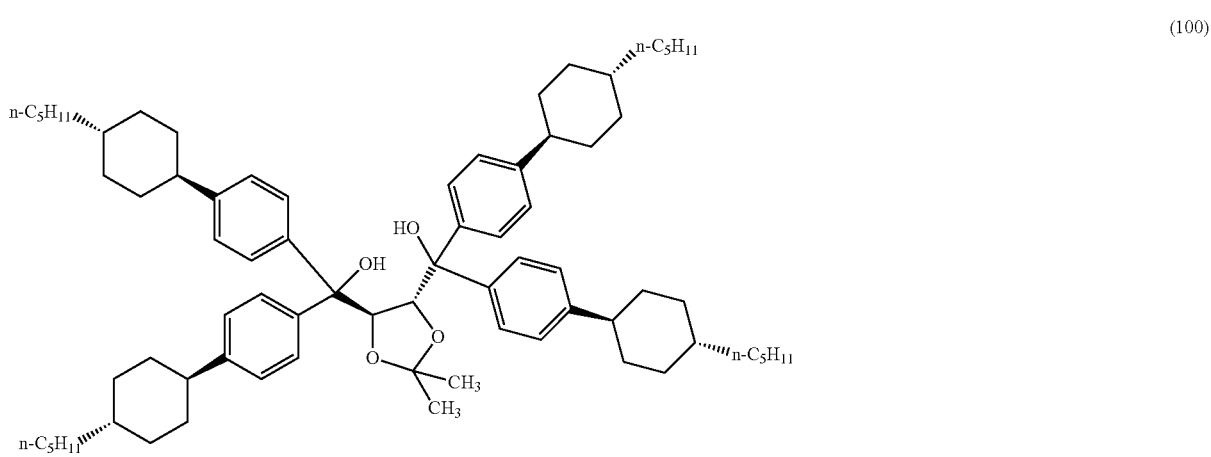

(100)

(101)
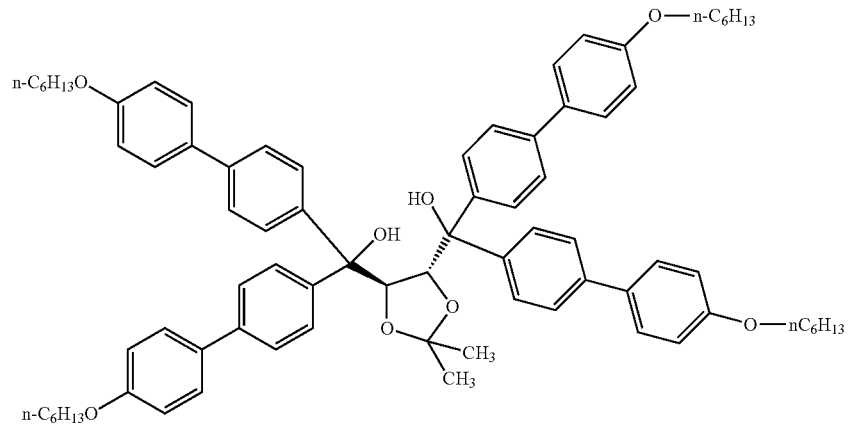
(102)
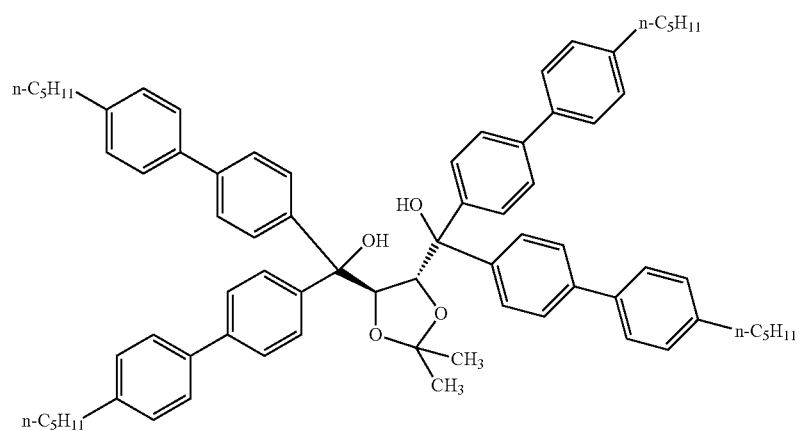
(103)
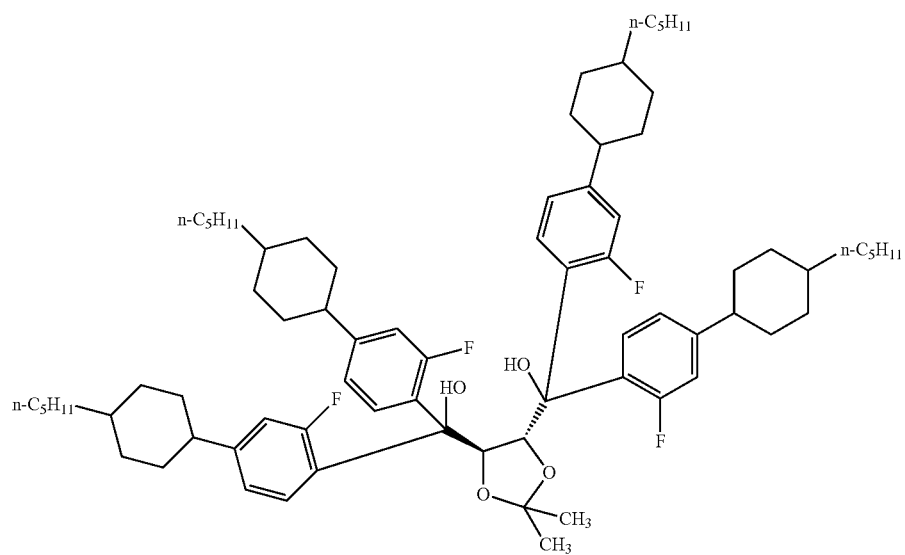

-continued
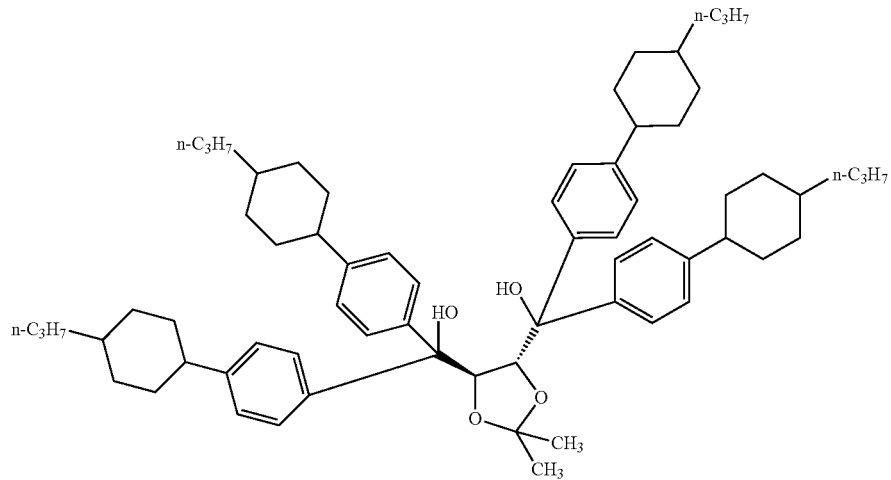
(104)
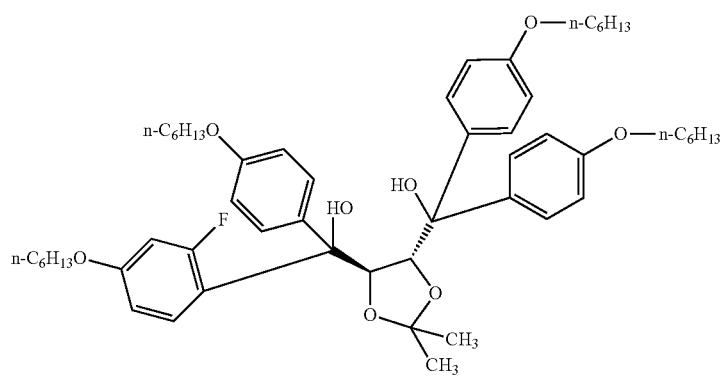
(105)
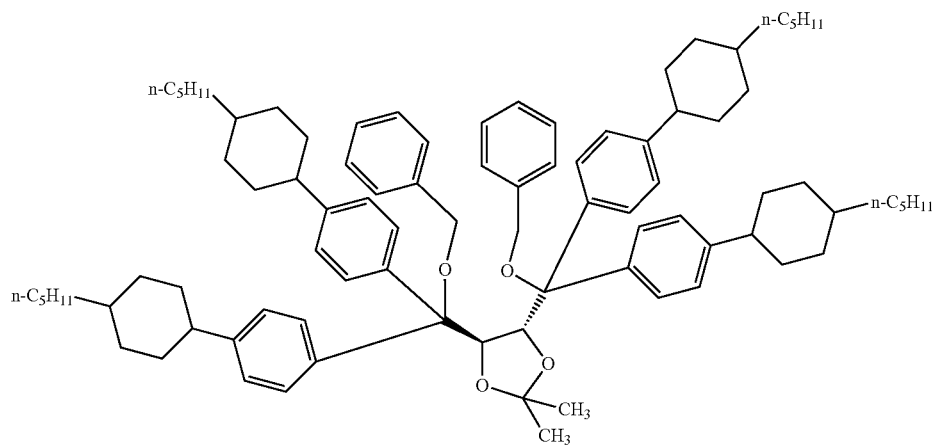
(106)

(107)
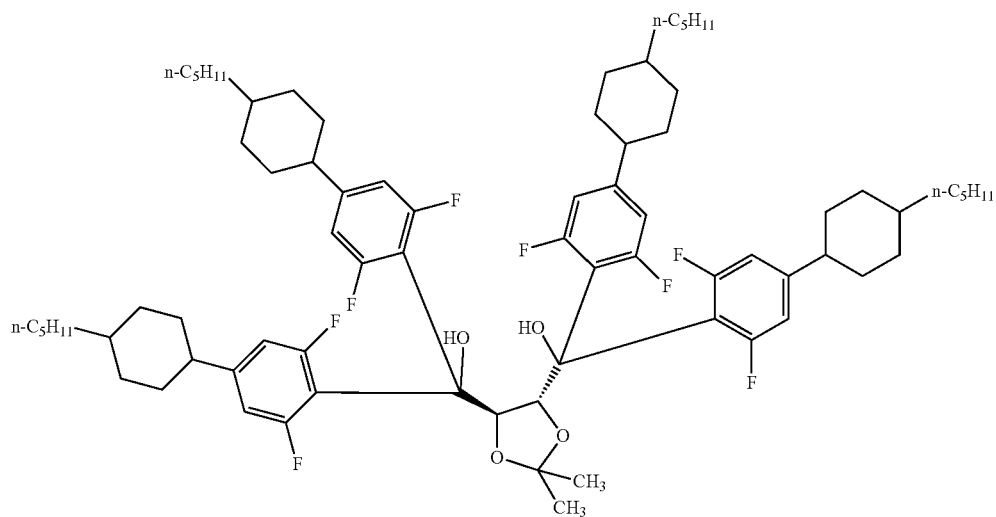
(108)
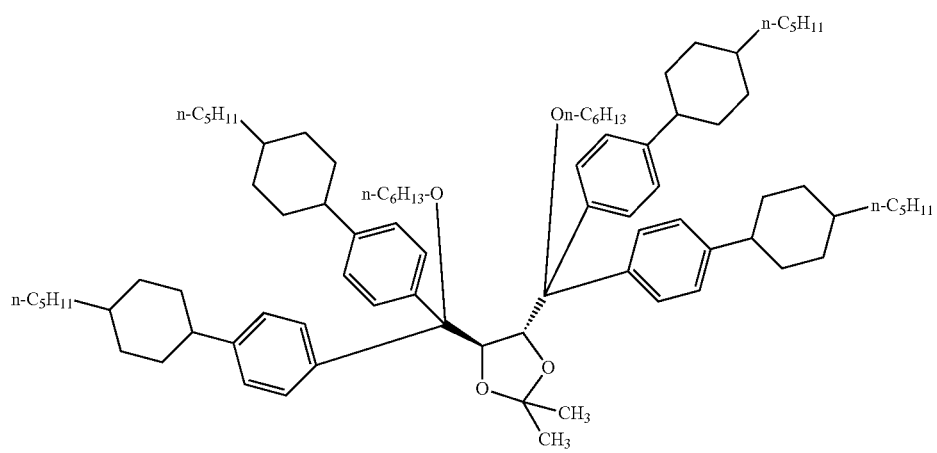
(109)
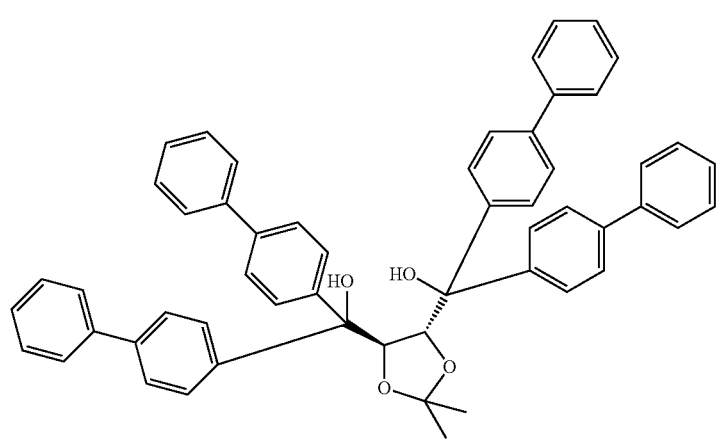

A variety of reactions can be applied to a method for synthesizing the dioxolane derivative of this embodiment. The following is an example of a method for synthesizing the dioxolane derivative represented by General Formula (G1).

The dioxolane derivative represented by General Formula (G1) can be synthesized by the reactions represented by the following Scheme (K1-1).

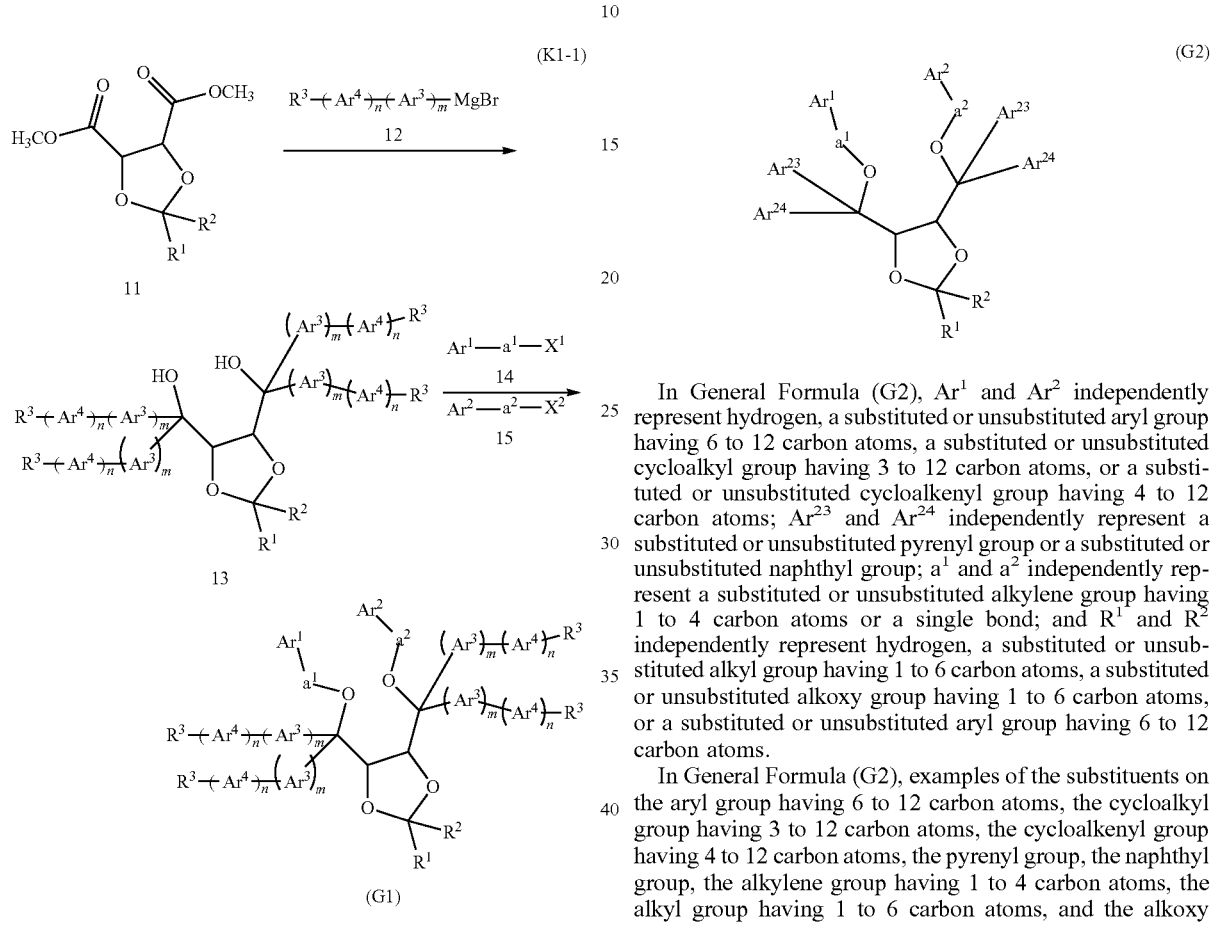

The reaction of a 1,3-dioxolane-4,5-dicarboxylic ester (compound 11) with four equivalents of a Grignard reagent (compound 12) gives a compound 13 having a 1,3-dioxolane skeleton. The hydroxyl groups of compound 13 are converted to alkoxy groups through the Williamson ether synthesis reaction or the like by using organic halides (compounds 14 and 15; compounds 14 and 15 may be the same), leading to the target dioxolane derivative (General Formula (G1)) (Scheme (K1-1)).

The dioxolane derivative represented by General Formula (G1) has chiral centers; therefore, when included in a liquid crystal composition, the dioxolane derivative can serve as a chiral material that induces twist of the liquid crystal composition to cause helical orientation.

For example, the liquid crystal composition including the dioxolane derivative represented by General Formula (G1) as a chiral material can be used for a liquid crystal display device in a lateral electric field mode such as a blue phase mode, a liquid crystal display device in a vertical electric field mode such as a TN mode or a cholesteric liquid crystal mode, and the like.

The structures, methods, and the like described in this embodiment can be combined as appropriate with any of the structures, methods, and the like described in the other embodiments.

(Embodiment 2)

In this embodiment, a novel dioxolane derivative of one embodiment of the present invention will be described.

One embodiment of the present invention is a dioxolane derivative represented by General Formula (G2).

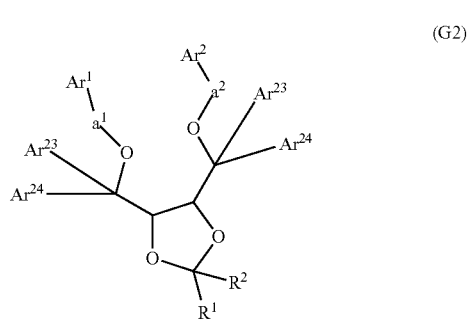

In General Formula (G2), $Ar^1$ and $Ar^2$ independently represent hydrogen, a substituted or unsubstituted aryl group having 6 to 12 carbon atoms, a substituted or unsubstituted cycloalkyl group having 3 to 12 carbon atoms, or a substituted or unsubstituted cycloalkenyl group having 4 to 12 carbon atoms; $Ar^{23}$ and $Ar^{24}$ independently represent a substituted or unsubstituted pyrenyl group or a substituted or unsubstituted naphthyl group; $a^1$ and $a^2$ independently represent a substituted or unsubstituted alkylene group having 1 to 4 carbon atoms or a single bond; and $R^1$ and $R^2$ independently represent hydrogen, a substituted or unsubstituted alkyl group having 1 to 6 carbon atoms, a substituted or unsubstituted alkoxy group having 1 to 6 carbon atoms, or a substituted or unsubstituted aryl group having 6 to 12 carbon atoms.

In General Formula (G2), examples of the substituents on the aryl group having 6 to 12 carbon atoms, the cycloalkyl group having 3 to 12 carbon atoms, the cycloalkenyl group having 4 to 12 carbon atoms, the pyrenyl group, the naphthyl group, the alkylene group having 1 to 4 carbon atoms, the alkyl group having 1 to 6 carbon atoms, and the alkoxy group having 1 to 6 carbon atoms are fluorine (F), chlorine (Cl), bromine (Br), iodine (I), a cyano group (CN), a trifluoromethylsulfonyl group ($SO_2CF_3$), a trifluoromethyl group ($CF_3$), a nitro group ($NO_2$), an isothiocyanate group (NCS), and a pentafluorosulfanyl group ($SF_5$).

In General Formula (G2), $Ar^{23}$ and $Ar^{24}$ may be the same; in which case the dioxolane derivative is represented by General Formula (G3).

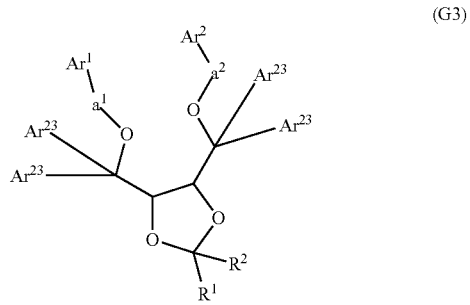

Specific examples of the dioxolane derivative represented by General Formula (G2) include the dioxolane derivatives represented by Structural Formulae (200) to (211). However, the present invention is not limited to these examples.
(200)
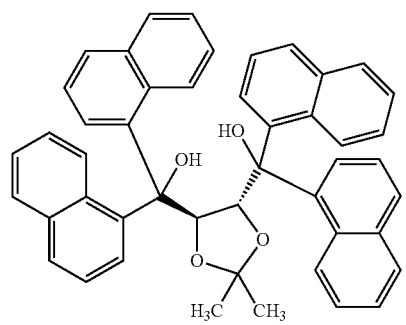
(201)
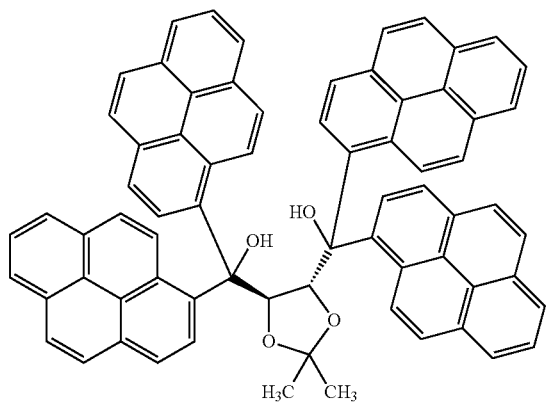
(202)
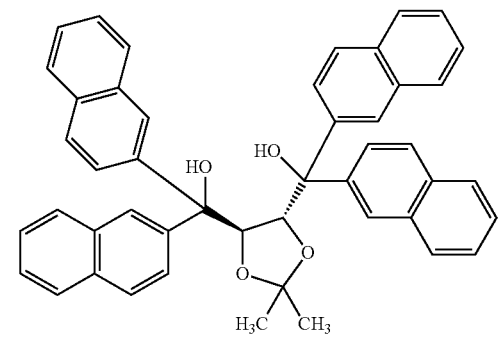
(203)
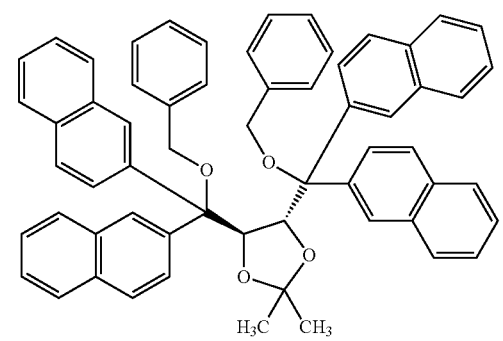
(204)
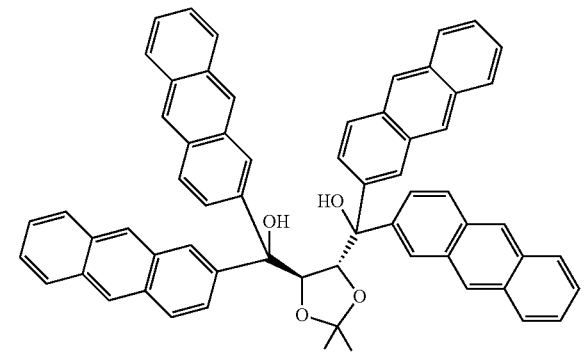
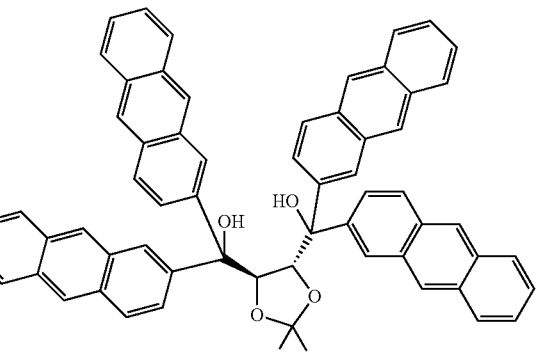
(206)
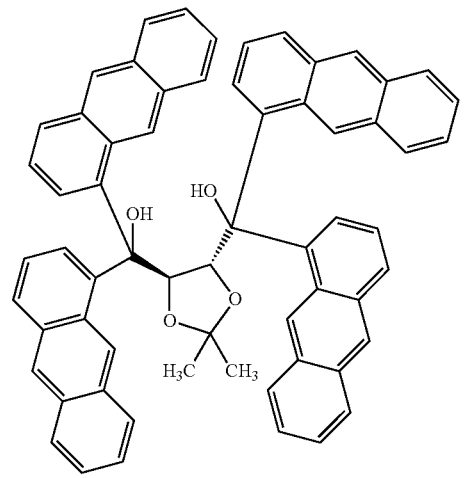

(207)
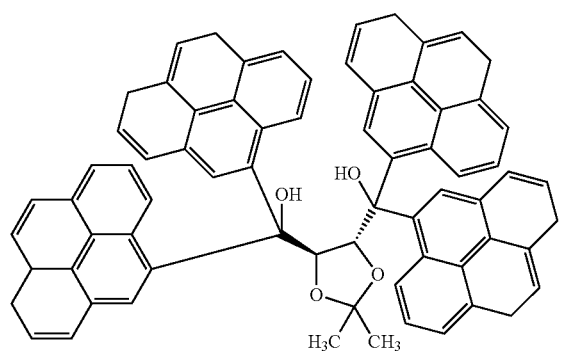

(208)
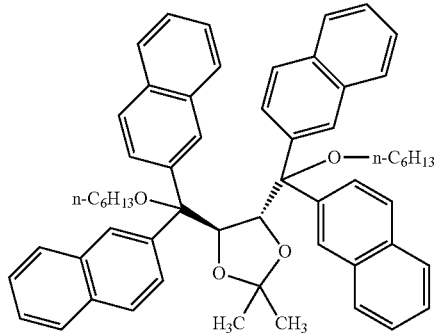

(209)
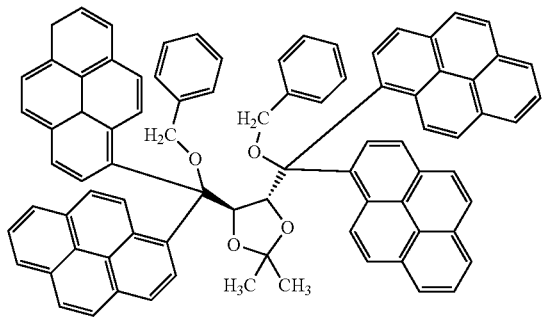

(210)
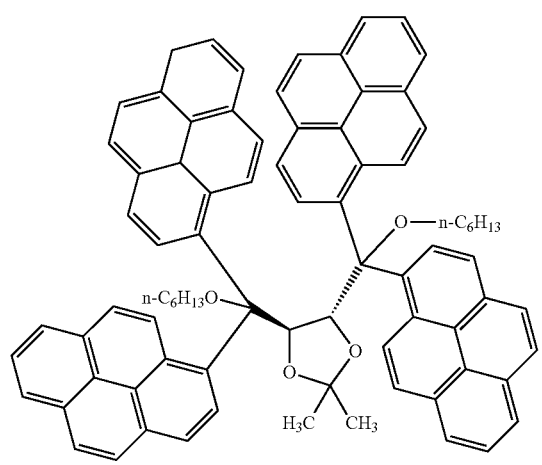

(211)
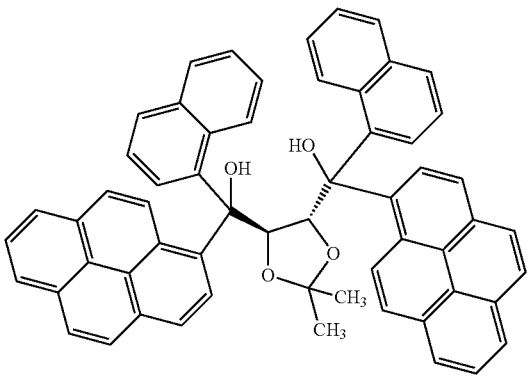

A variety of reactions can be applied to a method for synthesizing the dioxolane derivative of this embodiment. The following is an example of a method for synthesizing the dioxolane derivative represented by General Formula (G2).

The dioxolane derivative represented by General Formula (G2) can be synthesized by the reactions represented by the following Scheme (K2-1).

(K2-1)
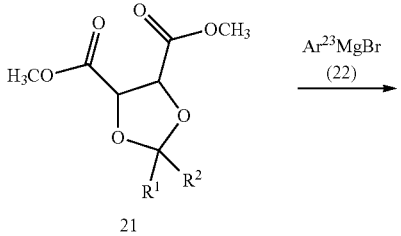
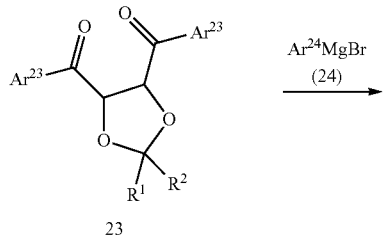
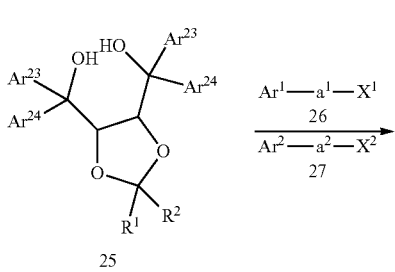

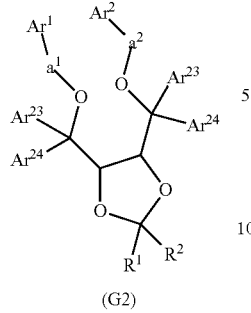

(G2)

The reaction of a 1,3-dioxolane-4,5-dicarboxylic ester (compound 21) with two equivalents of a Grignard reagent (compound 22) gives a compound 23 having a 1,3-dioxolane skeleton. Then, compound 23 is subjected to the reaction with two equivalents of a Grignard reagent (compound 24) to obtain a compound having a 1,3-dioxolane skeleton (compound 25). The hydroxyl group of compound 25 is converted to an alkoxy group through the Williamson ether synthesis reaction or the like by using organic halides (compounds 26 and 27; compounds 26 and 27 may be the same), leading to the target dioxolane derivative (General Formula (G2)) (Scheme (K2-1)).

The dioxolane derivative represented by General Formula (G2) or (G3) has chiral centers; therefore, when included in a liquid crystal composition, the dioxolane derivative can serve as a chiral material that induces twist of the liquid crystal composition to cause helical orientation.

For example, the liquid crystal composition including the dioxolane derivative represented by General Formula (G2) as a chiral material can be used for a liquid crystal display device in a lateral electric field mode such as a blue phase mode, a liquid crystal display device in a vertical electric field mode such as a TN mode or a cholesteric liquid crystal mode, and the like.

The structures, methods, and the like described in this embodiment can be combined as appropriate with any of the structures, methods, and the like described in the other embodiments.

(Embodiment 3)

In this embodiment, a novel dioxolane derivative of one embodiment of the present invention will be described.

One embodiment of the present invention is a dioxolane derivative represented by General Formula (G4).

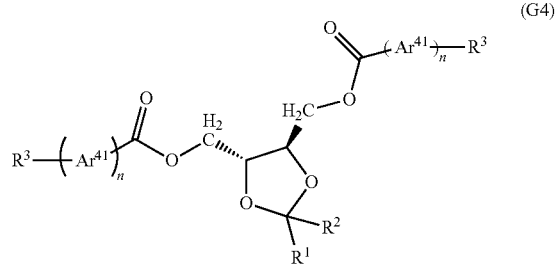

(G4)

In General Formula (G4), $Ar^{41}$ represents a substituted or unsubstituted arylene group having 6 to 12 carbon atoms, a substituted or unsubstituted cycloalkylene group having 3 to 12 carbon atoms, or a substituted or unsubstituted cycloalkenylene group having 4 to 12 carbon atoms; n represents any of 0 to 3; $R^1$ and $R^2$ independently represent hydrogen, a substituted or unsubstituted alkyl group having 1 to 6 carbon atoms, a substituted or unsubstituted alkoxy group having 1 to 6 carbon atoms, or a substituted or unsubstituted aryl group having 6 to 12 carbon atoms; and $R^3$ represents hydrogen, a substituted or unsubstituted alkyl group having 1 to 6 carbon atoms, or a substituted or unsubstituted alkoxy group having 1 to 6 carbon atoms (when n is 0, $R^3$ does not include hydrogen).

In General Formula (G4), examples of the substituents on the arylene group having 6 to 12 carbon atoms, the cycloalkylene group having 3 to 12 carbon atoms, the cycloalkenylene group having 4 to 12 carbon atoms, the alkyl group having 1 to 6 carbon atoms, the alkoxy group having 1 to 6 carbon atoms, and the aryl group having 6 to 12 carbon atoms are fluorine (F), chlorine (Cl), bromine (Br), iodine (I), a cyano group (CN), a trifluoromethylsulfonyl group ($SO_2CF_3$), a trifluoromethyl group ($CF_3$), a nitro group ($NO_2$), an isothiocyanate group (NCS), and a pentafluorosulfanyl group ($SF_5$).

Specific examples of the dioxolane derivative represented by General Formula (G4) include the dioxolane derivatives represented by Structural Formulae (300) to (309). However, the present invention is not limited to these examples.

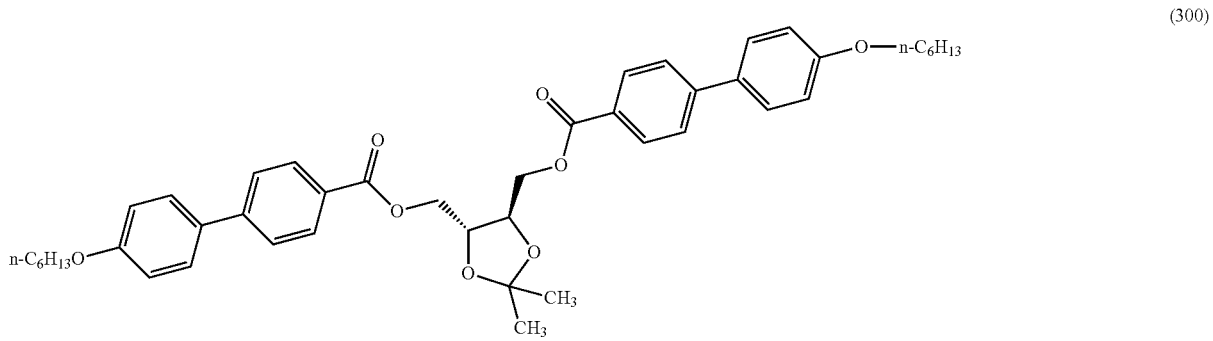

(300)

(301)
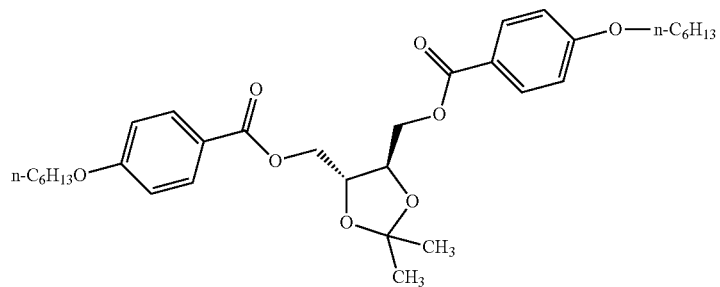
(302)
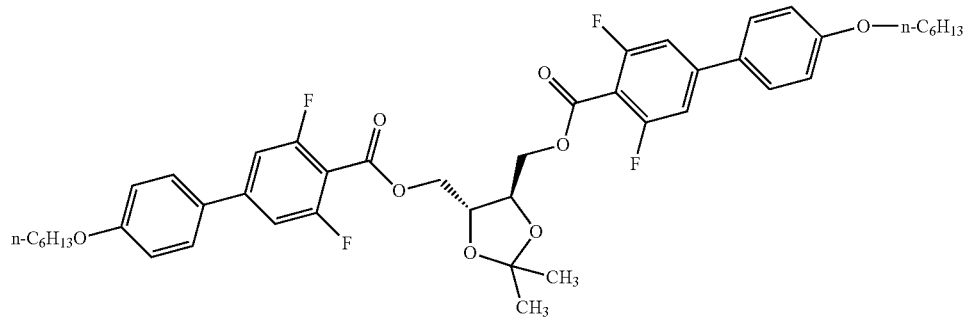
(303)
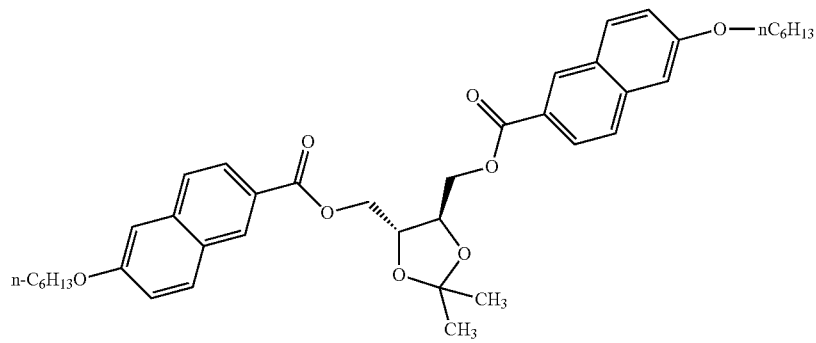
(304)
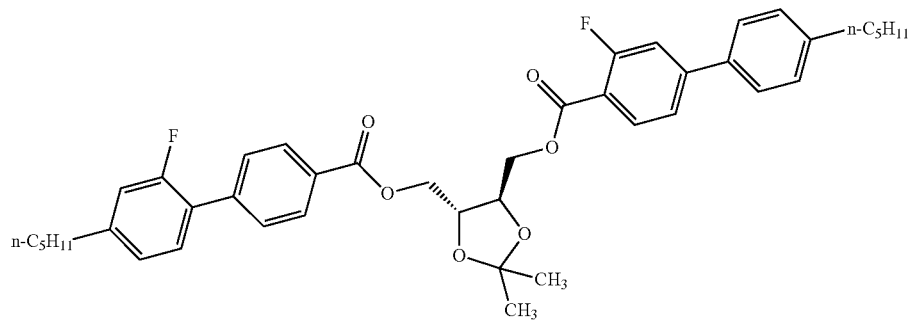
(305)
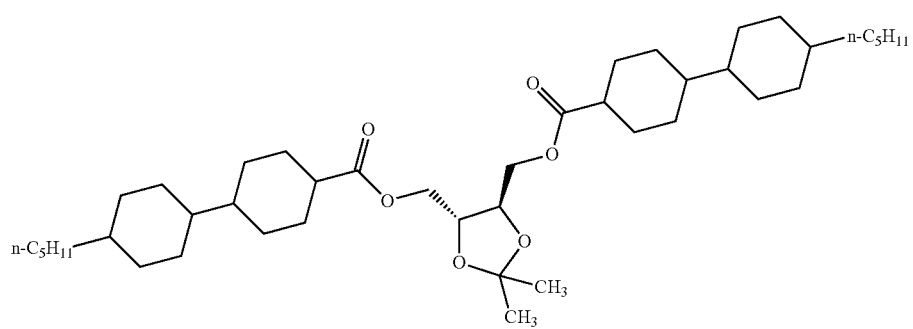

(306)

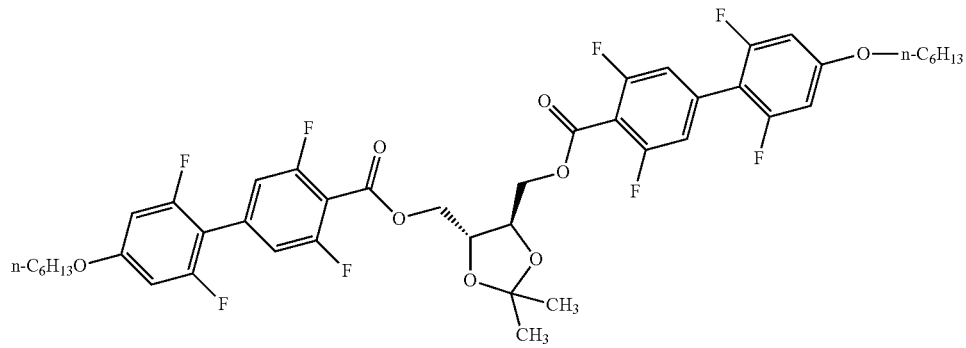

(307)

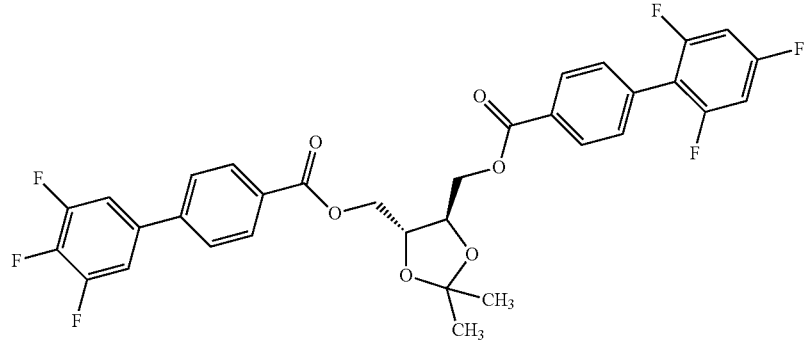

(308)

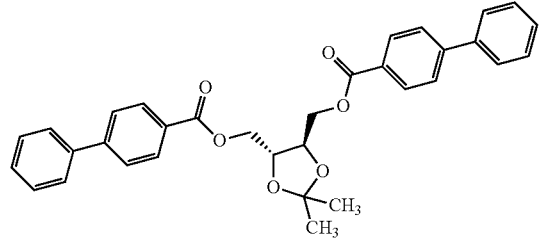

(309)

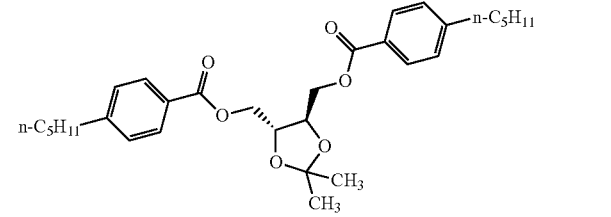

A variety of reactions can be applied to a method for synthesizing the dioxolane derivative of this embodiment. The following is an example of a method for synthesizing the dioxolane derivative represented by General Formula (G4).

The dioxolane derivative represented by General Formula (G4) can be synthesized by the reactions represented by the following Scheme (K3-1).

(K3-1)

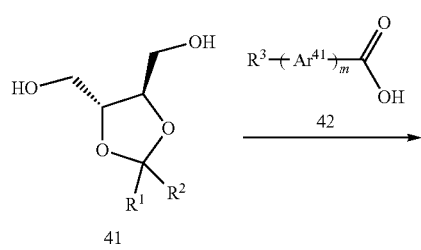

-continued

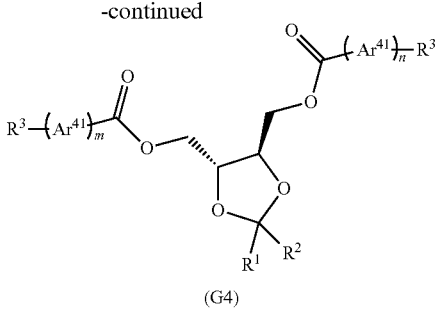

(G4)

The esterification of a 1,3-dioxolane-4,5-dimethanol (compound 41) with two equivalents of a carboxylic acid (compound 42) gives the target dioxolane derivative (General Formula (G4)) (Scheme (K3-1)).

The dioxolane derivative represented by General Formula (G4) has chiral centers; therefore, when included in a liquid crystal composition, the dioxolane derivative can serve as a chiral material that induces twist of the liquid crystal composition to cause helical orientation.

For example, the liquid crystal composition including the dioxolane derivative represented by General Formula (G4) as a chiral material can be used for a liquid crystal display device in a lateral electric field mode such as a blue phase mode, a liquid crystal display device in a vertical electric field mode such as a TN mode or a cholesteric liquid crystal mode, and the like.

The structures, methods, and the like described in this embodiment can be combined as appropriate with any of the structures, methods, and the like described in the other embodiments.

(Embodiment 4)

In this embodiment, a liquid crystal composition including any of the dioxolane derivatives described in Embodiments 1 to 3, each of which is one embodiment of the present invention, and a liquid crystal element or liquid crystal display device each including the liquid crystal composition will be described with reference to FIGS. 1A and 1B.

The liquid crystal composition of this embodiment includes a nematic liquid crystal and any of the dioxolane derivatives described in Embodiments 1 to 3.

As described above, the dioxolane derivative represented by General Formula (G1), (G2), (G3), or (G4) can serve as a chiral material. In addition, since the dioxolane derivative represented by General Formula (G1), (G2), (G3), or (G4) is a chiral material with strong twisting power, the proportion thereof in a liquid crystal composition can be lower than or equal to 15 wt %, lower than or equal to 10 wt %, or lower than or equal to 8 wt %.

There is no particular limitation on the nematic liquid crystal included in the liquid crystal composition of one embodiment of the present invention, and examples thereof include a biphenyl-based compound, a terphenyl-based compound, a phenylcyclohexyl-based compound, a biphenylcyclohexyl-based compound, a phenylbicyclohexyl-based compound, a phenyl benzoate-based compound, a phenyl cyclohexylbenzoate-based compound, a phenyl benzoate-based compound, a phenyl bicyclohexylcarboxylate-based compound, an azomethine-based compound, an azo-based compound, an azoxy-based compound, a stilbene-based compound, a bicyclohexyl-based compound, a phenylpyrimidine-based compound, a biphenylpyrimidine-based compound, a pyrimidine-based compound, and a diphenylacetylene-based compound.

Note that the liquid crystal composition of this embodiment includes a nematic liquid crystal and the dioxolane derivative represented by General Formula (G1), (G2), (G3), or (G4), and may be a liquid crystal composition which exhibits a blue phase. A blue phase is optically isotropic and thus has no viewing angle dependence. Consequently, an alignment film is not necessarily formed; thus, image quality of a display device can be improved and a manufacturing cost can be reduced.

In the case where the liquid crystal composition described in this embodiment exhibits a blue phase, it is preferable that a polymerizable monomer be added to a liquid crystal composition and polymer stabilization treatment be performed in order to broaden the temperature range within which a blue phase is exhibited in a liquid crystal display device. As the polymerizable monomer, for example, a thermopolymerizable (thermosetting) oligomers which can be polymerized by heat, a photopolymerizable (photocurable) oligomers which can be polymerized by light, and the like can be used in addition to vinyl monomers.

The polymerizable vinyl monomer may be a monofunctional monomer such as an acrylate or a methacrylate; a polyfunctional monomer such as a diacrylate, a triacrylate, a dimethacrylate, or a trimethacrylate; or a mixture thereof. The polymerizable monomer may have liquid crystallinity, non-liquid crystallinity, or a mixture of them.

A polymerization initiator may be added to the liquid crystal composition when the polymer stabilization treatment is carried out. As the polymerization initiator, a radical polymerization initiator which generates radicals by light irradiation or heating, an acid generator which generates an acid by light irradiation or heating, or a base generator which generates a base by light irradiation or heating may be used.

For example, polymer stabilization treatment can be performed in such a manner that a polymerizable monomer and a photopolymerization initiator are added to the liquid crystal composition and the liquid crystal composition is irradiated with light This polymer stabilization treatment may be performed in a state that a liquid crystal composition exhibits an isotropic phase or in a state that a liquid crystal composition exhibits a blue phase under the temperature control. A temperature at which the phase changes from a blue phase to an isotropic phase when the temperature is increased, or a temperature at which the phase changes from an isotropic phase to a blue phase when the temperature is decreased is referred to as the phase transition temperature between a blue phase and an isotropic phase. For example, the polymer stabilization treatment can be performed in the following manner: after a liquid crystal composition to which a photopolymerizable monomer is added is heated to exhibit an isotropic phase, the temperature of the liquid crystal composition is gradually decreased until the phase changes to a blue phase, and then, light irradiation is performed while the temperature at which a blue phase is exhibited is kept.

Figure 1B:
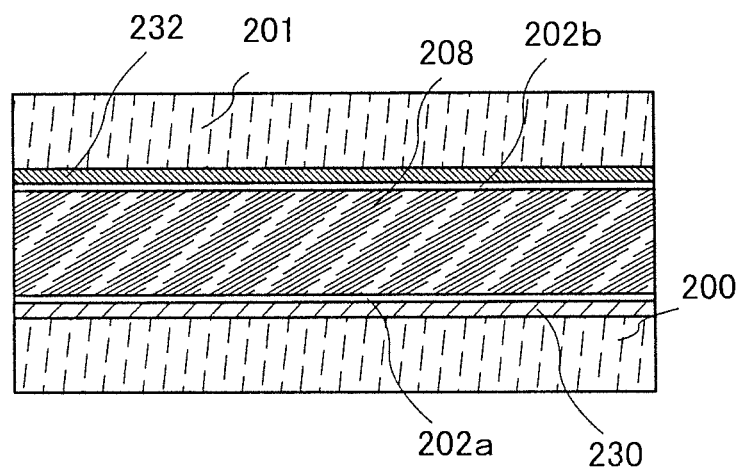

FIGS. 1A and 1B illustrate examples of a liquid crystal element and a liquid crystal display device of embodiments of the present invention.

A liquid crystal element in this embodiment includes, between a pair of electrode layers (a pixel electrode layer 230 and a common electrode layer 232 to be applied with different potentials), a liquid crystal composition 208 which includes the dioxolane derivative represented by General Formula (G1), (G2), (G3), or (G4) in Embodiments 1 to 3 and a nematic liquid crystal. Note that the liquid crystal composition 208 may include an organic resin.

FIGS. 1A and 1B each illustrate a liquid crystal display element or a liquid crystal display device in which the liquid crystal composition 208 which includes a nematic liquid crystal and the dioxolane derivative represented by General Formula (G1), (G2), (G3), or (G4) is provided between a first substrate 200 and a second substrate 201. A difference between the liquid crystal element and the liquid crystal display device in FIG. 1A and those in FIG. 1B is positions of the pixel electrode layer 230 and the common electrode layer 232 with respect to the liquid crystal composition 208.

In the liquid crystal element and the liquid crystal display device illustrated in FIG. 1A, the pixel electrode layer 230 and the common electrode layer 232 are each provided between the first substrate 200 and the liquid crystal composition 208 and adjacent to each other. The structure of FIG. 1A can be driven so that the gray scale is controlled by generating an electric field substantially parallel (i.e., in a lateral direction) to a substrate to orientate liquid crystal molecules in a plane parallel to the substrate.

Note that a liquid crystal composition which includes a nematic liquid crystal and the dioxolane derivative of one embodiment of the present invention, which is represented by General Formula (G1), (G2), (G3), or (G4), may be a liquid crystal composition exhibiting a blue phase. The structure illustrated in FIG. 1A is preferable in the case where a liquid crystal composition exhibiting a blue phase is used as the liquid crystal composition 208. The liquid crystal composition exhibiting a blue phase is capable of quick response. Thus, a high-performance liquid crystal element and a high-performance liquid crystal display device can be provided. Additionally, because the orientation control is conducted with the IPS mode, it is possible to obtain a wide viewing angle compared with the traditional devices in which the orientation is controlled by the TN mode or VA mode.

For example, the quick response of such a liquid crystal composition exhibiting a blue phase allows the application of a successive additive color mixing method (a field sequential method) or a three-dimensional display method. In the successive additive color mixing method, light-emitting diodes (LEDs) of RGB or the like are arranged in a backlight unit and color display is performed by time division. In the three-dimensional display method, a shutter glasses system is used in which images for a right eye and images for a left eye are alternately viewed by time division.

In the liquid crystal element and the liquid crystal display device illustrated in FIG. 1B, the pixel electrode layer 230 and the common electrode layer 232 are provided on the first substrate 200 side and the second substrate 201 side, respectively, with the liquid crystal composition 208 interposed therebetween. With the structure of FIG. 1B, the gray scale can be controlled by generating an electric field substantially perpendicular to a substrate to orientate liquid crystal molecules in a plane perpendicular to the substrate. An alignment film 202a may be provided between the liquid crystal composition 208 and the pixel electrode layer 230 and an alignment film 202b may be provided between the liquid crystal composition 208 and the common electrode layer 232. A liquid crystal composition which includes a nematic liquid crystal and the dioxolane derivative of one embodiment of the present invention can be used for liquid crystal elements with a variety of structures and liquid crystal display devices in a variety of display modes (e.g., a TN mode, a cholesteric liquid crystal mode, or a VA mode).

Although not illustrated in FIGS. 1A and 1B, an optical film such as a polarizing plate, a retardation plate, an anti-reflection film, or the like may be provided as appropriate. For example, circular polarization by the polarizing plate and the retardation plate may be used. In addition, a backlight or the like can be used as a light source.

In this specification, the first substrate can be provided with a semiconductor element (e.g., a transistor) or a pixel electrode layer. In this case, the first substrate is referred to as an element substrate, and the second substrate which faces the element substrate with a liquid crystal composition interposed therebetween is referred to as a counter substrate.

As a liquid crystal display device of one embodiment of the present invention, a transmissive liquid crystal display device in which display is performed by transmission of light from a light source, a reflective liquid crystal display device in which display is performed by reflection of incident light, or a transflective liquid crystal display device in which a transmissive type and a reflective type are combined can be provided.

In the case of the transmissive liquid crystal display device, a pixel electrode layer and a common electrode layer, which are provided in a light-transmitting pixel region, as well as a first substrate, a second substrate, and other components such as an insulating film and a conductive film have a light-transmitting property. In the liquid crystal display device having the structure illustrated in FIG. 1A, it is preferable that the pixel electrode layer and the common electrode layer have a light-transmitting property; however, if an opening is provided, a non-light-transmitting material such as a metal film may be used depending on the shape.

On the other hand, in the case of the reflective liquid crystal display device, a reflective component which reflects light transmitted through the liquid crystal composition (e.g., a reflective film or substrate) may be provided on the side opposite to the viewing side of the liquid crystal composition. Therefore, a substrate, an insulating film, and a conductive film which are provided between the viewing side and the reflective component and through which light is transmitted have a light-transmitting property. Note that in this specification, a light-transmitting property refers to a property of transmitting at least visible light. In the liquid crystal display device having the structure illustrated in FIG. 1B, the pixel electrode layer or the common electrode layer on the side opposite to the viewing side may have a light-reflecting property so that it can be used as a reflective component.

The pixel electrode layer 230 and the common electrode layer 232 may be formed with the use of one or more of the following: indium tin oxide (ITO); a conductive material in which zinc oxide (ZnO) is mixed into indium oxide; a conductive material in which silicon oxide ($SiO_2$) is mixed into indium oxide; indium oxide containing tungsten oxide; indium zinc oxide containing tungsten oxide; indium oxide containing titanium oxide; indium tin oxide containing titanium oxide; graphene; metals such as tungsten (W), molybdenum (Mo), zirconium (Zr), hafnium (Hf), vanadium (V), niobium (Nb), tantalum (Ta), chromium (Cr), cobalt (Co), nickel (Ni), titanium (Ti), platinum (Pt), aluminum (Al), copper (Cu), and silver (Ag); alloys thereof; and metal nitrides thereof.

As the first substrate 200 and the second substrate 201, a glass substrate of barium borosilicate glass, aluminoborosilicate glass, or the like, a quartz substrate, a plastic substrate, or the like can be used. Note that in the case of the reflective liquid crystal display device, a metal substrate such as an aluminum substrate or a stainless steel substrate may be used as a substrate on the side opposite to the viewing side.

With the use of the dioxolane derivative represented by General Formula (G1), (G2), (G3), or (G4) as a chiral material in a liquid crystal composition, the amount of chiral material added to the liquid crystal composition can be small. Therefore, by using the liquid crystal composition, a liquid crystal element or liquid crystal display device that can be driven at a low driving voltage can be provided, and a reduction in power consumption of the liquid crystal display device can be achieved.

Furthermore, the liquid crystal composition of one embodiment of the present invention can exhibit a blue phase and respond quickly. Therefore, by using the liquid crystal composition, a high-performance liquid crystal element or liquid crystal display device can be provided.

The structures, methods, and the like described in this embodiment can be combined as appropriate with any of the structures, methods, and the like described in the other embodiments.

(Embodiment 5)

As a liquid crystal display device according to one embodiment of the present invention, a passive matrix liquid crystal display device and an active matrix liquid crystal display device can be provided. In this embodiment, an example of an active matrix liquid crystal display device will be described with reference to FIGS. 2A and 2B and FIGS. 3A to 3D.

Figure 2A:
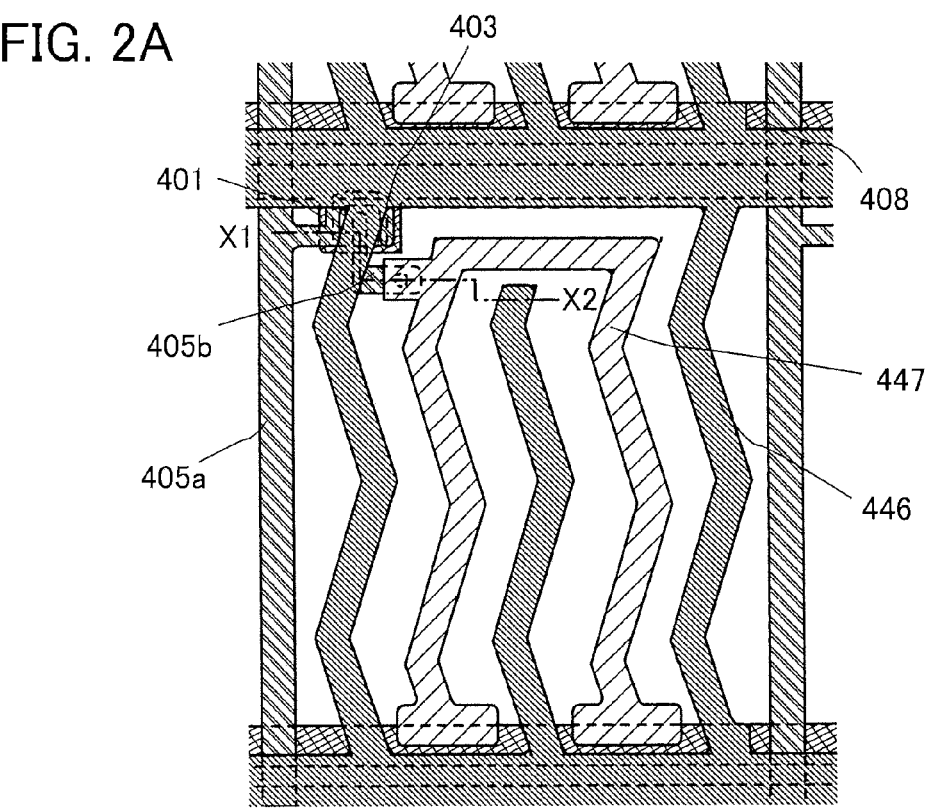
FIGS. 2A and 2B illustrate one mode of a liquid crystal display device.
Figure 2B:
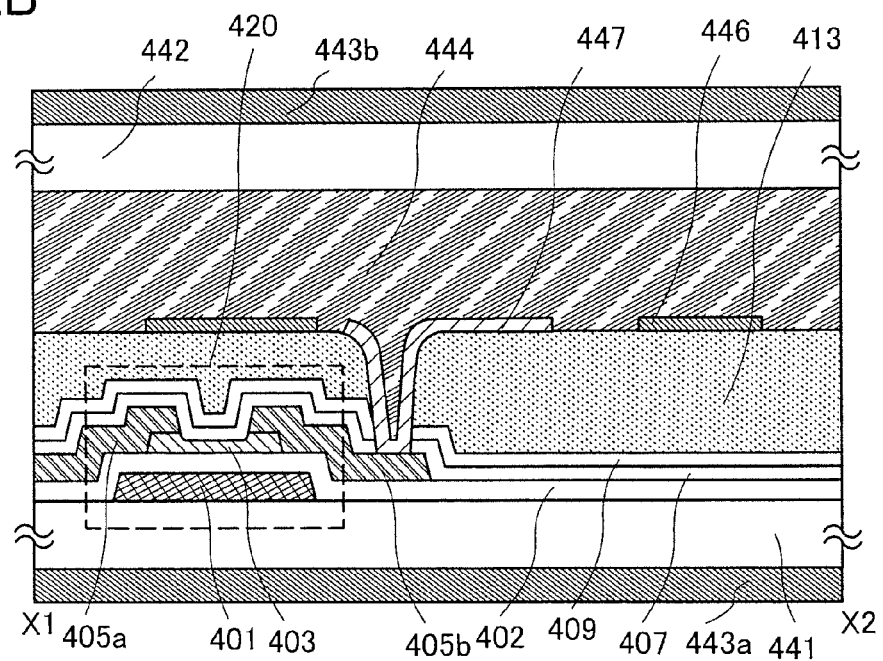

FIG. 2A is a plan view of the liquid crystal display device and illustrates one pixel. FIG. 2B is a cross-sectional view taken along line X1-X2 in FIG. 2A.

In FIG. 2A, a plurality of source wiring layers (including a wiring layer 405a) is arranged so as to be parallel to (extend in the vertical direction in the drawing) and apart from each other. A plurality of gate wiring layers (including a gate electrode layer 401) is provided to extend in a direction substantially perpendicular to the source wiring layers (the horizontal direction in the drawing) and to be apart from each other. Common wiring layers 408 are provided adjacent to the respective plurality of gate wiring layers and extend in a direction substantially parallel to the gate wiring layers, that is, in a direction substantially perpendicular to the source wiring layers (the horizontal direction in the drawing). A roughly rectangular space is surrounded by the source wiring layers, the common wiring layers 408, and the gate wiring layers. In this space, a pixel electrode layer and a common electrode layer of the liquid crystal display device are provided. A transistor 420 for driving the pixel electrode layer is provided at an upper left corner of the drawing. A plurality of pixel electrode layers and a plurality of transistors are arranged in matrix.

In the liquid crystal display device of FIGS. 2A and 2B, a first electrode layer 447 which is electrically connected to the transistor 420 serves as a pixel electrode layer, while a second electrode layer 446 which is electrically connected to the common wiring layer 408 serves as a common electrode layer. Note that a capacitor is formed by the first electrode layer and the common wiring layer. Although the common electrode layer can operate in a floating state (an electrically isolated state), the potential of the common electrode layer may be set to a fixed potential, preferably to a potential around a common potential (an intermediate potential of an image signal which is transmitted as data) in such a level as not to generate flickers.

It is possible to employ a driving method in which the gray scale is controlled by generating an electric field substantially parallel (i.e., in a lateral direction) to a substrate to orientate liquid crystal molecules in a plane parallel to the substrate. For such a method, an electrode structure used in an IPS mode as illustrated in FIGS. 2A and 2B and FIGS. 3A to 3D can be employed.

In a lateral electric field mode such as an IPS mode, a first electrode layer (e.g., a pixel electrode layer a voltage of which is controlled in each pixel) and a second electrode layer (e.g., a common electrode layer to which a common voltage is supplied in all pixels), each of which has an opening pattern, are located below a liquid crystal composition. Therefore, the first electrode layer 447 and the second electrode layer 446, one of which is a pixel electrode layer and the other is a common electrode layer, are formed over a first substrate 441, and at least one of the first electrode layer and the second electrode layer is formed over an insulating film. The first electrode layer 447 and the second electrode layer 446 have a variety of shapes. For example, they can have an opening portion, a bent portion, branched portion, or a comb-shaped portion. In order to generate an electric field substantially parallel to a substrate between the first electrode layer 447 and the second electrode layer 446, an arrangement is avoided in which they have the same shape and completely overlap with each other.

The first electrode layer 447 and the second electrode layer 446 may have a structure applicable in an FFS mode.

In a lateral electric field mode such as an FFS mode, a first electrode layer (e.g., a pixel electrode layer a voltage of which is controlled in each pixel) having an opening pattern is located below a liquid crystal composition, and further, a second electrode layer (e.g., a common electrode layer to which a common voltage is supplied in all pixels) having a board shape is located below the opening pattern. In this case, the first electrode layer and the second electrode layer, one of which is a pixel electrode layer and the other of which is a common electrode layer, are formed over the first substrate 441, and the pixel electrode layer and the common electrode layer are stacked with an insulating film (or an interlayer insulating layer) interposed therebetween. One of the pixel electrode layer and the common electrode layer is formed below the insulating film (or the interlayer insulating layer) and has a board shape, whereas the other is formed above the insulating film (or the interlayer insulating layer) and has various shapes including an opening portion, a bent portion, a branched portion, or a comb-like portion. In order to generate an electric field slant to a substrate between the first electrode layer 447 and the second electrode layer 446, an arrangement is avoided in which they have the same shape and completely overlap with each other.

The liquid crystal composition including the dioxolane derivative represented by General Formula (G1), (G2), (G3), or (G4) shown in Embodiments 1 to 3 and a nematic liquid crystal is used as a liquid crystal composition 444. The liquid crystal composition 444 may further include an organic resin. In this embodiment, the liquid crystal composition 444 includes the dioxolane derivative represented by General Formula (G1), (G2), (G3), or (G4) and a nematic liquid crystal and exhibits a blue phase. The liquid crystal composition 444 is formed by performing the polymer stabilization treatment in a state that liquid crystal composition 444 exists in a blue phase.

With a lateral electric field generated between the first electrode layer 447 and the second electrode layer 446, liquid crystal of the liquid crystal composition 444 is controlled. Hence, a wide viewing angle can be obtained.

Figure 3A:
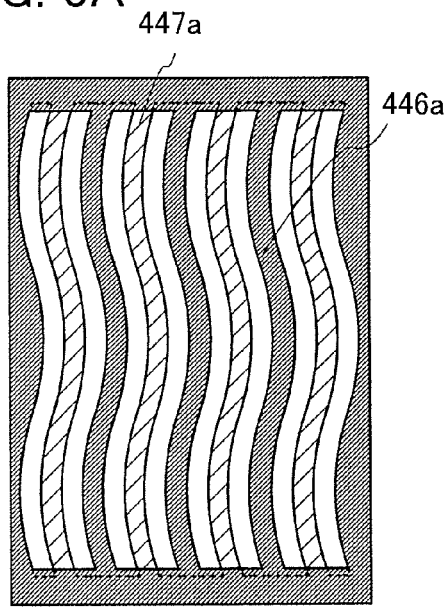
FIGS. 3A to 3D each illustrate one mode of an electrode structure of a liquid crystal display device.
Figure 3B:
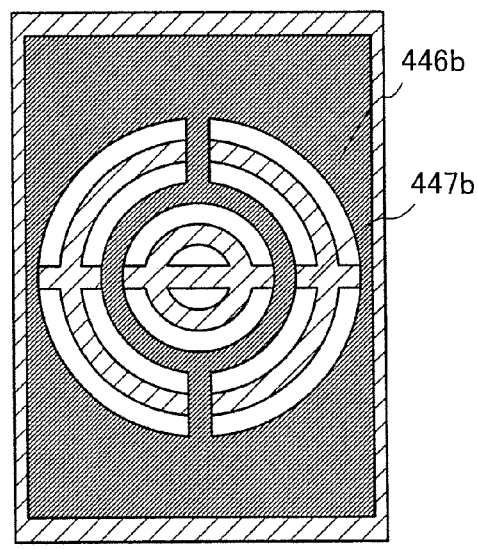
Figure 3C:
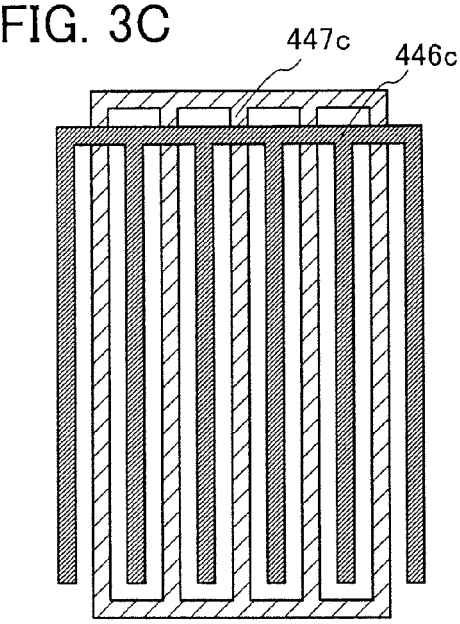
Figure 3D:
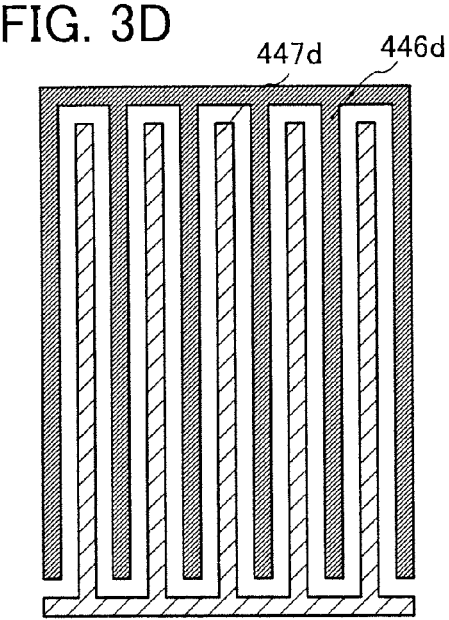

FIGS. 3A to 3D show other examples of the first electrode layer 447 and the second electrode layer 446. As illustrated in top views of FIGS. 3A to 3D, first electrode layers 447a to 447d and second electrode layers 446a to 446d are staggered. In FIG. 3A, the first electrode layer 447a and the second electrode layer 446a have an opening with a wave-like shape. In FIG. 3B, the first electrode layer 447b and the second electrode layer 446b have a shape with concentric circular openings. In FIG. 3C, the first electrode layer 447c and the second electrode layer 446c have a comb-shape and partially overlap with each other. In FIG. 3D, the first electrode layer 447d and the second electrode layer 446d have a comb-shape in which the electrode layers are engaged with each other. In the case where the first electrode layers 447a, 447b, and 447c overlap with the second electrode layers 446a, 446b, and 446c, respectively, as illustrated in FIGS. 3A to 3C, an insulating film is formed between the first electrode layer 447 and the second electrode layer 446 so that the first electrode layer 447 and the second electrode layer 446 are formed over different films.

Since the second electrode layer 446 has an opening pattern, they are illustrated as a divided plurality of electrode layers in the cross-sectional view of FIG. 2B. The same applies to the other drawings of this specification.

The transistor 420 is an inverted staggered thin film transistor in which the gate electrode layer 401, a gate insulating layer 402, a semiconductor layer 403, and wiring layers 405a and 405b which function as a source electrode layer and a drain electrode layer are formed over the first substrate 441 which has an insulating surface.

There is no particular limitation on a structure of a transistor that can be used for a liquid crystal display device disclosed in this specification. For example, a staggered type or a planar type having a top-gate structure or a bottom-gate structure can be employed. The transistor may have a single-gate structure in which one channel formation region is formed, a double-gate structure in which two channel formation regions are formed, or a triple-gate structure in which three channel formation regions are formed. Alternatively, the transistor may have a dual gate structure including two gate electrode layers positioned over and below a channel region with a gate insulating layer provided therebetween.

An insulating film 407 that is in contact with the semiconductor layer 403, and an insulating film 409 are provided to cover the transistor 420. An interlayer film 413 is stacked over the insulating film 409.

The first substrate 441 and a second substrate 442 that is a counter substrate are firmly attached to each other with a sealant with the liquid crystal composition 444 interposed therebetween. The liquid crystal composition 444 can be formed by a dispenser method (a dropping method), or an injection method by which a liquid crystal composition 444 is injected using capillary action or the like after the first substrate 441 is attached to the second substrate 442.

As the sealant, typically, a visible light curable resin, a UV curable resin, or a thermosetting resin is preferably used. Typically, an acrylic resin, an epoxy resin, an amine resin, or the like can be used. Further, a filler or a coupling agent may be included in the sealant.

In this embodiment, a polarizing plate 443a is provided on the outer side (on the side opposite to the liquid crystal composition 444) of the first substrate 441, and a polarizing plate 443b is provided on the outer side (on the side opposite to the liquid crystal composition 444) of the second substrate 442. In addition to the polarizing plates, an optical film such as a retardation plate or an anti-reflection film may be provided. For example, circular polarization plate formed by the polarizing plate and the retardation plate may be used. Through the above-described process, a liquid crystal display device is completed.

Although not illustrated, a backlight, a sidelight, or the like may be used as a light source. Light source is provided so that light which passes through the first substrate 441 (element substrate) and the second substrate 442 and reach the viewing side.

The first electrode layer 447 and the second electrode layer 446 can be formed using a light-transmitting conductive material such as indium oxide containing tungsten oxide, indium zinc oxide containing tungsten oxide, indium oxide containing titanium oxide, indium tin oxide containing titanium oxide, ITO, indium zinc oxide, indium tin oxide to which silicon oxide is added, or graphene.

The first electrode layer 447 and the second electrode layer 446 can be formed using one or more kinds selected from a metal such as tungsten (W), molybdenum (Mo), zirconium (Zr), hafnium (Hf), vanadium (V), niobium (Nb), tantalum (Ta), chromium (Cr), cobalt (Co), nickel (Ni), titanium (Ti), platinum (Pt), aluminum (Al), copper (Cu), or silver (Ag); an alloy thereof; and a nitride thereof.

A conductive composition containing a conductive polymer can be used to form the first electrode layer 447 and the second electrode layer 446. As the conductive polymer, what is called a π-conjugated conductive polymer can be used. Examples include polyaniline or a derivative thereof, polypyrrole or a derivative thereof, polythiophene or a derivative thereof, and a copolymer of two or more of aniline, pyrrole, and thiophene or a derivative thereof.

An insulating film serving as a base film may be provided between the first substrate 441 and the gate electrode layer 401. The gate electrode layer 401 can be formed to have a single-layer or layered structure using a metal such as molybdenum, titanium, chromium, tantalum, tungsten, aluminum, copper, neodymium, or scandium, or an alloy which contains any of these metals as its main component. A semiconductor film which is doped with an impurity element such as phosphorus and is typified by a polycrystalline silicon film, or a silicide film of nickel silicide or the like can also be used as the gate electrode layer 401. By using a light-blocking conductive film as the gate electrode layer 401, light from a backlight (light incident from the first substrate 441) can be prevented from entering the semiconductor layer 403.

For example, the gate insulating layer 402 can be formed with the use of a silicon oxide film, a gallium oxide film, an aluminum oxide film, a silicon nitride film, a silicon oxynitride film, an aluminum oxynitride film, or a silicon nitride oxide film. Alternatively, a high-k material such as hafnium oxide, yttrium oxide, lanthanum oxide, hafnium silicate, hafnium aluminate, hafnium silicate to which nitrogen is added, or hafnium aluminate to which nitrogen is added may be used as a material for the gate insulating layer 402. The use of such a high-k material enables a reduction in gate leakage current.

Note that the silicon oxide film can be formed by a CVD method in which an organosilane gas is used. As an organosilane gas, a silicon-containing compound such as tetraethoxysilane (TEOS) (chemical formula: $Si(OC_2H_5)_4$), tetramethylsilane (TMS) (chemical formula: $Si(CH_3)_4$), tetramethylcyclotetrasiloxane, octamethylcyclotetrasiloxane (OMCTS), hexamethyldisilazane (HMDS), triethoxysilane (chemical formula: $SiH(OC_2H_5)_3$), or trisdimethylaminosilane (chemical formula: $SiH(N(CH_3)_2)_3$) can be used. Note that the gate insulating layer 402 may have a single layer structure or a layered structure.

A material of the semiconductor layer 403 is not limited to a particular material and may be determined in accordance with characteristics needed for the transistor 420, as appropriate. Examples of a material that can be used for the semiconductor layer 403 will be described.

The semiconductor layer 403 can be formed using the following material: an amorphous semiconductor formed by a chemical vapor deposition method using a semiconductor source gas typified by silane or germane or by a physical vapor deposition method such as sputtering; a polycrystalline semiconductor formed by crystallizing the amorphous semiconductor with the use of light energy or thermal energy; a microcrystalline semiconductor in which a minute crystalline phase and an amorphous phase coexist; or the like.

A typical example of an amorphous semiconductor is hydrogenated amorphous silicon, while a typical example of a crystalline semiconductor is polysilicon and the like. Polysilicon (polycrystalline silicon) includes what is called high-temperature polysilicon that contains, as its main component, polysilicon formed at a process temperature of 800° C. or higher, what is called low-temperature polysilicon that contains, as its main component, polysilicon formed at a process temperature of 600° C. or lower, and polysilicon formed by crystallizing amorphous silicon by using an element that promotes crystallization, or the like. Needless to say, as described above, a microcrystalline semiconductor or a semiconductor which includes a crystal phase in part of a semiconductor layer can also be used.

Alternatively, an oxide semiconductor may be used. In that case, any of the following can be used for example: indium oxide, tin oxide, zinc oxide, an In—Zn-based oxide, a Sn—Zn-based oxide, an Al—Zn-based oxide, a Zn—Mg-based oxide, a Sn—Mg-based oxide, an In—Mg-based oxide, an In—Ga-based oxide, an In—Ga—Zn-based oxide (also referred to as IGZO), an In—Al—Zn-based oxide, an In—Sn—Zn-based oxide, a Sn—Ga—Zn-based oxide, an Al—Ga—Zn-based oxide, a Sn—Al—Zn-based oxide, an In—Hf—Zn-based oxide, an In—La—Zn-based oxide, an In—Ce—Zn-based oxide, an In—Pr—Zn-based oxide, an In—Nd—Zn-based oxide, an In—Sm—Zn-based oxide, an In—Eu—Zn-based oxide, an In—Gd—Zn-based oxide, an In—Tb—Zn-based oxide, an In—Dy—Zn-based oxide, an In—Ho—Zn-based oxide, an In—Er—Zn-based oxide, an In—Tm—Zn-based oxide, an In—Yb—Zn-based oxide, an In—Lu—Zn-based oxide, an In—Sn—Ga—Zn-based oxide, an In—Hf—Ga—Zn-based oxide, an In—Al—Ga—Zn-based oxide, an In—Sn—Al—Zn-based oxide, an In—Sn—Hf—Zn-based oxide, and an In—Hf—Al—Zn-based oxide. In addition, any of the above oxide semiconductors may contain an element other than In, Ga, Sn, and Zn, for example, $SiO_2$.

Here, for example, an In—Ga—Zn—O-based oxide semiconductor means an oxide semiconductor containing indium (In), gallium (Ga), and zinc (Zn), and there is no limitation on the composition thereof.

For the oxide semiconductor layer, a thin film expressed by a chemical formula $InMO_3(ZnO)_m$ (m>0) can be used. Here, M denotes one or more metal elements selected from Ga, Al, Mn, and Co. For example, M may be Ga, Ga and Al, Ga and Mn, Ga and Co, or the like.

As the oxide semiconductor layer, a CAAC-OS (c-axis aligned crystalline oxide semiconductor) film can be used, for example.

The CAAC-OS film is one of oxide semiconductor films having a plurality of c-axis aligned crystal parts.

As a material of the wiring layers 405a and 405b serving as source and drain electrode layers, an element selected from Al, Cr, Ta, Ti, Mo, and W; an alloy containing any of the above elements as its component; and the like can be given. Further, in the case where heat treatment is performed, the conductive film preferably has heat resistance against the heat treatment.

The gate insulating layer 402, the semiconductor layer 403, and the wiring layers 405a and 405b serving as source and drain electrode layers may be successively formed without being exposed to the air. When the gate insulating layer 402, the semiconductor layer 403, and the wiring layers 405a and 405b are formed successively without being exposed to the air, an interface between the layers can be formed without being contaminated with atmospheric components or impurity elements included in the air. Thus, variations in characteristics of transistors can be reduced.

Note that the semiconductor layer 403 is partly etched so as to have a groove (a depression portion).

As the insulating film 407 and the insulating film 409 which cover the transistor 420, an inorganic insulating film or an organic insulating film formed by a dry method or a wet method can be used. For example, it is possible to use a silicon nitride film, a silicon oxide film, a silicon oxynitride film, an aluminum oxide film, or a tantalum oxide film, which is formed by a CVD method, a sputtering method, or the like. It is also possible to use a low-dielectric constant material (a low-k material), a siloxane-based resin, PSG (phosphosilicate glass), BPSG (borophosphosilicate glass), or the like. A gallium oxide film may also be used as the insulating film 407. Alternatively, an organic material such as a polyimide, an acrylic resin, a benzocyclobutene-based resin, a polyamide, or an epoxy resin can be used.

Note that the siloxane-based resin is a resin including a Si—O—Si bond formed using a siloxane-based material as a starting material. The siloxane-based resin may include as a substituent an organic group (e.g., an alkyl group or an aryl group) or fluorine. In addition, the organic group may include fluorine. A siloxane-based resin is applied by a coating method and baked; thus, the insulating film 407 can be formed.

Alternatively, the insulating film 407 and the insulating film 409 may be formed by stacking a plurality of insulating films formed using any of these materials. For example, the insulating film 407 and the insulating film 409 may each have such a structure that an organic resin film is stacked over an inorganic insulating film.

In the above manner, by using the liquid crystal composition including the dioxolane derivative represented by General Formula (G1), (G2), (G3), or (G4) and a nematic liquid crystal, a liquid crystal element or liquid crystal display device that can be driven at a low driving voltage can be provided. Thus, a reduction in power consumption of the liquid crystal display device can be achieved.

Further, the liquid crystal composition including the dioxolane derivative represented by General Formula (G1), (G2), (G3), or (G4) and a nematic liquid crystal and exhibiting a blue phase is capable of quick response. Thus, by using the liquid crystal composition, a high-performance liquid crystal display device can be provided.

The structures, methods, and the like described in this embodiment can be combined as appropriate with any of the structures, methods, and the like described in the other embodiments.

(Embodiment 6)

A liquid crystal display device having a display function can be manufactured by using transistors in a pixel portion and further in a driver circuit. Further, part or the whole of the driver circuit can be formed over the same substrate as the pixel portion, whereby a system-on-panel can be obtained.

The liquid crystal display device includes a liquid crystal element (also referred to as a liquid crystal display element) as a display element.

A liquid crystal display module includes a panel in which a display element is sealed, and a component in which an IC or the like including a controller is mounted to the panel. One embodiment of the present invention also relates to an element substrate, which corresponds to one mode before the display element is completed in a manufacturing process of the liquid crystal display device, and the element substrate is provided with a means for supplying current to the display element in each of a plurality of pixels. Specifically, the element substrate may be in a state in which only a pixel electrode of the display element is provided, a state after formation of a conductive film to be a pixel electrode and before etching of the conductive film to form the pixel electrode, or any other states.

Note that a liquid crystal display device in this specification means an image display device or a light source (including a lighting device). Furthermore, a liquid crystal display device also refers to all the following display modules in some cases: a display module in which a connector, for example, a flexible printed circuit (FPC) or a tape carrier package (TCP) is attached to a liquid crystal display device, a display module in which a printed wiring board is provided at an end of a TCP, and a display module in which an integrated circuit (IC) is directly mounted on a liquid crystal display device by a chip on glass (COG) method.

The display module may include a touch sensor panel provided over the liquid crystal display device. Note that a panel for a touch sensor is not necessarily provided separately; the display module may include an in-cell or on-cell touch sensor panel in which, for example, an electrode for a touch sensor is provided on a counter substrate of the liquid crystal display device. Furthermore, the display module may include a backlight, an optical film (a polarizing plate, a retardation plate, or a luminance increasing film), and the like.

Figure 4B:
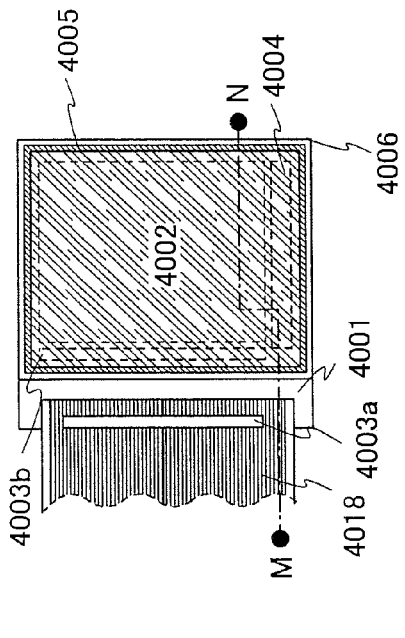
Figure 4B:
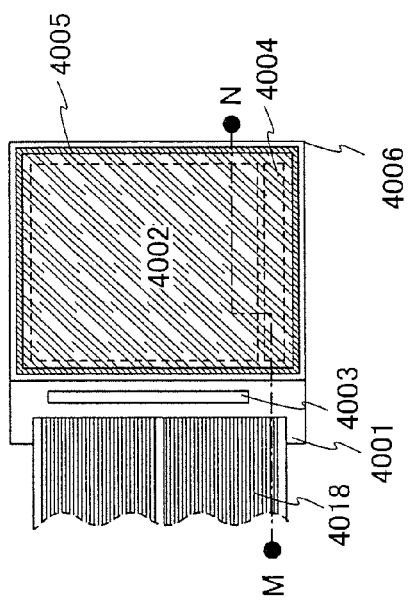
Figure 4B:
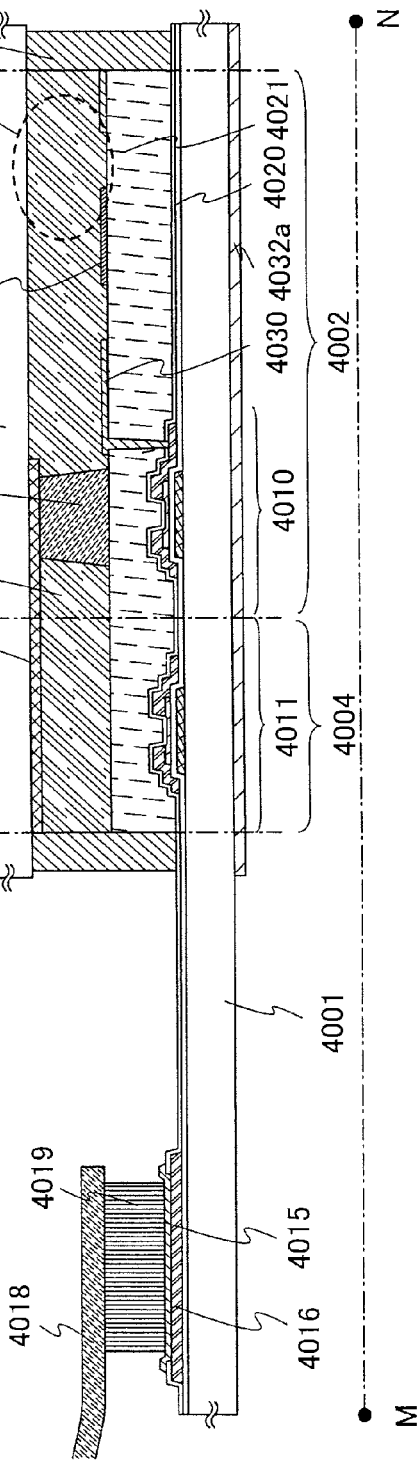

The appearance and a cross section of a liquid crystal display panel (a display module) which corresponds to a liquid crystal display device of one embodiment of the present invention will be described with reference to FIGS. 4A1, 4A2 and 4B. FIGS. 4A1 and 4A2 are top views of a panel in which transistors 4010 and 4011 and a liquid crystal element 4013 which are formed over a first substrate 4001 are sealed between the first substrate 4001 and a second substrate 4006 with a sealant 4005. FIG. 4B is a cross-sectional view taken along M-N of FIGS. 4A1 and 4A2.

The sealant 4005 is provided so as to surround a pixel portion 4002 and a scan line driver circuit 4004 which are provided over the first substrate 4001. The second substrate 4006 is provided over the pixel portion 4002 and the scan line driver circuit 4004. Thus, the pixel portion 4002 and the scan line driver circuit 4004 are sealed together with a liquid crystal composition 4008, by the first substrate 4001, the sealant 4005, and the second substrate 4006.

In FIG. 4A1, a signal line driver circuit 4003 that is formed using a single crystal semiconductor film or a polycrystalline semiconductor film over a substrate separately prepared is mounted in a region that is different from the region surrounded by the sealant 4005 over the first substrate 4001. FIG. 4A2 illustrates an example in which part of a signal line driver circuit is formed with the use of a transistor which is provided over the first substrate 4001. A signal line driver circuit 4003b is formed over the first substrate 4001 and a signal line driver circuit 4003a which is formed using a single crystal semiconductor film or a polycrystalline semiconductor film is mounted over a substrate separately prepared.

Note that there is no particular limitation on the connection method of a driver circuit which is separately formed, and a COG method, a wire bonding method, a TAB method, or the like can be used. FIG. 4A1 illustrates an example of mounting the signal line driver circuit 4003 by a COG method, and FIG. 4A2 illustrates an example of mounting the signal line driver circuit 4003 by a TAB method.

The pixel portion 4002 and the scan line driver circuit 4004 provided over the first substrate 4001 include a plurality of transistors. FIG. 4B illustrates the transistor 4010 included in the pixel portion 4002 and the transistor 4011 included in the scan line driver circuit 4004, as an example. An insulating layer 4020 and an interlayer film 4021 are provided over the transistors 4010 and 4011.

Any of the transistors shown in Embodiment 5 can be used as the transistors 4010 and 4011.

Further, a conductive layer may be provided over the interlayer film 4021 or the insulating layer 4020 so as to overlap with a channel formation region of a semiconductor layer of the transistor 4011 for the driver circuit. The conductive layer may have the same potential as or a potential different from that of a gate electrode layer of the transistor 4011 and can function as a second gate electrode layer. Further, the potential of the conductive layer may be GND, or the conductive layer may be in a floating state.

A pixel electrode layer 4030 and a common electrode layer 4031 are provided over the interlayer film 4021, and the pixel electrode layer 4030 is electrically connected to the transistor 4010. The liquid crystal element 4013 includes the pixel electrode layer 4030, the common electrode layer 4031, and the liquid crystal composition 4008. Note that a polarizing plate 4032a and a polarizing plate 4032b are provided on the outer sides of the first substrate 4001 and the second substrate 4006, respectively.

A liquid crystal composition including the dioxolane derivative represented by General Formula (G1), (G2), (G3) or (G4) shown in Embodiments 1 to 3 and a nematic liquid crystal is used as the liquid crystal composition 4008. The structures of the pixel electrode layer and the common electrode layer described in any of the above embodiments can be used for the pixel electrode layer 4030 and the common electrode layer 4031.

In this embodiment, the liquid crystal composition including the dioxolane derivative represented by General Formula (G1), (G2), (G3), or (G4) and a nematic liquid crystal and exhibiting a blue phase is used as the liquid crystal composition 4008. The liquid crystal composition 4008 is formed by performing the polymer stabilization treatment on the liquid crystal composition in the blue phase state. Therefore, in this embodiment, at least one of the pixel electrode layer 4030 and the common electrode layer 4031 has an opening portion or a comb-shape as illustrated in FIG. 1A described in Embodiment 4 or FIGS. 3A to 3D described in Embodiment 5.

With a lateral electric field applied between the pixel electrode layer 4030 and the common electrode layer 4031, liquid crystal of the liquid crystal composition 4008 is controlled. Hence, a wide viewing angle is obtained.

As the first substrate 4001 and the second substrate 4006, glass, plastic, or the like having a light-transmitting property can be used. As plastic, a fiber-reinforced plastics (FRP) plate, a poly(vinyl fluoride) (PVF) film, a polyester film, or an acrylic resin film can be used. In addition, a sheet with a structure in which an aluminum foil is interposed between PVF films or polyester films can be used.

A columnar spacer denoted by reference numeral 4035 is obtained by selective etching of an insulating film and is provided in order to control the thickness (a cell gap) of the liquid crystal composition 4008. Alternatively, a spherical spacer may also be used. In the liquid crystal display device including the liquid crystal composition 4008, the cell gap which is the thickness of the liquid crystal composition is preferably greater than or equal to 1 μm and less than or equal to 20 μm. In this specification, the thickness of a cell gap refers to the length (film thickness) of a thickest part of a liquid crystal composition.

Although FIGS. 4A1, 4A2, and 4B illustrate examples of transmissive liquid crystal display devices, one embodiment of the present invention can also be applied to a transflective liquid crystal display device and a reflective liquid crystal display device.

In the example of the liquid crystal display device illustrated in FIGS. 4A1, 4A2, and 4B, the polarizing plates are provided on the outer sides of the first substrate 4001 and the second substrate 4006; however, the polarizing plate may be provided on the inner side of the substrates. The position of the polarizing plate may be determined as appropriate depending on the material of the polarizing plate and conditions of the manufacturing process. Furthermore, a light-blocking layer serving as a black matrix may be provided.

A color filter layer or a light-blocking layer may be formed as part of the interlayer film 4021. In FIGS. 4A1, 4A2, and 4B, a light-blocking layer 4034 is provided on the second substrate 4006 side so as to cover the transistors 4010 and 4011. With the provision of the light-blocking layer 4034, the contrast can be increased and the transistors can be more highly stabilized.

In FIG. 4B, the transistors 4010 and 4011 may be, but is not necessarily, covered with the insulating layer 4020 which functions as a protective film of the transistors. Note that the protective film is provided to prevent entry of impurities such as organic substance, metal, or moisture existing in the air and is preferably a dense film. For example, the protective film may be formed by a sputtering method to have a single-layer structure or a layered structure including any of a silicon oxide film, a silicon nitride film, a silicon oxynitride film, a silicon nitride oxide film, an aluminum oxide film, an aluminum nitride film, an aluminum oxynitride film, and an aluminum nitride oxide film.

Furthermore, a light-transmitting insulating layer may be further formed as a planarizing insulating film.

For the pixel electrode layer 4030 and the common electrode layer 4031, a light-transmitting conductive material can be used.

A variety of signals and potentials are supplied to the signal line driver circuit 4003 which is separately formed, the scan line driver circuit 4004, or the pixel portion 4002 from an FPC 4018.

Since the transistor is easily broken by static electricity or the like, a protection circuit for protecting the driver circuits is preferably provided over the same substrate as a gate line or a source line. The protection circuit is preferably formed using a nonlinear element.

In FIGS. 4A1, 4A2, and 4B, a connection terminal electrode 4015 is formed using the same conductive film as that of the pixel electrode layer 4030, and a terminal electrode 4016 is formed using the same conductive film as that of source and drain electrode layers of the transistors 4010 and 4011.

The connection terminal electrode 4015 is electrically connected to a terminal included in the FPC 4018 via an anisotropic conductive film 4019.

Although FIGS. 4A1, 4A2, and 4B illustrate an example in which the signal line driver circuit 4003 is formed separately and mounted on the first substrate 4001, one embodiment of the present invention is not limited to this structure. The scan line driver circuit may be separately formed and then mounted, or only part of the signal line driver circuit or part of the scan line driver circuit may be separately formed and then mounted.

In the above manner, by using the liquid crystal composition including the dioxolane derivative represented by General Formula (G1), (G2), (G3), or (G4) and a nematic liquid crystal, the liquid crystal element or the liquid crystal display device can be driven at a low driving voltage. Thus, a reduction in power consumption of the liquid crystal display device can be achieved.

Further, the liquid crystal composition including the dioxolane derivative represented by General Formula (G1), (G2), (G3), or (G4) and a nematic liquid crystal and exhibiting a blue phase is capable of quick response. Thus, by using the liquid crystal composition for a liquid crystal display device, a high-performance liquid crystal display device can be provided.

The structures, methods, and the like described in this embodiment can be combined as appropriate with any of the structures, methods, and the like described in the other embodiments.

(Embodiment 7)

A liquid crystal display device disclosed in this specification can be used for a variety of electronic appliances (including game machines). Examples of such electronic appliances include a television set (also referred to as a television or a television receiver), a monitor of a computer or the like, a camera such as a digital camera or a digital video camera, a digital photo frame, a mobile phone handset (also referred to as a mobile phone or a mobile phone device), a portable game machine, a personal digital assistant, an audio reproducing device, a large game machine such as a pinball machine, and the like.

Figure 5A:
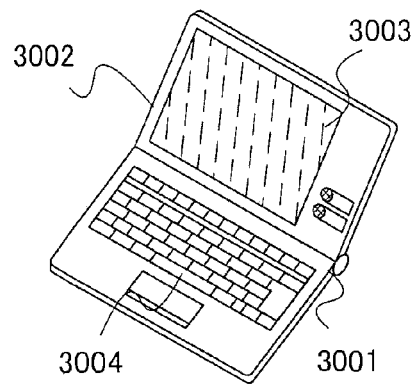
FIGS. 5A to 5F each illustrate an electronic appliance.

FIG. 5A illustrates a laptop personal computer, which includes a main body 3001, a housing 3002, a display portion 3003, a keyboard 3004, and the like. The liquid crystal display device described in any of the above embodiments is used for the display portion 3003, whereby a laptop personal computer with low power consumption can be provided.

Figure 5B:
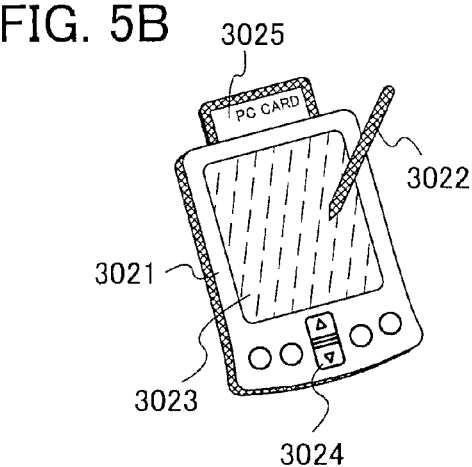

FIG. 5B illustrates a personal digital assistant (PDA), which includes a main body 3021 provided with a display portion 3023, an external interface 3025, operation buttons 3024, and the like. A stylus 3022 is included as an accessory for operation. The liquid crystal display device described in any of the above embodiments is used for the display portion 3023, whereby a personal digital assistant with low power consumption can be provided.

Figure 5C:
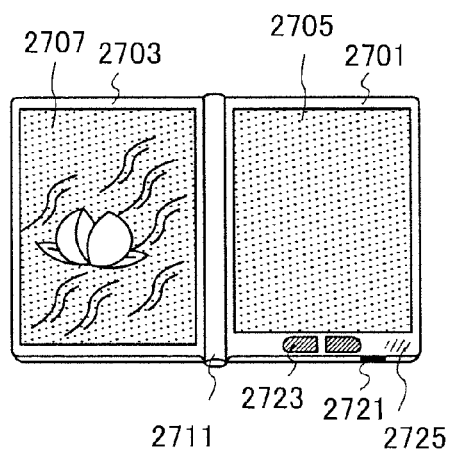

FIG. 5C illustrates an e-book reader, which includes two housings, a housing 2701 and a housing 2703. The housing 2701 and the housing 2703 are combined with a hinge 2711 so that the e-book reader can be opened and closed with the hinge 2711 as an axis. With such a structure, the e-book reader can operate like a paper book.

A display portion 2705 and a display portion 2707 are incorporated in the housing 2701 and the housing 2703, respectively. The display portion 2705 and the display portion 2707 may display one image or different images. In the structure where different images are displayed in the above display portions, for example, the right display portion (the display portion 2705 in FIG. 5C) can display text and the left display portion (the display portion 2707 in FIG. 5C) can display images. The liquid crystal display device described in any of the above embodiments is used for the display portions 2705 and 2707, whereby an e-book reader with low power consumption can be provided. In the case of using a transflective or reflective liquid crystal display device for the display portion 2705, the e-book reader may be used in a comparatively bright environment; accordingly, a solar cell may be provided so that power generation by the solar cell and charge by a battery can be performed. When a lithium ion battery is used as the battery, there are advantages of downsizing and the like.

FIG. 5C illustrates an example in which the housing 2701 is provided with an operation portion and the like. For example, the housing 2701 is provided with a power switch 2721, operation keys 2723, a speaker 2725, and the like. With the operation keys 2723, pages can be turned. Note that a keyboard, a pointing device, or the like may also be provided on the surface of the housing, on which the display portion is provided. An external connection terminal (an earphone terminal, a USB terminal, or the like), a recording medium insertion portion, and the like may be provided on the back surface or the side surface of the housing. Further, the e-book reader may have a function of an electronic dictionary.

The e-book reader may transmit and receive data wirelessly. Through wireless communication, desired book data or the like can be purchased and downloaded from an electronic book server.

Figure 5D:
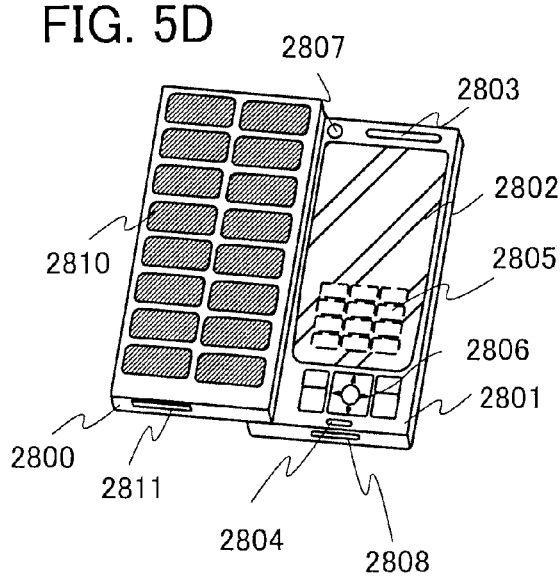

FIG. 5D illustrates a mobile phone, which includes two housings, a housing 2800 and a housing 2801. The housing 2801 includes a display panel 2802, a speaker 2803, a microphone 2804, a pointing device 2806, a camera lens 2807, an external connection terminal 2808, and the like. The housing 2800 includes a solar cell 2810 for charging the mobile phone, an external memory slot 2811, and the like. Further, an antenna is incorporated in the housing 2801. The liquid crystal display device described in any of the above embodiments is used for the display panel 2802, whereby a mobile phone with low power consumption can be provided.

The display panel 2802 is provided with a touch panel. A plurality of operation keys 2805 which is displayed as images is illustrated by dashed lines in FIG. 5D. Note that a boosting circuit by which a voltage output from the solar cell 2810 is increased to be sufficiently high for each circuit is also included.

In the display panel 2802, the display direction can be appropriately changed depending on a usage pattern. The mobile phone is provided with the camera lens 2807 on the same surface as the display panel 2802, and thus it can be used as a video phone. The speaker 2803 and the microphone 2804 can be used for videophone calls, recording and playing sound, and the like as well as voice calls. Further, the housings 2800 and 2801 which are developed as illustrated in FIG. 5D can overlap with each other by sliding; thus, the size of the mobile phone can be decreased, which makes the mobile phone suitable for being carried.

The external connection terminal 2808 can be connected to an AC adapter and various types of cables such as a USB cable, and charging and data communication with a personal computer are possible. A large amount of data can be stored and can be moved by inserting a storage medium into the external memory slot 2811.

In addition to the above functions, an infrared communication function, a television reception function, or the like may be provided.

Figure 5E:
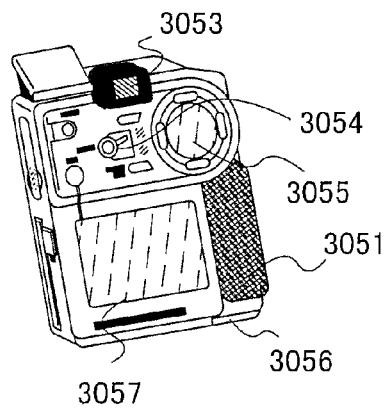

FIG. 5E illustrates a digital video camera, which includes a main body 3051, a display portion 3057, an eyepiece 3053, an operation switch 3054, a display portion 3055, a battery 3056, and the like. The liquid crystal display device described in any of the above embodiments is used for the display portion 3057 and the display portion 3055, whereby a digital video camera with low power consumption can be provided.

Figure 5F:
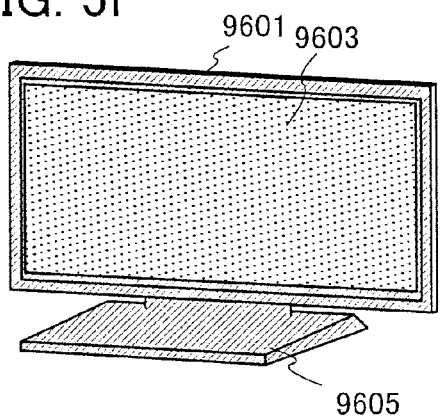

FIG. 5F illustrates a television device, which includes a housing 9601, a display portion 9603, and the like. The display portion 9603 can display images. Here, the housing 9601 is supported by a stand 9605. The liquid crystal display device described in any of the above embodiments is used for the display portion 9603, whereby a television device with low power consumption can be provided.

The television device can be operated with an operation switch of the housing 9601 or a separate remote controller. The remote controller may be provided with a display portion for displaying data output from the remote controller.

Note that the television device is provided with a receiver, a modem, and the like. With the use of the receiver, general television broadcasting can be received. Furthermore, when the television device is connected to a communication network by wired or wireless connection via the modem, one-way (from a transmitter to a receiver) or two-way (between a transmitter and a receiver, between receivers, or the like) data communication can be performed.

The structures, methods, and the like described in this embodiment can be combined as appropriate with any of the structures, methods, and the like described in the other embodiments.

EXAMPLE 1

This example shows an example for synthesizing (4R, 5R)-2,2-dimethyl-α,α,α',α'-tetra[4-(trans-4-n-pentylcyclohexyl)phenyl]-1,3-dioxolane-4,5-dimethanol (abbreviation: R-DOL-PC5), which is the dioxolane derivative represented by Structural Formula (100) in Embodiment 1.

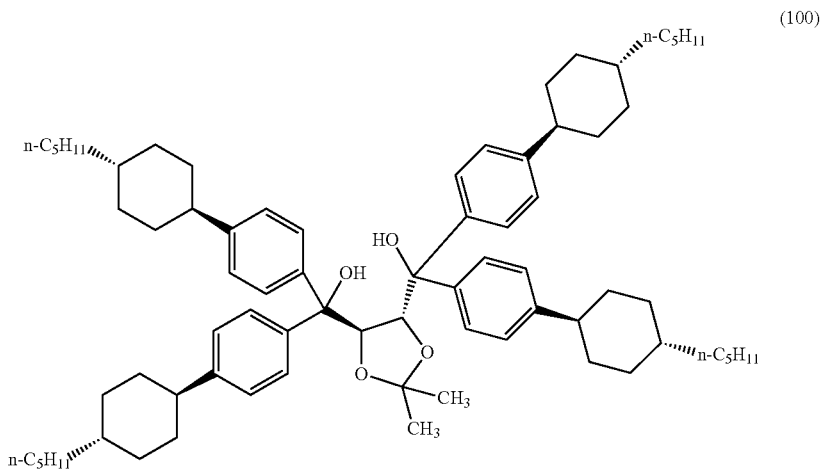

(100)

Into a 100-mL three-necked-flask, 0.33 g (13 mmol) of magnesium was put, and the air in the flask was replaced with nitrogen. Into this flask, 5.0 mL of tetrahydrofuran and several drops of dibromoethane were added, and the mixture was stirred at room temperature. To this mixture, a solution containing 3.9 g (14 mmol) of 1-bromo-4-[trans-4-(n-pentyl)cyclohexyl]benzene in 10 mL of tetrahydrofuran was dropped from a dropping funnel with stirring the mixture. Then, the mixture was further stirred at 80° C. for 1 hour under a nitrogen stream. After a predetermined period, a solution containing 0.61 g (2.8 mmol) of (−)-2,3-O-isopropylidene-L-tartaric acid dimethyl ester in 5.0 mL of tetrahydrofuran was dropped to the mixture from a dropping funnel with stirring the mixture. Then, the mixture was further stirred at 80° C. for 11.5 hours under a nitrogen stream. After a predetermined period, methanol, water, and a dilute hydrochloric acid were added in this order to the mixture, and an aqueous layer was subjected to extraction with toluene. The extracted solution and the organic layer were combined, washed with water, a saturated aqueous solution of sodium hydrogen carbonate, and saturated saline, and dried with magnesium sulfate.

This mixture was separated by gravity filtration, and the obtained filtrate was concentrated to give a yellow oily substance. The oily substance was purified by silica gel column chromatography (developing solvent: toluene). The resulting fraction was concentrated and dried in a vacuum to give a yellow oily substance. This oily substance was purified by high performance liquid column chromatography (HPLC) (developing solvent: chloroform). The resulting fraction was concentrated and dried in a vacuum to give 1.5 g of the target light-yellow solid of R-DOL-PC5 in a yield of 51%. The scheme of the above reactions is shown in (E1-1).

99.9 wt %:0.1 wt % (=nematic liquid crystal: R-DOL-PC5). As the nematic liquid crystal, a mixed liquid crystal containing a mixed liquid crystal E-8 (produced by LCC Corporation, Ltd.), 4-(trans-4-n-propylcyclohexyl)-3',4'-difluoro-1,1'-biphenyl (abbreviation: CPP-3FF) (produced by Daily Polymer Corporation), and 4-n-pentylbenzoic acid 4-cyano-3-fluorophenyl ester (abbreviation: PEP-5CNF) (produced by Daily Polymer Corporation) was used. The mixture ratio was 40 wt %:30 wt %:30 wt % (=E-8: CPP-3FF: PEP-5CNF).

The measurement results show that the HTP of the liquid crystal composition including R-DOL-PC5 was 29 μm$^{-1}$, and by adding an extremely small amount of R-DOL-PC5 into the liquid crystal composition, the liquid crystal composition can have high HTP. Thus, R-DOL-PC5 is a chiral (E1-1)

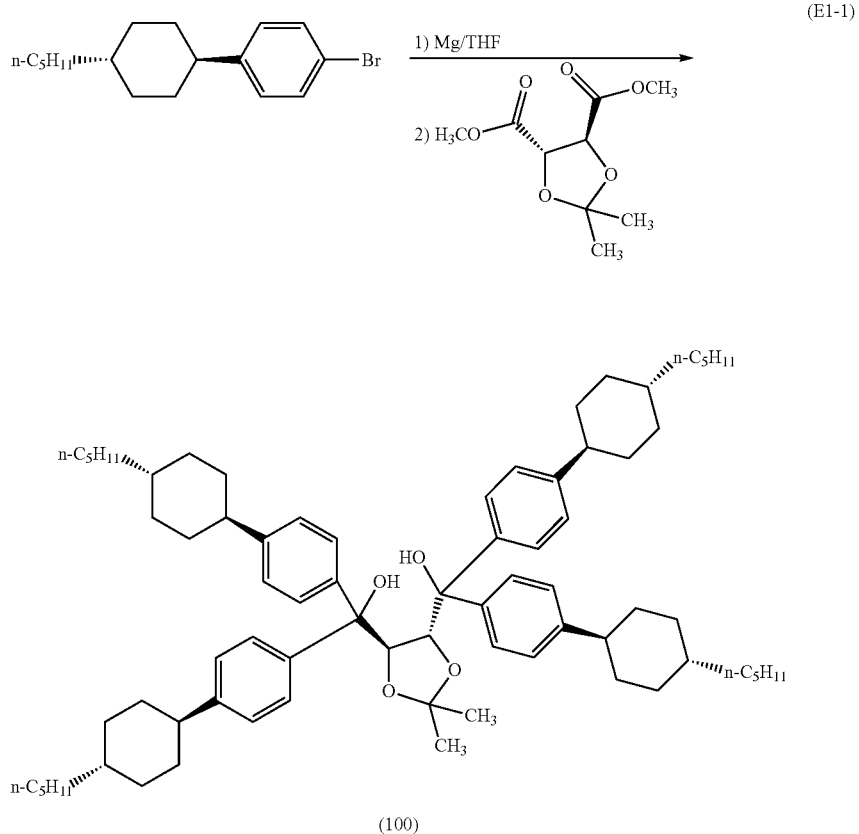

(100)

This compound was identified as the target R-DOL-PC5 by nuclear magnetic resonance (NMR).

$^1$H NMR data of the obtained substance, R-DOL-PC5, are as follows. $^1$H NMR (TCE, 300 MHz): δ (ppm)=0.89-1.46 (m, 82H), 1.80-1.98 (m, 16H), 2.32 (s, 2H), 2.37-2.50 (m, 4H), 4.58 (s, 2H), 7.03-7.40 (m, 16H).

Figure 6A:
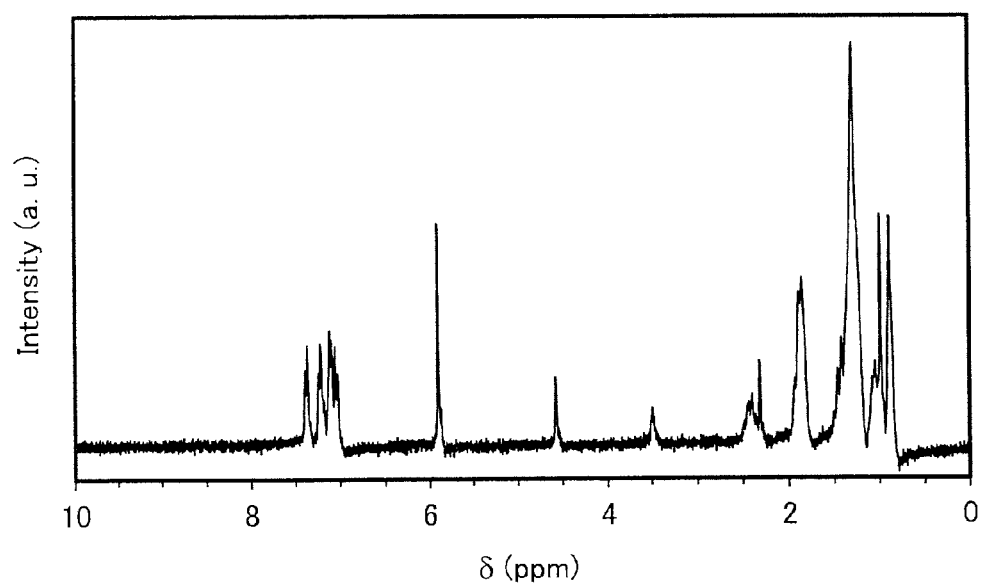
FIGS. 6A and 6B are $^1$H NMR charts of (4R,5R)-2,2-dimethyl-α,α,α',α'-tetra[4-(trans-4-n-pentylcyclohexyl) phenyl]-1,3-diox olane-4,5-dimethanol (R-DOL-PC5)
Figure 6B:
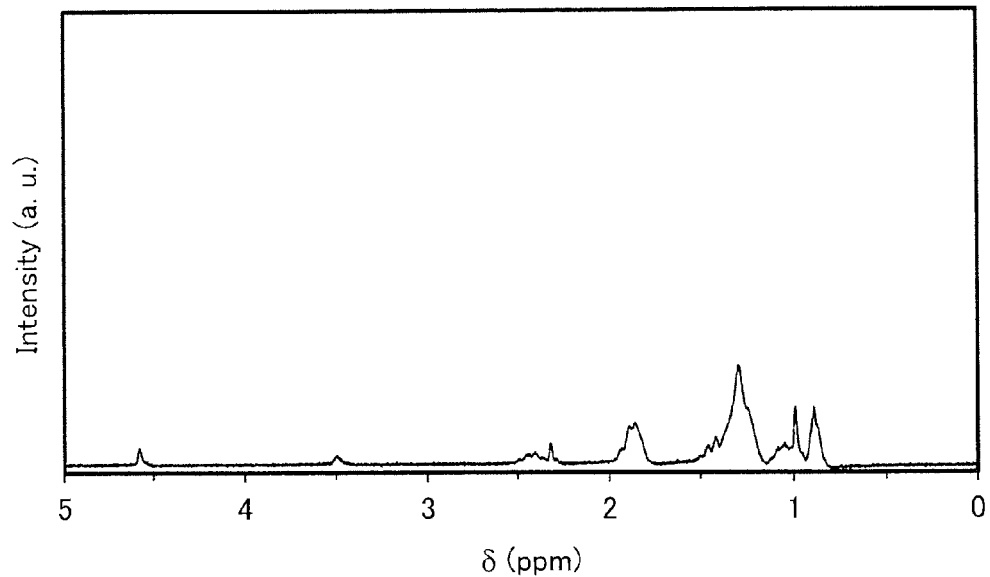
Figure 7:
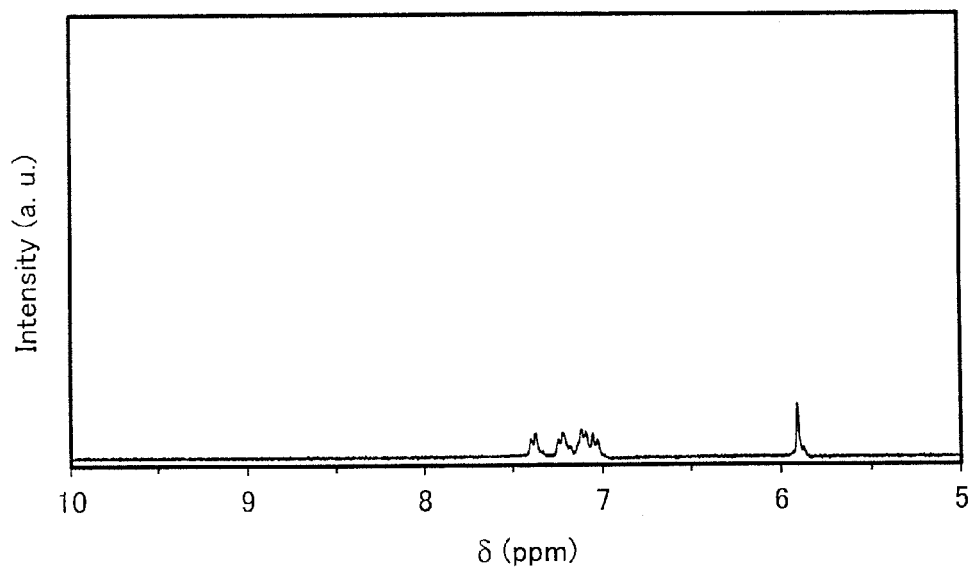
FIG. 7 is a $^1$H NMR chart of R-DOL-PC5.

FIGS. 6A and 6B and FIG. 7 show the $^1$H NMR charts. Note that FIG. 6B is an enlarged chart showing a range of from 0 ppm to 5 ppm of FIG. 6A, and FIG. 7 is an enlarged chart showing a range of from 5 ppm to 10 ppm of FIG. 6A. The measurement results show that R-DOL-PC5, which was the target substance, was obtained.

HTP of a liquid crystal composition that is a mixture of R-DOL-PC5 synthesized in this example and a nematic liquid crystal was measured. The measurement was performed at room temperature by the Grandjean-Cano wedge method. Note that the mixture ratio of the nematic liquid crystal to R-DOL-PC5 in the liquid crystal composition was material having strong twisting power, which means that the proportion of a chiral material in a liquid crystal composition can be reduced.

Thus, R-DOL-PC5 synthesized in this example has proved favorable as a chiral material of a liquid crystal composition. Furthermore, the liquid crystal composition in which one embodiment of the present invention is used has strong twisting power, so that a liquid crystal display device with high contrast can be achieved with the use of the liquid crystal composition.

EXAMPLE 2

This example shows an example for synthesizing (4R, 5R)-2,2-dimethyl-α,α,α',α'-tetra[4'-(n-hexyl-1-oxy)-1,1'-biphenyl-4-yl]-1,3-dioxolane-4,5-dimethanol (abbreviation: R-DOL-PPO6), which is the dioxolane derivative represented by Structural Formula (101) in Embodiment 1.

(101)

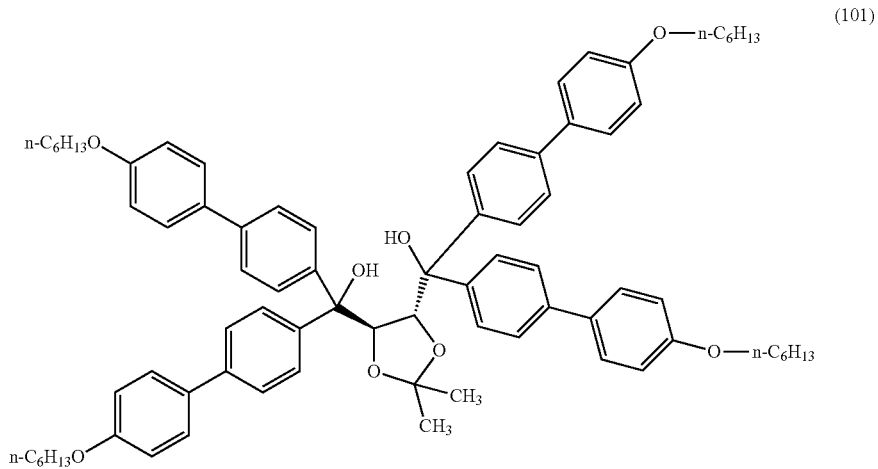

Into a 100-mL three-necked-flask, 0.44 g (18 mmol) of magnesium was put, and the air in the flask was replaced with nitrogen. Into this flask, 5.0 mL of tetrahydrofuran and several drops of dibromoethane were added, and the mixture was stirred at room temperature. To this mixture, a solution containing 6.3 g (19 mmol) of 4-bromo-4'-(n-hexyl-1-oxy)-1,1'-biphenyl in 10 mL of tetrahydrofuran was dropped from a dropping funnel with stirring the mixture. Then, the mixture was further stirred at 80° C. for 1 hour under a nitrogen stream. After a predetermined period, a solution containing 0.83 g (3.8 mmol) of (−)-2,3-O-isopropylidene-L-tartaric acid dimethyl ester in 3.9 mL of tetrahydrofuran was dropped to the mixture from a dropping funnel with stirring the mixture. Then, the mixture was further stirred at 80° C. for 7.5 hours under a nitrogen stream. After a predetermined period, methanol, water, and a dilute hydrochloric acid were added in this order to the mixture, and an aqueous layer was subjected to extraction with ethyl acetate. The extracted solution and the organic layer were combined, washed with water, a saturated aqueous solution of sodium hydrogen carbonate, and saturated saline, and dried with magnesium sulfate.

This mixture was separated by gravity filtration, and the obtained filtrate was concentrated to give a yellow oily substance. The oily substance was purified by silica gel column chromatography (developing solvent:a mixed solvent of hexane:ethyl acetate=10:1, then a mixed solvent of hexane: ethyl acetate=5:1, and then ethyl acetate). The resulting fraction was concentrated to give a yellow oily substance. This oily substance was purified by HPLC (developing solvent: chloroform). The resulting fraction was concentrated and dried in a vacuum to give 0.57 g of the target yellow oily substance of R-DOL-PPO6 in a yield of 13%. The scheme of the above reaction is shown in (E2-1).

(E2-1)

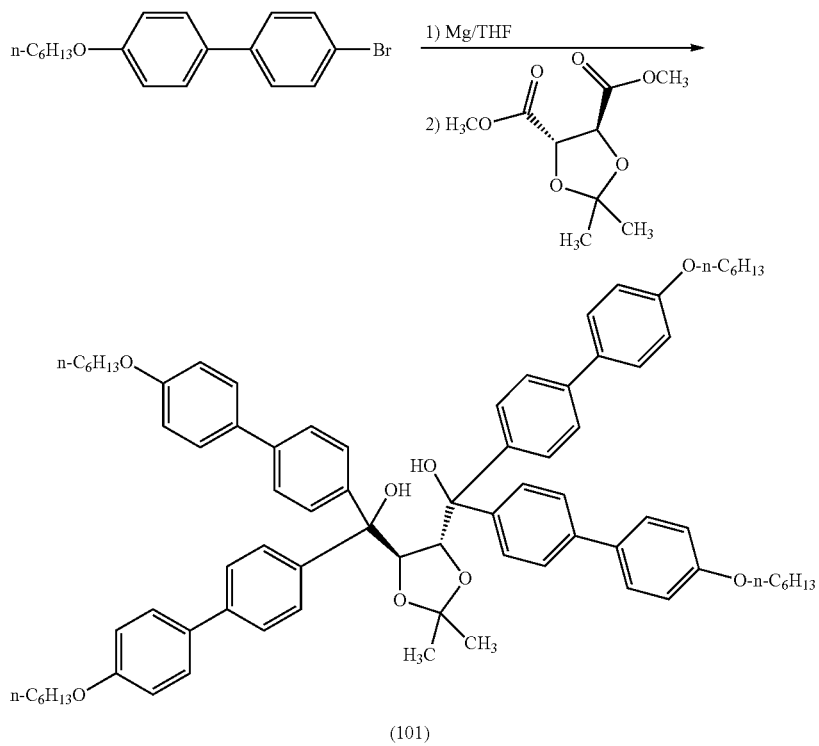

This compound was identified as the target R-DOL-PPO6 by NMR.

$^1$H NMR data of the obtained substance, R-DOL-PPO6, are as follows. $^1$H NMR (TCE, 300 MHz): δ (ppm)=0.88-0.94 (m, 12H), 1.16 (s, 6H), 1.24-1.49 (m, 18H), 1.74-1.86 (m, 8H), 3.95-4.03 (m, 8H), 4.71 (s, 2H), 6.90-6.99 (m, 8H), 7.39-7.64 (m, 24H).

Figure 8A:
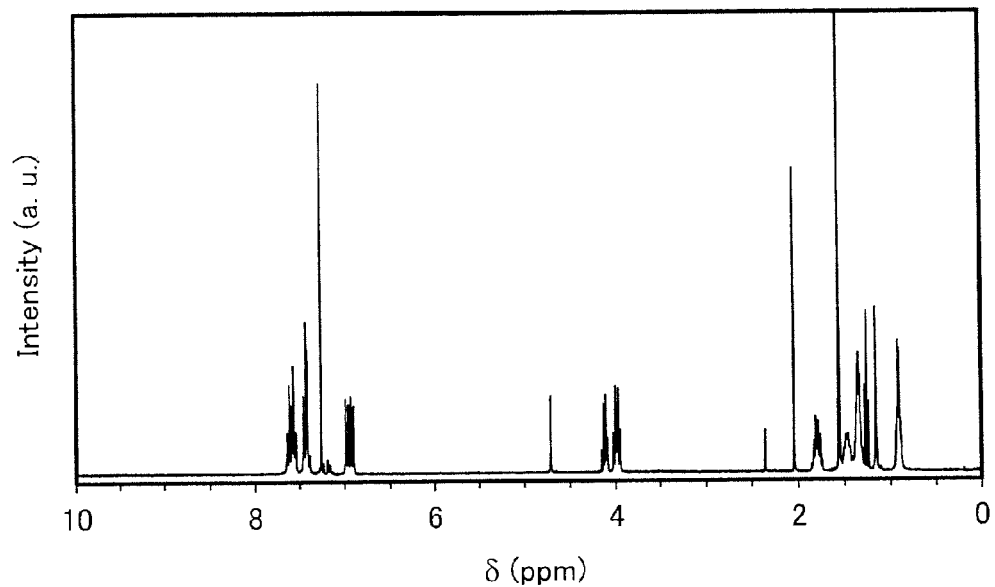
FIGS. 8A and 8B are $^1$H NMR charts of (4R,5R)-2,2-dimethyl-α,α,α',α'-tetra[4'-(n-hexyl-1-oxy)-1,1-biphenyl-4-yl]-1,3-diox olane-4,5-dimethanol (R-DOL-PPO6)
Figure 8B:
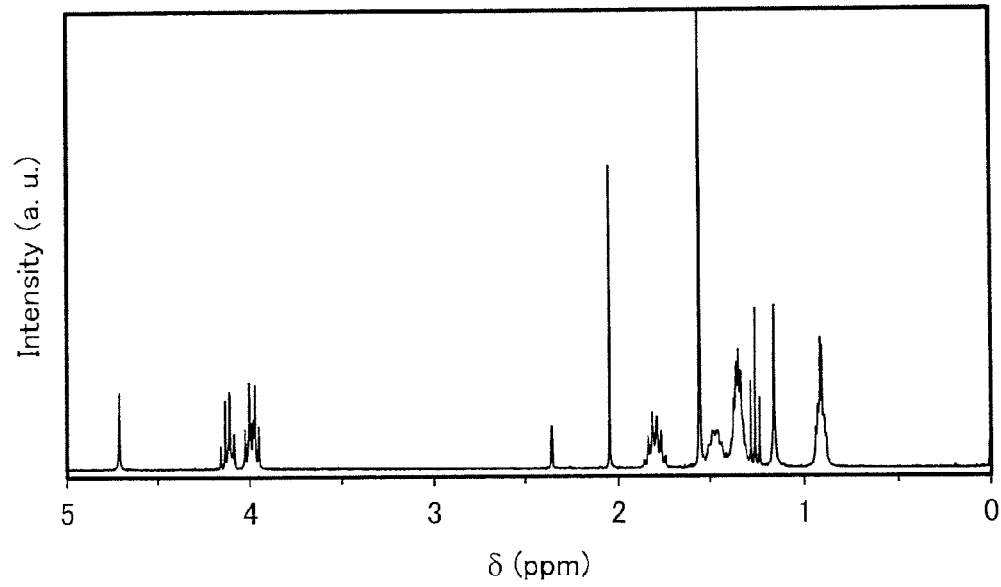
Figure 9:
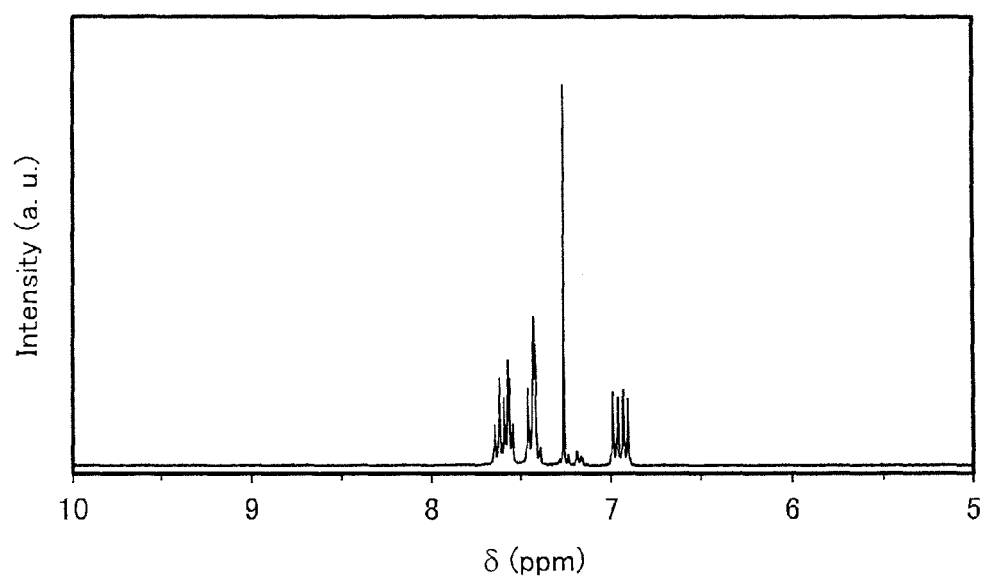
FIG. 9 is a $^1$H NMR chart of R-DOL-PPO6.

FIGS. 8A and 8B and FIG. 9 show the $^1$H NMR charts. Note that FIG. 8B is an enlarged chart showing a range of from 0 ppm to 5 ppm of FIG. 8A, and FIG. 9 is an enlarged chart showing a range of from 5 ppm to 10 ppm of FIG. 8A. The measurement results show that R-DOL-PPO6, which was the target substance, was obtained.

HTP of a liquid crystal composition that is a mixture of R-DOL-PPO6 synthesized in this example and a nematic liquid crystal was measured. The measurement was performed at room temperature by the Grandjean-Cano wedge method. Note that the mixture ratio of the nematic liquid crystal to R-DOL-PPO6 in the liquid crystal composition was 99.9 wt %:0.1 wt % (=nematic liquid crystal: R-DOL-PPO6). As the nematic liquid crystal, a mixed liquid crystal containing a mixed liquid crystal E-8 (produced by LCC Corporation, Ltd.), CPP-3FF (produced by Daily Polymer Corporation), and PEP-5CNF (produced by Daily Polymer Corporation) was used. The mixture ratio was 40 wt %:30 wt %:30 wt % (=E-8: CPP-3FF: PEP-5CNF).

The measurement results show that the HTP of the liquid crystal composition including R-DOL-PPO6 was 43 μm$^{-1}$, and by adding an extremely small amount of R-DOL-PPO6 into the liquid crystal composition, the liquid crystal composition can have high HTP. Thus, R-DOL-PPO6 is a chiral material having strong twisting power, which means that the proportion of a chiral material in a liquid crystal composition can be reduced.

Thus, R-DOL-PPO6 synthesized in this example has proved favorable as a chiral material of a liquid crystal composition. Furthermore, the liquid crystal composition in which one embodiment of the present invention is used has strong twisting power, so that a liquid crystal display device with high contrast can be achieved with the use of the liquid crystal composition.

EXAMPLE 3

This example shows an example for synthesizing (4R, 5R)-2,2-dimethyl-α,α,α',α'-tetra[4'-(n-pentyl)-1,1'-biphenyl-4-yl]-1,3-dioxolane-4,5-dimethanol (abbreviation: R-DOL-PP5), which is the dioxolane derivative represented by Structural Formula (102) in Embodiment 1.

Into a 100-mL three-necked-flask, 0.34 g (14 mmol) of magnesium was put, and the air in the flask was replaced with nitrogen. Into this flask, 5.0 mL of tetrahydrofuran and several drops of dibromoethane were added, and the mixture was stirred at room temperature. To this mixture, a solution containing 4.4 g (15 mmol) of 4-bromo-4'-(n-pentyl)-1,1'-biphenyl in 7.0 mL of tetrahydrofuran was dropped from a dropping funnel with stirring the mixture. Then, the mixture was further stirred at 80° C. for 1 hour under a nitrogen stream. After a predetermined period, a solution containing 0.63 g (2.9 mmol) of (−)-2,3-O-isopropylidene-L-tartaric acid dimethyl ester in 2.0 mL of tetrahydrofuran was dropped to the mixture from a dropping funnel with stirring the mixture. Then, the mixture was further stirred at 80° C. for 1 hour under a nitrogen stream. After a predetermined period, methanol, water, and a hydrochloric acid were added in this order to the mixture, and an aqueous layer was subjected to extraction with toluene. The extracted solution and the organic layer were combined, washed with water, a saturated aqueous solution of sodium bicarbonate, and saturated saline, and dried with magnesium sulfate.

This mixture was separated by gravity filtration, and the obtained filtrate was concentrated to give a yellow oily substance. The oily substance was purified by silica gel column chromatography (developing solvent:a mixed solvent of hexane:ethyl acetate=5:1). The resulting fraction was concentrated to give a yellow oily substance. This oily substance was purified by HPLC (developing solvent: chloroform). The resulting fraction was concentrated and dried in a vacuum to give 2.1 g of the target light-yellow solid of R-DOL-PP5 in a yield of 68%. The scheme of the above reaction is shown in (E3-1).

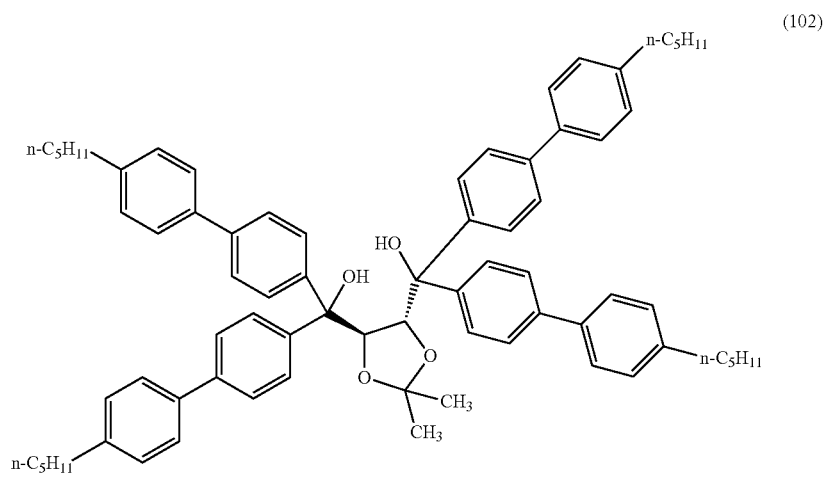

(102)

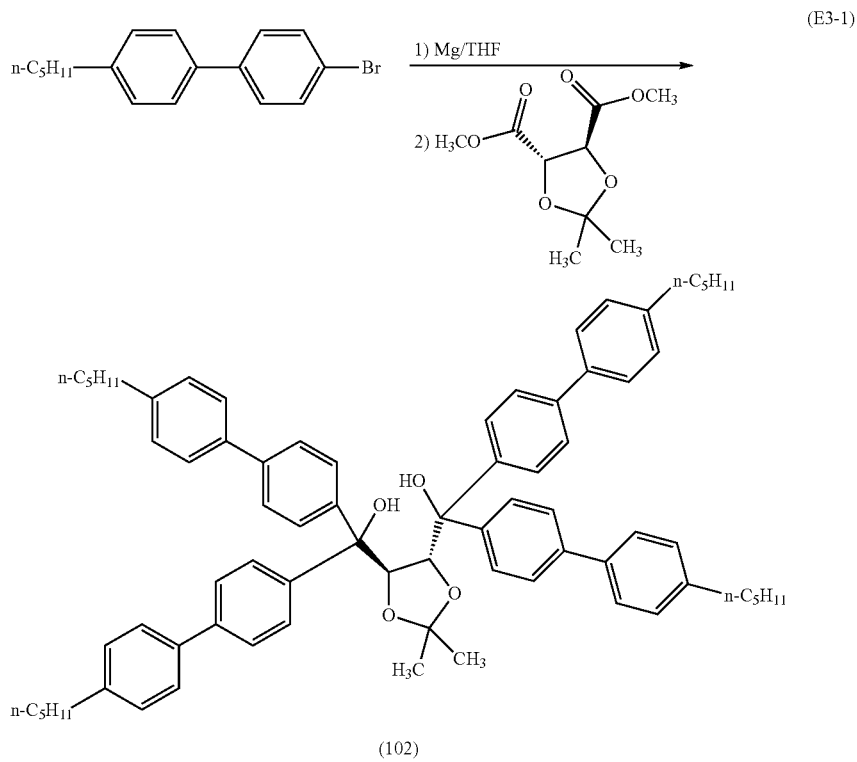

(E3-1)

This compound was identified as the target R-DOL-PP5 by NMR.

$^1$H NMR data of the obtained substance, R-DOL-PP5, are as follows. $^1$H NMR (TCE, 300 MHz): δ (ppm)=0.90 (s, 12H), 1.16 (s, 6H), 1.24-1.36 (m, 16H), 1.60-1.71 (m, 8H), 2.61 (s, 8H), 3.69 (s, 2H), 4.76 (s, 2H), 7.16-7.23 (m, 8H), 7.44-7.61 (m, 24H).

Figure 10A:
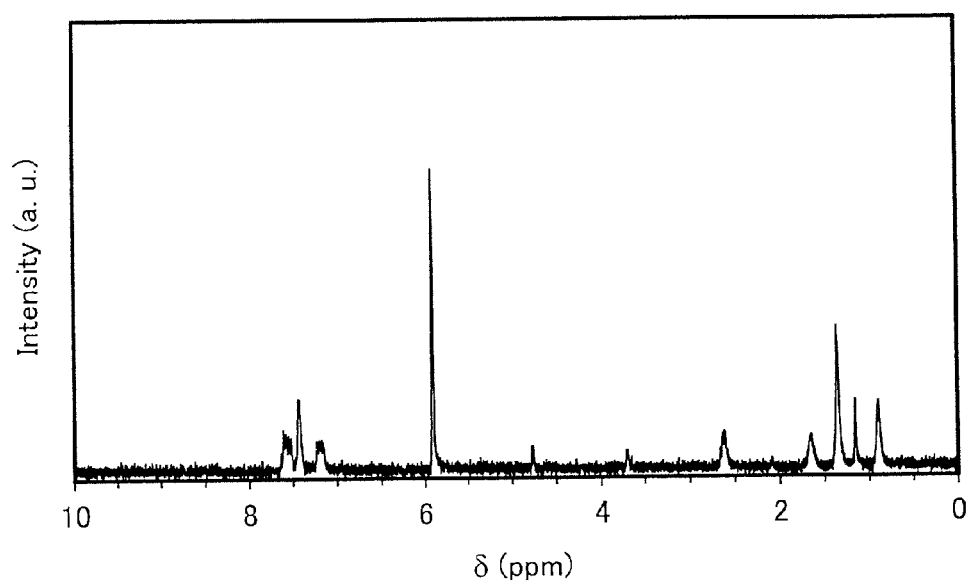
FIGS. 10A and 10B are $^1$H NMR charts of (4R,5R)-2,2-dimethyl-α,α,α',α'-tetra[4'-(n-pentyl)-1,1-biphenyl-4-yl]-1,3-dioxolane-4,5-dimethanol (R-DOL-PP5)
Figure 10B:
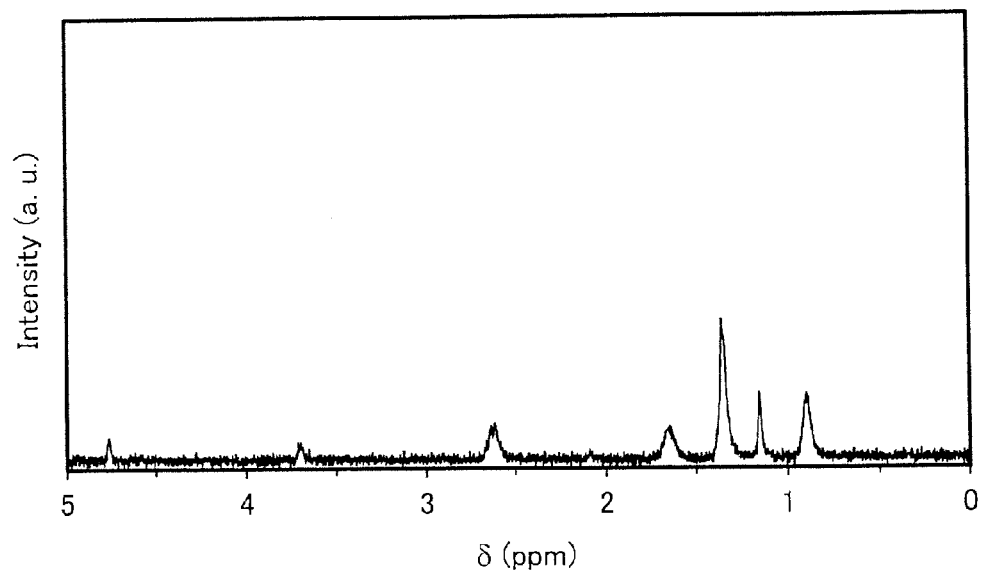
Figure 11:
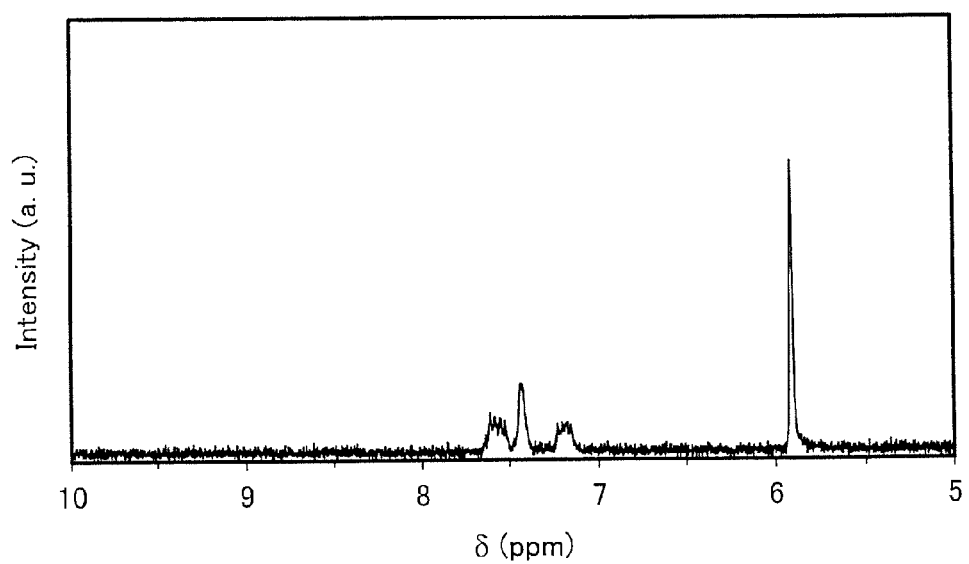
FIG. 11 is a $^1$H NMR chart of R-DOL-PP5.

FIGS. 10A and 10B and FIG. 11 show the $^1$H NMR charts. Note that FIG. 10B is an enlarged chart showing a range of from 0 ppm to 5 ppm of FIG. 10A, and FIG. 11 is an enlarged chart showing a range of from 5 ppm to 10 ppm of FIG. 10A. The measurement results show that R-DOL-PP5, which was the target substance, was obtained.

HTP of a liquid crystal composition that is a mixture of R-DOL-PP5 synthesized in this example and a nematic liquid crystal was measured. The measurement was performed at room temperature by the Grandjean-Cano wedge method. Note that the mixture ratio of the nematic liquid crystal to R-DOL-PP5 in the liquid crystal composition was 99.9 wt %:0.1 wt % (=nematic liquid crystal: R-DOL-PP5). As the nematic liquid crystal, a mixed liquid crystal containing a mixed liquid crystal E-8 (produced by LCC Corporation, Ltd.), CPP-3FF (produced by Daily Polymer Corporation), and PEP-5CNF (produced by Daily Polymer Corporation) was used. The mixture ratio was 40 wt %:30 wt %:30 wt % (=E-8: CPP-3FF: PEP-5CNF).

The measurement results show that the HTP of the liquid crystal composition including R-DOL-PP5 was 50 μm$^{-1}$, and by adding an extremely small amount of R-DOL-PP5 into the liquid crystal composition, the liquid crystal composition can have high HTP. Thus, R-DOL-PP5 is a chiral material having strong twisting power, which means that the proportion of a chiral material in a liquid crystal composition can be reduced.

Thus, R-DOL-PP5 synthesized in this example has proved favorable as a chiral material of a liquid crystal composition. Furthermore, the liquid crystal composition in which one embodiment of the present invention is used has strong twisting power, so that a liquid crystal display device with high contrast can be achieved with the use of the liquid crystal composition.

EXAMPLE 4

In this example, three kinds of liquid crystal compositions that are each one embodiment of the present invention and three kinds of TN mode liquid crystal elements including the liquid crystal compositions were prepared, and characteristics of the liquid crystal compositions and the liquid crystal elements were evaluated.

In the three kinds of liquid crystal compositions made in this example, a mixed liquid crystal ZLI-4792 (produced by Merck) was used in common as a nematic liquid crystal. As chiral materials for the respective liquid crystal compositions, R-DOL-PC5, R-DOL-PPO6, and R-DOL-PP5 described in Examples 1 to 3, respectively, were used. In the liquid crystal compositions, the proportions of the chiral materials R-DOL-PC5, R-DOL-PPO6, and R-DOL-PP5 with respect to the nematic liquid crystal ZLI-4792 were 0.03 wt %, 0.04 wt %, and 0.03 wt %, respectively.

The helical pitches of the three kinds of liquid crystal compositions prepared in this example were 49.7 μm, 55.2 μm, and 103.7 μm, which were measured at room temperature by the Grandjean-Cano wedge method.

Then, the alignment in the transmissive TN cells before and after voltage application was observed. The TN cells were the cells for vertical electric field application with a cell thickness of 4 μm. A pixel electrode layer was formed using indium tin oxide containing silicon oxide (ITSO) by a sputtering method over each of two glass substrates. The thickness of the pixel electrode layer was 110 nm. Then, SE-6414 (produced by Nissan Chemical Industries, Ltd.) was applied as a horizontal alignment film over each of the glass substrates with a spin coater, and was baked at 230° C.

Next, rubbing treatment was performed with a rubbing apparatus, and spacers with a diameter of 4 μm were dispersed over one of the substrates. A heat-curable sealing material was applied over the substrate over which the spacers were dispersed, and the two substrates were bonded to each other such that the rubbing directions of the substrates intersect each other. The bonded substrates were subjected to heat treatment at 160° C. for 4 hours while being pressed with a pressure of 0.3 kgf/cm².

The substrates formed in the above manner were divided, and the three kinds of liquid crystal compositions were injected by an injecting method using capillary action, so that three kinds of liquid crystal elements were fabricated. These three kinds of liquid crystal elements were observed by crossed nicols observation with a polarizing microscope (MX-61L produced by Olympus Corporation), which showed that line defects due to a reverse twist were not generated at all and favorable alignment was obtained in all the liquid crystal elements.

Next, voltage-transmittance characteristics of these three kinds of liquid crystal elements were measured with a RETS+VT measurement system (produced by Otsuka Electronics Co., Ltd.). The voltage was applied at 0.2 V intervals in the range of from 0 V to 10 V. After the measurement, crossed nicols observation with the polarizing microscope was performed again, which showed that, in all the three kinds of liquid crystal elements, line defects due to the reverse twist were not generated at all and favorable alignment was obtained also after the voltage application.

The above-described results indicate that the liquid crystal compositions of embodiments of the present invention can be used for TN mode elements by including the dioxolane derivative represented by General Formula (G1) as a chiral material.

EXAMPLE 5

In this example, R-DOL-PC5 whose synthesis method is shown in Example 1 and a nematic liquid crystal were mixed to prepare a liquid crystal composition. Note that the mixture ratio of the nematic liquid crystal to R-DOL-PC5 in the liquid crystal composition was 86.0 wt %:14.0 wt % (=nematic liquid crystal: R-DOL-PC5). As the nematic liquid crystal, a mixed liquid crystal containing a mixed liquid crystal E-8 (produced by LCC Corporation, Ltd.), CPP-3FF (produced by Daily Polymer Corporation), and PEP-5CNF (produced by Daily Polymer Corporation) was used. The mixture ratio was 40 wt %:30 wt %:30 wt % (=E-8: CPP-3FF: PEP-5CNF).

In this example, the liquid crystal composition in the liquid crystal element was made to be an isotropic phase at first. Then, the liquid crystal composition was observed with a polarizing microscope while the temperature was decreased by 1.0° C. per minute with a temperature controller, and the temperature at which the liquid crystal composition is transformed to a blue phase was measured. The liquid crystal composition of this example exhibited a blue phase at 42.3° C.

EXAMPLE 6

In this example, R-DOL-PP5 whose synthesis method is shown in Example 3 and a nematic liquid crystal were mixed to prepare a liquid crystal composition. Note that the mixture ratio of the nematic liquid crystal to R-DOL-PP5 in the liquid crystal composition was 89.2 wt %:10.8 wt % (=nematic liquid crystal: R-DOL-PP5). As the nematic liquid crystal, a mixed liquid crystal containing a mixed liquid crystal E-8 (produced by LCC Corporation, Ltd.), CPP-3FF (produced by Daily Polymer Corporation), and PEP-5CNF (produced by Daily Polymer Corporation) was used. The mixture ratio was 40 wt %:30 wt %:30 wt % (=E-8: CPP-3FF: PEP-5CNF).

In this example, the liquid crystal composition in the liquid crystal element was made to be an isotropic phase at first. Then, the liquid crystal composition was observed with a polarizing microscope while the temperature was decreased by 1.0° C. per minute with a temperature controller, and the temperature range where the liquid crystal composition exists in a blue phase was measured. In the liquid crystal composition of this example, the phase transition temperature between an isotropic phase and a blue phase was 46.2° C., and a phase transition temperature between a blue phase and a cholesteric phase was 41.4° C.

The above results show that the liquid crystal composition of one embodiment of the present invention can exhibit a blue phase by including the dioxolane derivative represented by General Formula (G1) as a chiral material.

EXAMPLE 7

This example shows an example for synthesizing (4R, 5R)-2,2-dimethyl-α,α,α',α'-tetra(naphthalen-1-yl)-1,3-dioxolane-4,5-dimethanol (abbreviation: R-DOL-αNp), which is the dioxolane derivative represented by Structural Formula (200) in Embodiment 2.

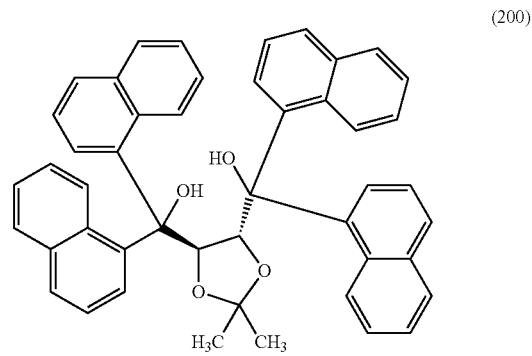 [SMILES: CC1(C)O[C@@H](C(O)(c2cccc3ccccc23)c2cccc3ccccc23)[C@H](C(O)(c2cccc3ccccc23)c2cccc3ccccc23)O1]

(200)

Into a 300-mL three-necked-flask, 1.6 g (64 mmol) of magnesium was put, and the air in the flask was replaced with nitrogen. Into this flask, 15 mL of tetrahydrofuran and several drops of dibromoethane were added, and the mixture was stirred at room temperature. To this mixture, a solution containing 11 mL (75 mmol) of 1-bromonaphthalene in 30 mL of tetrahydrofuran was dropped from a dropping funnel with stirring the mixture. Then, the mixture was further stirred at 80° C. for 1 hour under a nitrogen stream. After a predetermined period, a solution containing 2.7 mL (15 mmol) of (−)-2,3-O-isopropylidene-L-tartaric acid dimethyl ester in 10 mL of tetrahydrofuran was dropped to the mixture from a dropping funnel with stirring the mixture. Then, the mixture was further stirred at 80° C. for 1 hour under a nitrogen stream. After a predetermined period, methanol, water, and a dilute hydrochloric acid were added in this order to the mixture, and an aqueous layer was subjected to extraction with ethyl acetate. The extracted solution and the organic layer were combined, washed with water, a saturated aqueous solution of sodium hydrogen carbonate, and saturated saline, and dried with magnesium sulfate.

This mixture was separated by gravity filtration, and the obtained filtrate was concentrated to give a red oily substance. The oily substance was purified by HPLC (developing solvent: chloroform). The resulting fraction was concentrated to give a light-yellow solid. The obtained solid was washed with methanol and suction filtered to give 1.2 g of the target white solid of R-DOL-αNp in a yield of 17%. The scheme of the above reaction is shown in (E4-1).

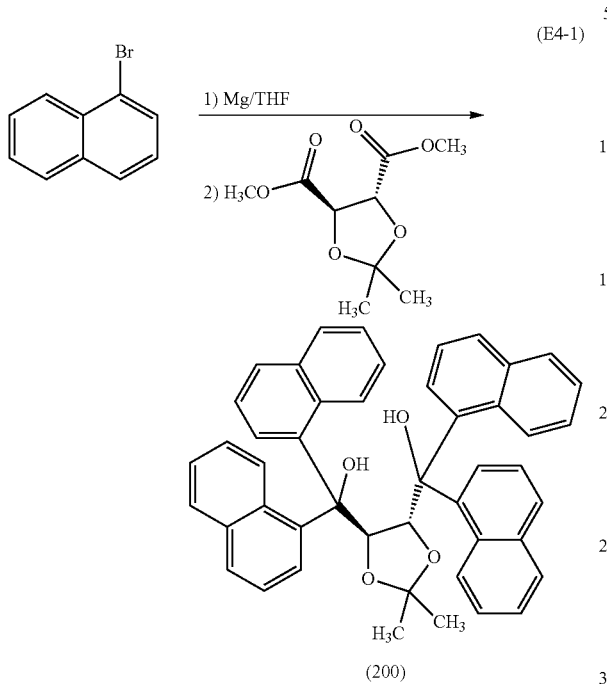

(E4-1)

(200)

This compound was identified as the target R-DOL-αNp by NMR.

$^1$H NMR data of the obtained substance, R-DOL-αNp, are as follows. $^1$H NMR (TCE, 300 MHz): δ (ppm)=0.52 (s, 2H), 1.35 (s, 6H), 3.41 (s, 2H), 6.89-8.08 (m, 28H).

Figure 12A:
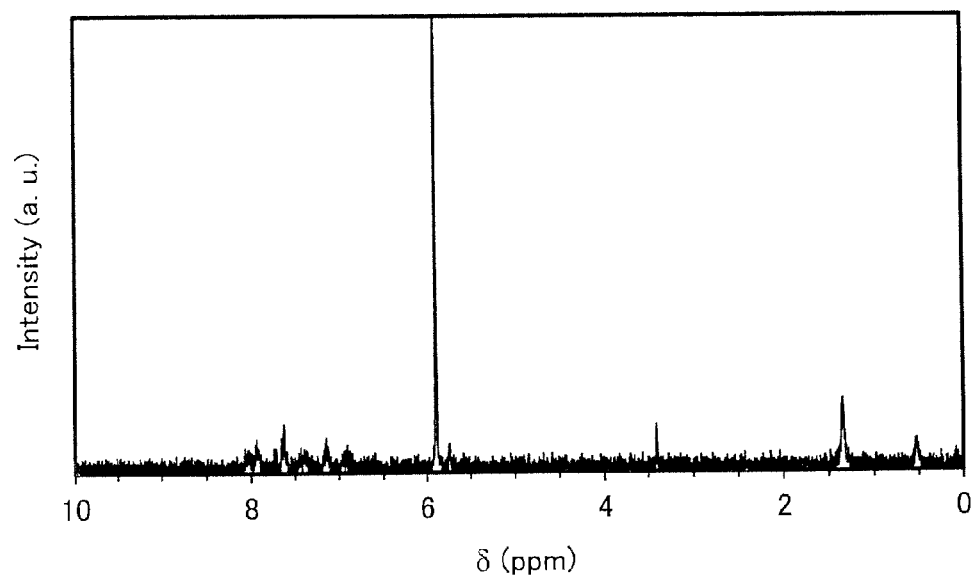
FIGS. 12A and 12B are $^1$H NMR charts of (4R,5R)-2,2-dimethyl-α,α,α',α'-tetra(naphthalen-1-yl)-1,3-dioxolane-4,5-dimethanol (R-DOL-αNp)
Figure 12B:
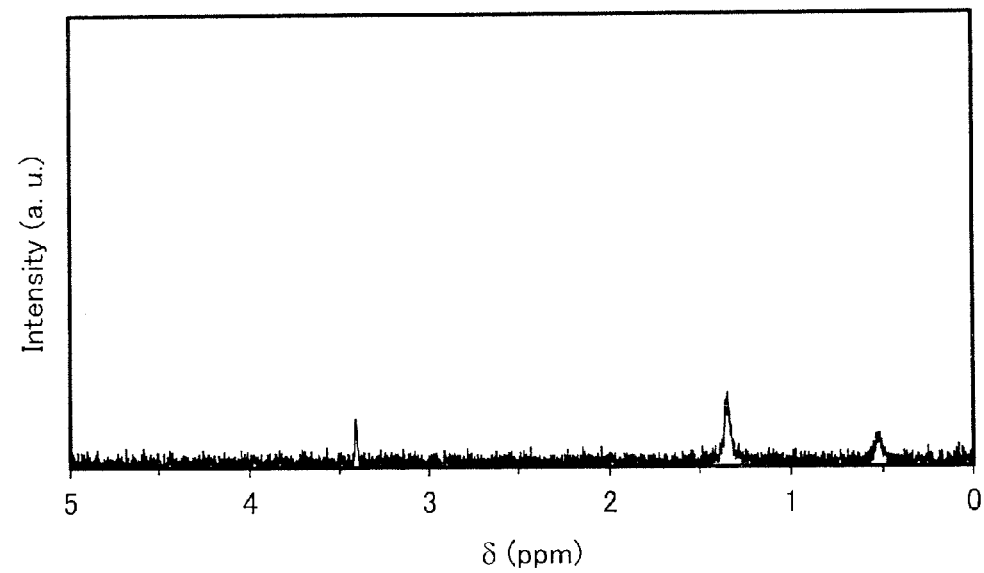
Figure 13:
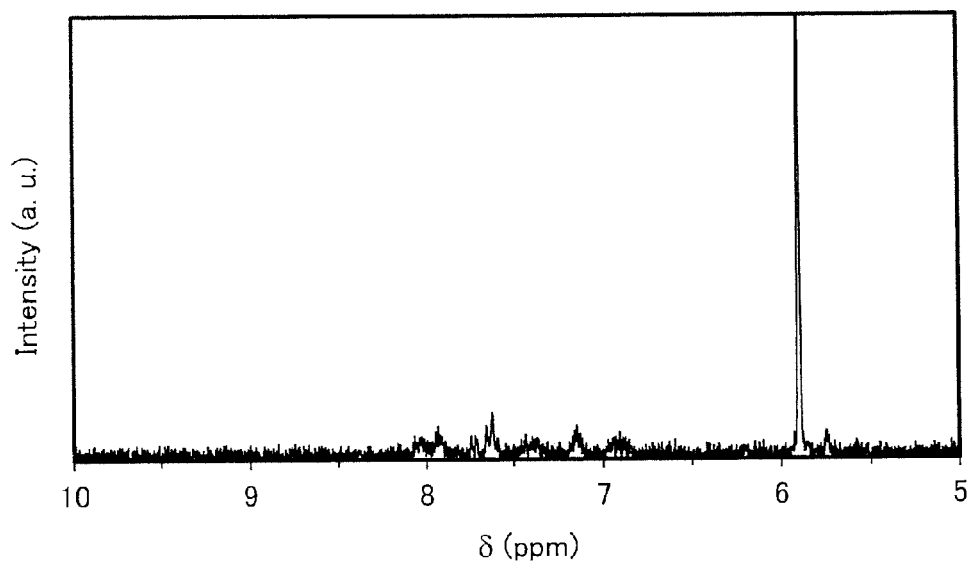
FIG. 13 is a $^1$H NMR chart of R-DOL-αNp.

FIGS. 12A and 12B and FIG. 13 show the $^1$H NMR charts. Note that FIG. 12B is an enlarged chart showing a range of from 0 ppm to 5 ppm of FIG. 12A, and FIG. 13 is an enlarged chart showing a range of from 5 ppm to 10 ppm of FIG. 12A. The measurement results show that R-DOL-αNp, which was the target substance, was obtained.

HTP of a liquid crystal composition that is a mixture of R-DOL-αNp synthesized in this example and a nematic liquid crystal was measured. The measurement was performed at room temperature by the Grandjean-Cano wedge method. Note that the mixture ratio of the nematic liquid crystal to R-DOL-αNp in the liquid crystal composition was 99.9 wt %:0.1 wt % (=nematic liquid crystal: R-DOL-αNp). As the nematic liquid crystal, a mixed liquid crystal containing a mixed liquid crystal E-8 (produced by LCC Corporation, Ltd.), CPP-3FF (produced by Daily Polymer Corporation), and PEP-5CNF (produced by Daily Polymer Corporation) was used. The mixture ratio was 40 wt %:30 wt %:30 wt % (=E-8: CPP-3FF: PEP-5CNF).

The measurement results show that the HTP of the liquid crystal composition including R-DOL-αNp was 88 μm$^{-1}$, and by adding an extremely small amount of R-DOL-αNp into the liquid crystal composition, the liquid crystal composition can have high HTP. Thus, R-DOL-αNp is a chiral material having strong twisting power, which means that the proportion of a chiral material in a liquid crystal composition device can be reduced.

Thus, R-DOL-αNp synthesized in this example has proved favorable as a chiral material of a liquid crystal composition. Furthermore, the liquid crystal composition in which one embodiment of the present invention is used has strong twisting power, so that a liquid crystal display device with high contrast can be achieved with the use of the liquid crystal composition.

EXAMPLE 8

This example shows an example for synthesizing (4R, 5R)-2,2-dimethyl-α,α,α',α'-tetra(pyren-1-yl)-1,3-dioxolane-4,5-dimethanol (abbreviation: R-DOL-Prna), which is the dioxolane derivative represented by Structural Formula (201) in Embodiment 2.

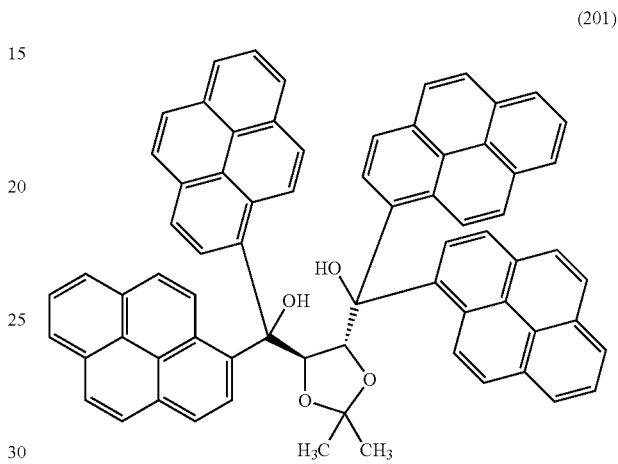

(201)

Into a 100-mL three-necked-flask, 0.36 g (15 mmol) of magnesium was put, and the air in the flask was replaced with nitrogen. Into this flask, 5.0 mL of tetrahydrofuran and several drops of dibromoethane were added, and the mixture was stirred at room temperature. To this mixture, a solution containing 4.8 g (16 mmol) of 1-bromopyrene in 10 mL of tetrahydrofuran was dropped from a dropping funnel with stirring the mixture. Then, the mixture was further stirred at 80° C. for 1 hour under a nitrogen stream. After a predetermined period, a solution containing 0.68 g (3.1 mmol) of (−)-2,3-O-isopropylidene-L-tartaric acid dimethyl ester in 5.0 mL of tetrahydrofuran was dropped to the mixture from a dropping funnel with stirring the mixture. Then, the mixture was further stirred at 80° C. under a nitrogen stream. After a predetermined period, methanol, water, and a dilute hydrochloric acid were added in this order to the mixture, and an aqueous layer was subjected to extraction with ethyl acetate. The extracted solution and the organic layer were combined, washed with water, a saturated aqueous solution of sodium hydrogen carbonate, and saturated saline, and dried with magnesium sulfate.

This mixture was separated by gravity filtration, and the obtained filtrate was concentrated to give a brown solid. The solid was purified by silica gel column chromatography (developing solvent:a mixed solvent of hexane:ethyl acetate=5:1). The resulting fraction was concentrated and dried in a vacuum to give a brown solid. This solid was purified by HPLC (developing solvent: chloroform). The obtained fraction was concentrated and dried in a vacuum to give a brown oily substance. To the oily substance was added hexane, followed by irradiation with ultrasonic waves. The resulting solid was recrystallized with toluene. The obtained solid was suction filtered and dried in a vacuum, and then purified by flash column chromatography (developing solvent: chloroform). The resulting fraction was concentrated to give a yellow oily substance. To this oily substance was added a mixed solvent of toluene/hexane, and the precipitated solid was suction filtered and dried in a vacuum to give 5.0 mg of the target white solid of R-DOL-Prna in a yield of 0.17%. The scheme of the above reaction is shown in (E5-1).

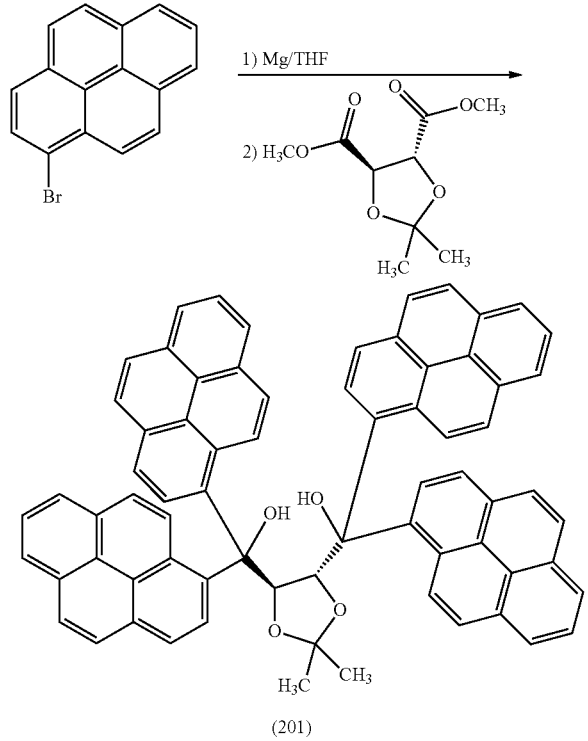

(E5-1)

This compound was identified as the target R-DOL-Prna by NMR.

¹H NMR data of the obtained substance, R-DOL-Prna, are as follows. ¹H NMR (TCE, 300 MHz): δ (ppm)=1.15 (s, 2H), 1.36 (s, 6H), 6.50 (s, 2H), 7.24-8.79 (m, 36H).

Figure 14A:
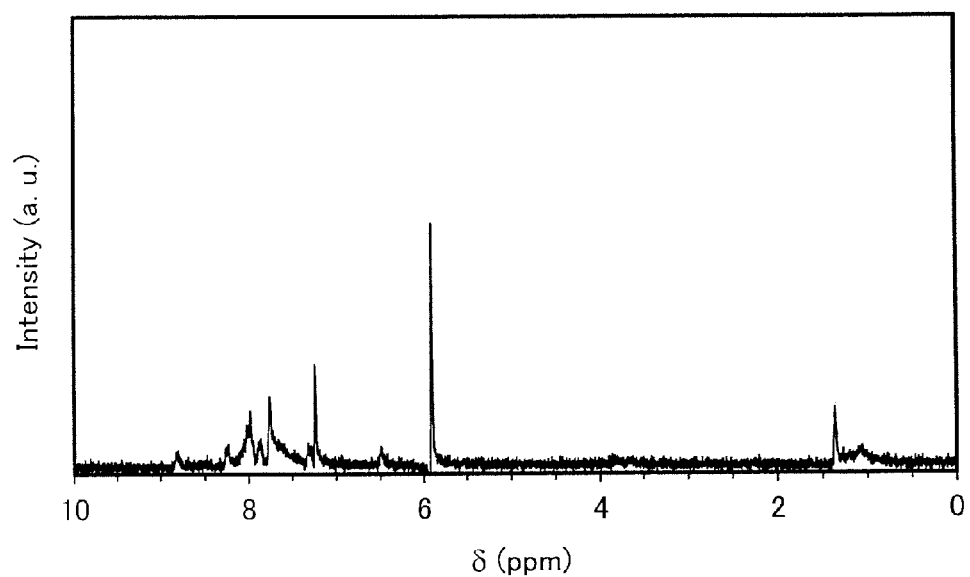
FIGS. 14A and 14B are $^1$H NMR charts of (4R,5R)-2,2-dimethyl-α,α,α',α'-tetra(pyren-1-yl)-1,3-dioxolane-4,5-dimethanol (R-DOL-Prna)
Figure 14B:
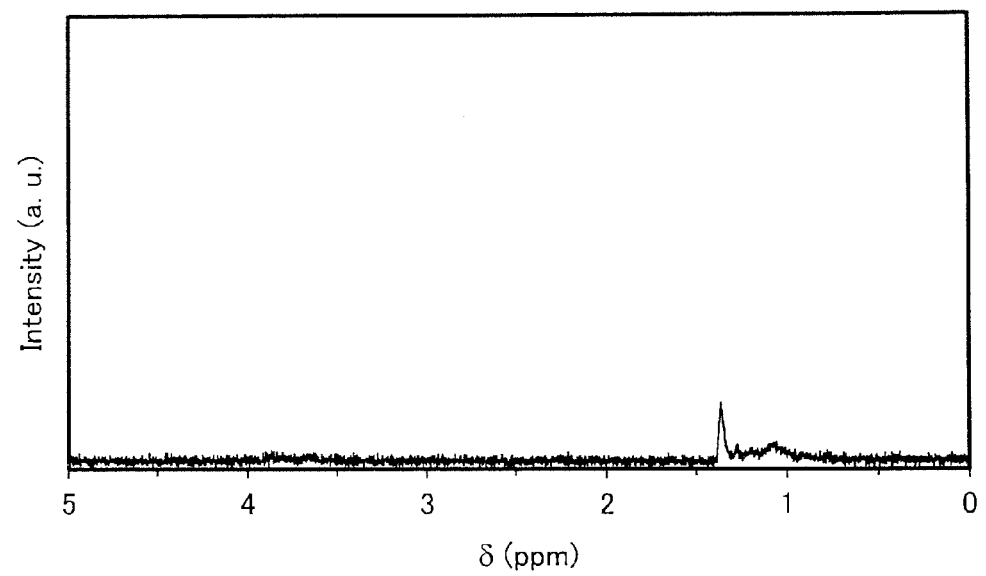
Figure 15:
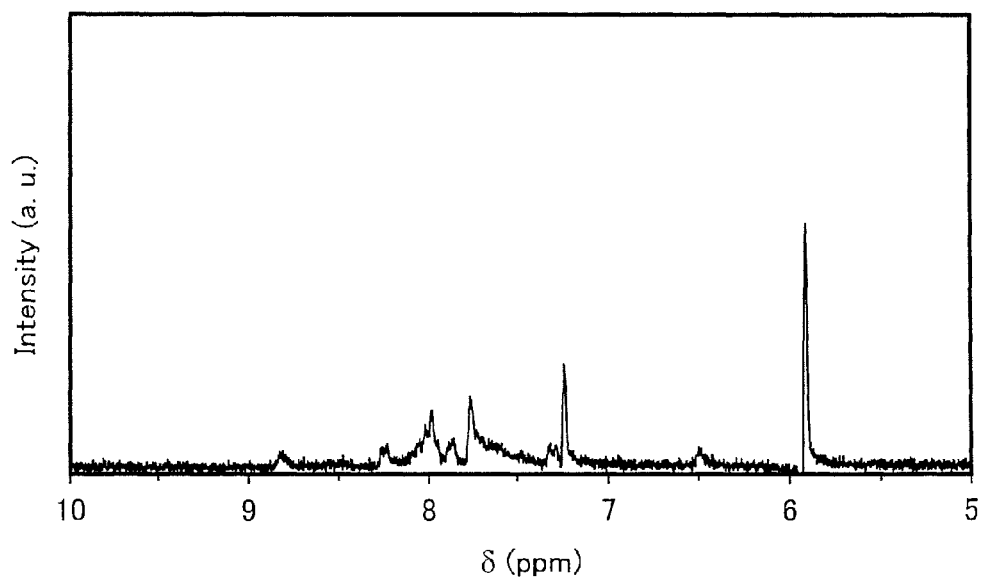
FIG. 15 is a $^1$H NMR chart of R-DOL-Prna.

FIGS. 14A and 14B and FIG. 15 show the ¹H NMR charts. Note that FIG. 14B is an enlarged chart showing a range of from 0 ppm to 5 ppm of FIG. 14A, and FIG. 15 is an enlarged chart showing a range of from 5 ppm to 10 ppm of FIG. 14A. The measurement results show that R-DOL-Prna, which was the target substance, was obtained.

HTP of a liquid crystal composition that is a mixture of R-DOL-Prna synthesized in this example and a nematic liquid crystal was measured. The measurement was performed at room temperature by the Grandjean-Cano wedge method. Note that the mixture ratio of the nematic liquid crystal to R-DOL-Prna in the liquid crystal composition was 99.9 wt %:0.1 wt % (=nematic liquid crystal R-DOL-Prna). As the nematic liquid crystal, a mixed liquid crystal containing a mixed liquid crystal E-8 (produced by LCC Corporation, Ltd.), CPP-3FF (produced by Daily Polymer Corporation), and PEP-5CNF (produced by Daily Polymer Corporation) was used. The mixture ratio was 40 wt %:30 wt %:30 wt % (=E-8: CPP-3FF PEP-5CNF).

The measurement results show that the HTP of the liquid crystal composition including R-DOL-Prna was 110 μm⁻¹, and by adding an extremely small amount of R-DOL-Prna into the liquid crystal composition, the liquid crystal composition can have high HTP. Thus, R-DOL-Prna is a chiral material having strong twisting power, which means the proportion of a chiral material in a liquid crystal composition can be reduced.

Thus, R-DOL-Prna synthesized in this example has proved favorable as a chiral material of a liquid crystal composition. Furthermore, the liquid crystal composition in which one embodiment of the present invention is used has strong twisting power, so that a liquid crystal display device with high contrast can be achieved with the use of the liquid crystal composition.

EXAMPLE 9

In this example, two kinds of liquid crystal compositions that are each one embodiment of the present invention and two kinds of TN mode liquid crystal elements including the liquid crystal compositions were prepared, and characteristics of the liquid crystal compositions and the liquid crystal elements were evaluated.

In the two kinds of liquid crystal compositions prepared in this example, a mixed liquid crystal ZLI-4792 (produced by Merck) was used in common as a nematic liquid crystal. As chiral materials for the respective liquid crystal compositions, R-DOL-αNpand R-DOL-Prna described in Examples 7 and 8, respectively, were used. In both of the liquid crystal compositions, the proportion of the chiral material R-DOL-αNp and R-DOL-Prna with respect to the nematic liquid crystal ZLI-4792 was 0.01 wt %.

The helical pitches of the two kinds of liquid crystal compositions prepared in this example were 72.8 μm and 55.3 μm, which were measured at room temperature by the Grandjean-Cano wedge method.

Then, the alignment in the transmissive TN cells before and after voltage application was observed. The TN cells were prepared in the same way as that described in Example 4.

The resulting two kinds of liquid crystal elements were observed by crossed nicols observation with a polarizing microscope (MX-61L produced by Olympus Corporation), which showed that line defects due to a reverse twist were not generated at all and favorable alignment was obtained in all the liquid crystal elements.

Next, voltage-transmittance characteristics of these two kinds of liquid crystal elements were measured with a RETS+VT measurement system (produced by Otsuka Electronics Co., Ltd.). The voltage was applied at 0.2 V intervals in the range of from 0 V to 10 V. After the measurement, crossed nicols observation with the polarizing microscope was performed again, which showed that, in both kinds of liquid crystal elements, line defects due to the reverse twist were not generated at all and favorable alignment was obtained also after the voltage application.

The above-described results indicate that the liquid crystal compositions of embodiments of the present invention can be used for TN mode elements by including the dioxolane derivative represented by General Formula (G2) as a chiral material.

EXAMPLE 10

In this example, (R-DOL-Prna whose synthesis method is shown in Example 8 and a nematic liquid crystal were mixed to prepare a liquid crystal composition. Note that the mixture ratio of the nematic liquid crystal to R-DOL-Prna in the liquid crystal composition was 94.9 wt %:5.1 wt % (=nematic liquid crystal: R-DOL-Prna). As the nematic liquid crystal, a mixed liquid crystal containing a mixed liquid crystal E-8 (produced by LCC Corporation, Ltd.), CPP-3FF (produced by Daily Polymer Corporation), and PEP-SCNF (produced by Daily Polymer Corporation) was used. The mixture ratio was 40 wt %:30 wt %:30 wt % (=E-8: CPP-3FF: PEP-5CNF).

In this example, the liquid crystal composition in the liquid crystal element was made to be an isotropic phase at first. Then, the liquid crystal composition was observed with a polarizing microscope while the temperature was decreased by 1.0° C. per minute with a temperature controller, and the temperature at which the liquid crystal composition is transformed to a blue phase was measured. The liquid crystal composition of this example exhibited a blue phase at 50.3° C.

The above results show that the liquid crystal composition of one embodiment of the present invention can exhibit a blue phase by including the dioxolane derivative represented by General Formula (G2) as a chiral material.

EXAMPLE 11

This example shows an example for synthesizing (4R,5R)-2,2-dimethyl-1,3-dioxolane-4,5-dimethanol bis {4-[4-(n-hexyl-1-oxy)phenyl]benzoate} (abbreviation: R-DOL-1EPPO6), which is the dioxolane derivative represented by Structural Formula (300) in Embodiment 3.

Into a 50-mL recovery flask, 0.34 g (2.1 mmol) of (−)-2,3-O-isopropylidene-D-threitol, 1.3 g (4.2 mmol) of 4-[4-(n-hexyl-1-oxy)phenyl]benzoic acid, 0.22 g (1.8 mmol) of N,N-dimethyl-4-aminopyridine (DMAP), and 2.1 mL of dichloromethane were put, and the mixture was stirred. To this mixture, 0.88 g (4.6 mmol) of 1-ethyl-3-(3-dimethylaminopropyl)carbodiimide hydrochloride (EDC) was added, and this mixture was stirred overnight at room temperature under atmospheric pressure. After a predetermined period, water was added, and the aqueous layer of the obtained mixture was subjected to extraction with dichloromethane. The extracted solution and the organic layer were combined, washed with water, a saturated aqueous solution of sodium hydrogen carbonate, and saturated saline, and dried with magnesium sulfate.

This mixture was separated by gravity filtration, and the obtained filtrate was concentrated to give a light-brown solid. This solid was purified by silica gel column chromatography (developing solvent: chloroform). The resulting fraction was concentrated to give a white solid. This solid was purified by HPLC (developing solvent: chloroform). The resulting fraction was concentrated to give a white solid.

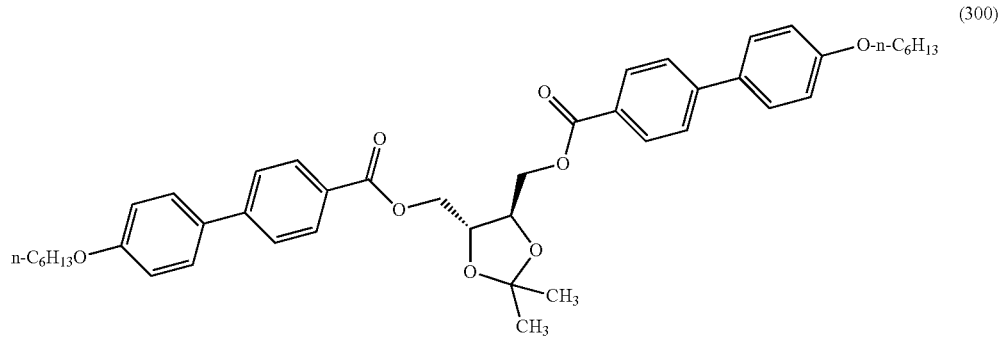

(300)

To this solid, hexane and methanol were added, and the mixture was subjected to irradiation with ultrasonic waves. The solid was suction-filtered to give 0.87 g of the target white solid of R-DOL-1EPPO6 in a yield of 58%. The scheme of the above reaction is shown in (E6-1).

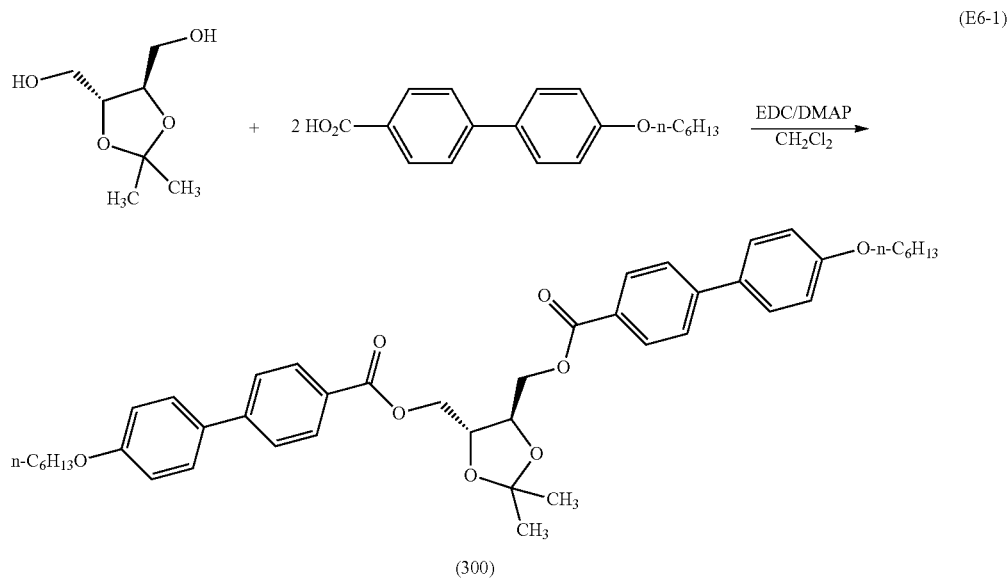

(E6-1)

This compound was identified as the target R-DOL-1EPPO6 by NMR.

$^1$H NMR data of the obtained substance. R-DOL-1EPPO6, are as follows. $^1$H NMR (CDCl$_3$, 300 MHz): δ (ppm)=0.92 (s, 6H), 1.32-1.38 (m, 12H), 1.49 (s, 6H), 1.76-1.86 (m, 4H), 4.00 (t, 4H), 4.36 (s, 2H), 4.49-4.62 (m, 4H), 6.97 (d, 2H), 7.54 (d, 2H), 7.61 (d, 2H), 8.08 (d, 2H).

Figure 16A:
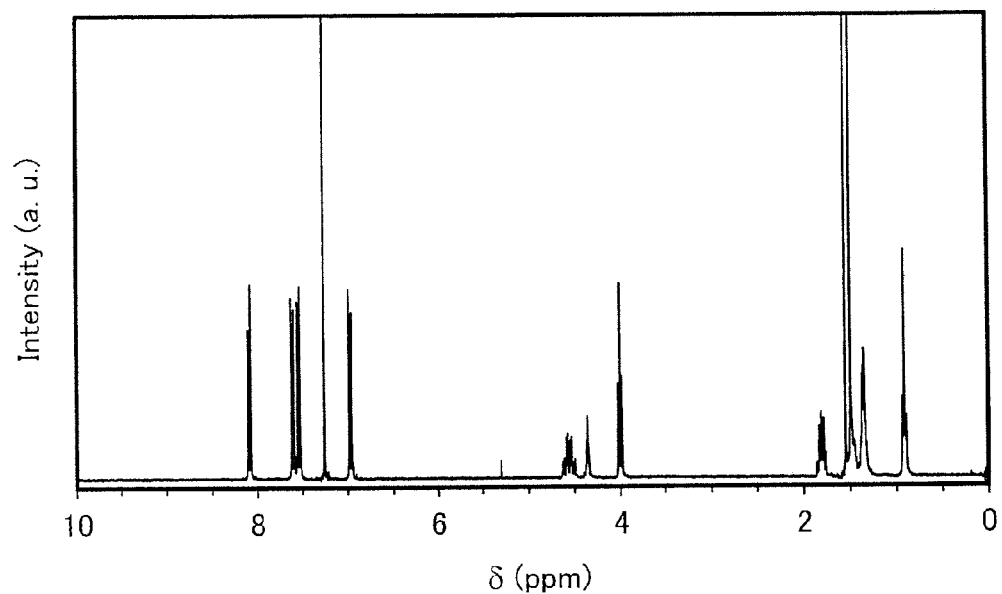
FIGS. 16A and 16B are $^1$H NMR charts of (4R,5R)-2,2-dimethyl-1,3-dioxolane-4,5-dimethanol bis{4-[4-(n-hexyl-1-oxy)phenyl]benzoate} (R-DOL-1EPPO6)
Figure 16B:
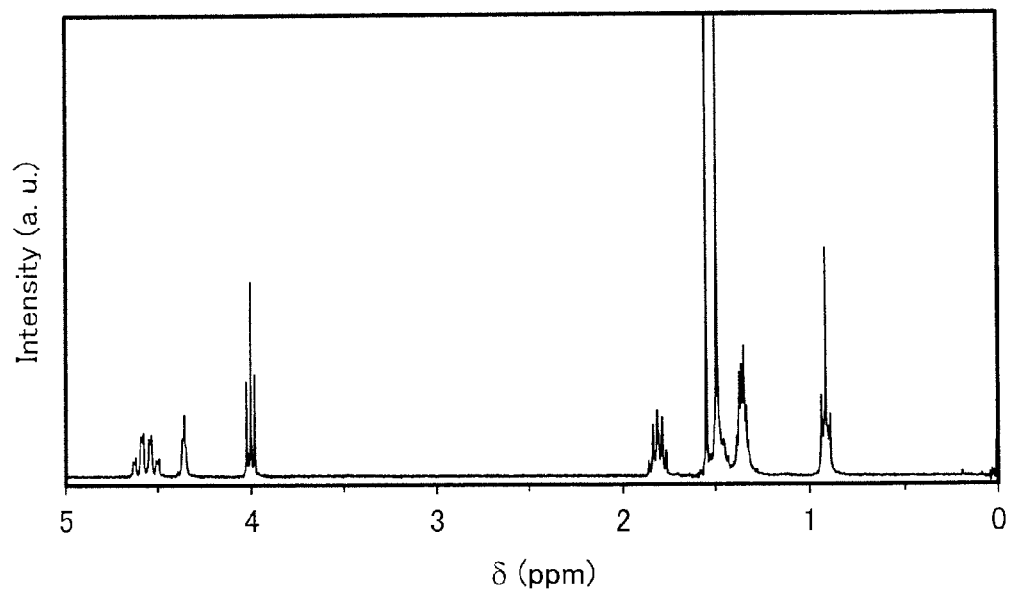
Figure 17:
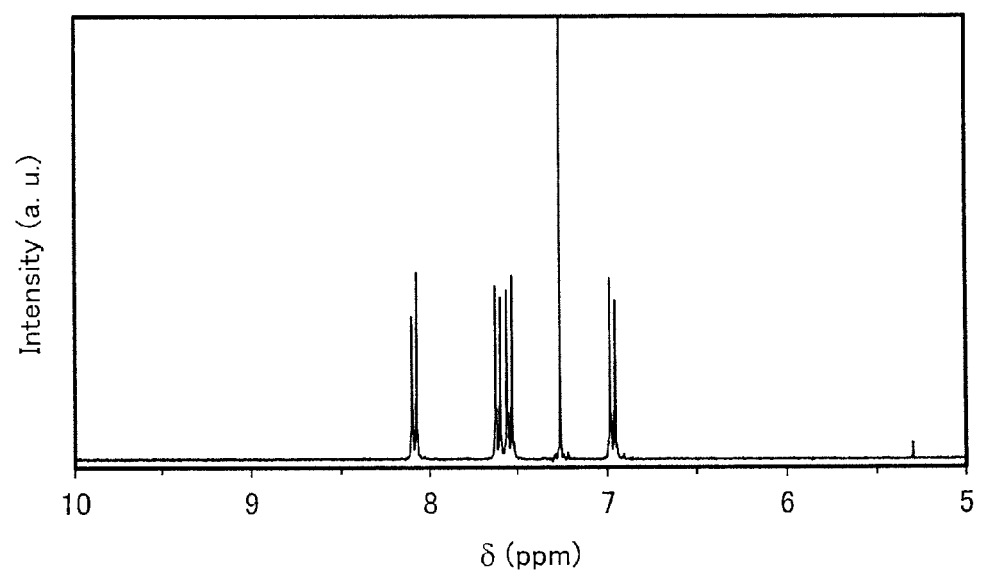
FIG. 17 is a $^1$H NMR chart of R-DOL-1EPPO6.

FIGS. 16A and 16B and FIG. 17 show the $^1$H NMR charts. Note that FIG. 16B is an enlarged chart showing a range of from 0 ppm to 5 ppm of FIG. 16A, and FIG. 17 is an enlarged chart showing a range of from 5 ppm to 10 ppm of FIG. 16A. The measurement results show that R-DOL-1EPPO6, which was the target substance, was obtained.

HTP of a liquid crystal composition that is a mixture of R-DOL-1EPPO6 synthesized in this example and a nematic liquid crystal was measured. The measurement was performed at room temperature by the Grandjean-Cano wedge method. Note that the mixture ratio of the nematic liquid crystal to R-DOL-1EPPO6 in the liquid crystal composition was 99.9 wt %:0.1 wt % (=nematic liquid crystal: R-DOL-1EPPO6). As the nematic liquid crystal, a mixed liquid crystal containing a mixed liquid crystal E-8 (produced by LCC Corporation, Ltd.), CPP-3FF (produced by Daily Polymer Corporation), and PEP-5CNF (produced by Daily Polymer Corporation) was used. The mixture ratio was 40 wt %:30 wt %:30 wt % (=E-8: CPP-3FF: PEP-5CNF).

The measurement results show that the HTP of the liquid crystal composition including R-DOL-1EPPO6 was 84 and by adding an extremely small amount of R-DOL-1EPPO6 into the liquid crystal composition, the liquid crystal composition can have high HTP. Thus, R-DOL-1EPPO6 is a chiral material having strong twisting power, which means that the proportion of a chiral material in a liquid crystal composition can be reduced.

Thus, R-DOL-1EPPO6 synthesized in this example has proved favorable as a chiral material of a liquid crystal composition. Furthermore, the liquid crystal composition in which one embodiment of the present invention is used has strong twisting power, so that a liquid crystal display device with high contrast can be achieved with the use of the liquid crystal composition.

EXAMPLE 12

In this example, a liquid crystal composition of one embodiment of the present invention and a TN mode liquid crystal element including the liquid crystal composition were prepared, and characteristics of the liquid crystal composition and the liquid crystal element were evaluated.

In the liquid crystal composition prepared in this example, a mixed liquid crystal ZLI-4792 (produced by Merck) was used as a nematic liquid crystal. As a chiral material, R-DOL-1EPPO6 described in Example 11 was used. In the liquid crystal composition, the proportion of the chiral material R-DOL-1EPPO6 with respect to the nematic liquid crystal ZLI-4792 was 0.04 wt %.

The helical pitch of the liquid crystal composition prepared in this example was 182.6 μm, which was measured at room temperature by the Grandjean-Cano wedge method.

Then, the alignment in the transmissive TN cells before and after voltage application was observed. The TN cells were prepared in the same way as that described in Example 4.

The resulting liquid crystal element was observed by crossed nicols observation with a polarizing microscope (MX-61L produced by Olympus Corporation), which showed that line defects due to a reverse twist were not generated at all and favorable alignment was obtained.

Next, voltage-transmittance characteristics of this liquid crystal element were measured with a RETS+VT measurement system (produced by Otsuka Electronics Co., Ltd.). The voltage was applied at 0.2 V intervals in the range of from 0 V to 10 V. After the measurement, crossed nicols observation with the polarizing microscope was performed again, which showed that line defects due to the reverse twist were not generated at all and favorable alignment was obtained also after the voltage application.

The above-described results indicate that the liquid crystal composition of one embodiment of the present invention can be used for a TN mode element by including the dioxolane derivative represented by General Formula (G4) as a chiral material.

EXAMPLE 13

In this example, R-DOL-1EPPO6 whose synthesis method is shown in Example 11 and a nematic liquid crystal were mixed to prepare a liquid crystal composition. Note that the mixture ratio of the nematic liquid crystal to R-DOL-1EPPO6 in the liquid crystal composition was 93.3 wt %:6.7 wt % (=nematic liquid crystal: R-DOL-1EPPO6). As the nematic liquid crystal, a mixed liquid crystal containing a mixed liquid crystal E-8 (produced by LCC Corporation, Ltd.), CPP-3FF (produced by Daily Polymer Corporation), and PEP-5CNF (produced by Daily Polymer Corporation) was used. The mixture ratio was 40 wt %:30 wt %:30 wt % (=E-8: CPP-3FF: PEP-5CNF).

In this example, the liquid crystal composition in the liquid crystal element was made to be an isotropic phase at first. Then, the liquid crystal composition was observed with a polarizing microscope while the temperature was decreased by 1.0° C. per minute with a temperature controller, and the temperature at which the liquid crystal composition is transformed to a blue phase was measured. It was confirmed that the liquid crystal composition of this example exhibited a blue phase at 62.4° C. [0[釈迦戸]310]

The above results show that the liquid crystal composition of one embodiment of the present invention can exhibit a blue phase by including the dioxolane derivative represented by General Formula (G4) as a chiral material.

This application is based on Japanese Patent Application serial no. 2013-159187 filed with Japan Patent Office on Jul. 31, 2013, Japanese Patent Application serial no. 2013-159194 filed with Japan Patent Office on Jul. 31, 2013, and Japanese Patent Application serial no. 2013-159197 filed with Japan Patent Office on Jul. 31, 2013, the entire contents of which are hereby incorporated by reference.

What is claimed is:

1. A compound represented by formula (G2):

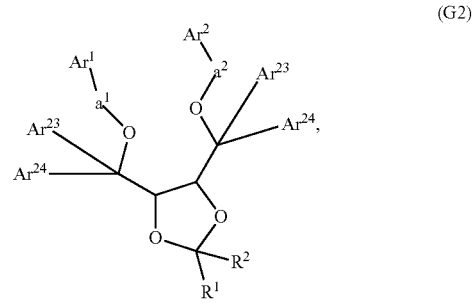

(G2)

wherein:

Ar$^1$ and Ar$^2$ independently represent hydrogen, a substituted or unsubstituted aryl group having 6 to 12 carbon atoms, a substituted or unsubstituted cycloalkyl group having 3 to 12 carbon atoms, or a substituted or unsubstituted cycloalkenyl group having 4 to 12 carbon atoms;

Ar²³ and Ar²⁴ independently represent a substituted or unsubstituted pyrenyl group;

a¹ and a² independently represent a substituted or unsubstituted alkylene group having 1 to 4 carbon atoms or a single bond; and R¹ and R² independently represent hydrogen, a substituted or unsubstituted alkyl group having 1 to 6 carbon atoms, a substituted or unsubstituted alkoxy group having 1 to 6 carbon atoms, or a substituted or unsubstituted aryl group having 6 to 12 carbon atoms.

2. The compound according to claim 1, wherein:

Ar¹ and Ar² each represent hydrogen; and a¹ and a² each represent a single bond.

3. The compound according to claim 1, wherein the compound is optically active.

4. The compound according to claim 1, wherein the compound is represented by formula (201):

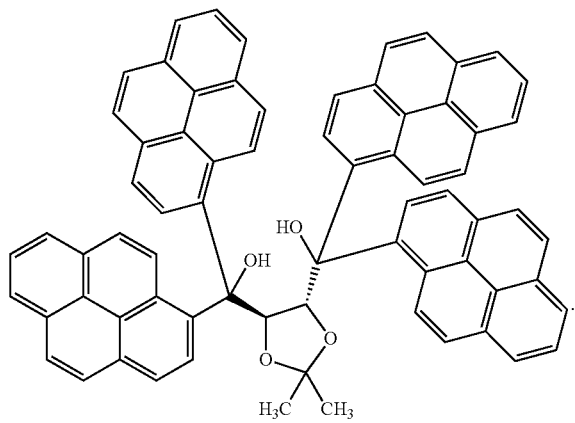

(201)

5. A composition comprising:
the compound according to claim 1; and
a liquid crystal.

6. A liquid crystal display device comprising the composition according to claim 5.

7. A compound represented by formula (G4):

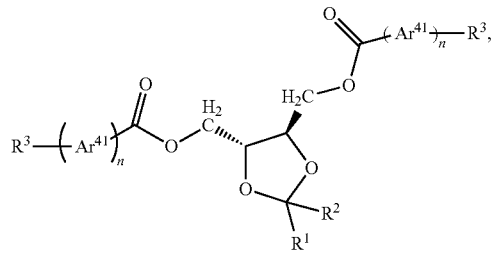

(G4)

wherein:

Ar⁴¹ represents a substituted or unsubstituted arylene group having 6 to 12 carbon atoms;

n represents 2;

R¹ and R² independently represent hydrogen, a substituted or unsubstituted alkyl group having 1 to 6 carbon atoms, a substituted or unsubstituted alkoxy group having 1 to 6 carbon atoms, or a substituted or unsubstituted aryl group having 6 to 12 carbon atoms;

R³ represents hydrogen, a substituted or unsubstituted alkyl group having 1 to 6 carbon atoms, or a substituted or unsubstituted alkoxy group having 1 to 6 carbon atoms.

8. The compound according to claim 7, wherein R³ represents a substituted or unsubstituted alkoxy group having 1 to 6 carbon atoms.

9. The compound according to claim 7, wherein the compound is optically active.

10. The compound according to claim 7, wherein the compound is represented by formula (300):

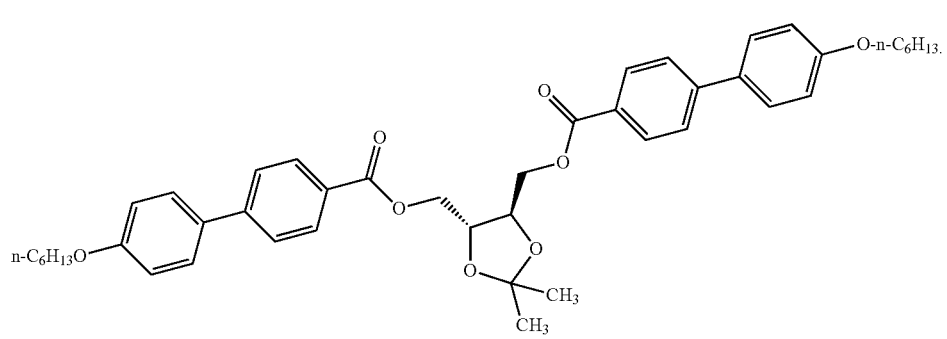

(300)

11. A composition comprising:
the compound according to claim 7; and
a liquid crystal.

12. A liquid crystal display device comprising the composition according to claim 11.

* * * * *